(12) United States Patent
Everett et al.

(10) Patent No.: US 8,283,340 B2
(45) Date of Patent: Oct. 9, 2012

(54) TREATMENT OR PROPHYLAXIS OF PROLIFERATIVE CONDITIONS

(75) Inventors: Steven Albert Everett, Mountain View, CA (US); Saraj Ulhaq, Monifieth Dundee (GB)

(73) Assignee: The University of the University of Dundee, Dundee (GB)

( * ) Notice: Subject to any disclaimer, the term of this patent is extended or adjusted under 35 U.S.C. 154(b) by 89 days.

(21) Appl. No.: 12/771,923

(22) Filed: Apr. 30, 2010

(65) Prior Publication Data

US 2010/0305070 A1 Dec. 2, 2010

Related U.S. Application Data

(60) Provisional application No. 61/174,884, filed on May 1, 2009.

(30) Foreign Application Priority Data

May 1, 2009 (GB) .................................. 0907551.6

(51) Int. Cl.
*A61K 31/665* (2006.01)
*C07F 9/28* (2006.01)
(52) U.S. Cl. ........................ 514/100; 514/457; 549/220
(58) Field of Classification Search .................. 514/100, 514/457; 549/220
See application file for complete search history.

(56) References Cited

U.S. PATENT DOCUMENTS

| 2005/0130973 A1 | 6/2005 | Xiang et al. |
| 2006/0258656 A1 | 11/2006 | Matteucci et al. |

FOREIGN PATENT DOCUMENTS

| EP | 0247381 A2 | 12/1987 |
| EP | 0363796 A1 | 4/1990 |
| EP | 1676834 A1 | 7/2006 |
| WO | WO 99/40056 A1 | 8/1999 |
| WO | WO 99/40944 A2 | 8/1999 |
| WO | WO 01/72680 A1 | 10/2001 |
| WO | WO 02/46193 A2 | 6/2002 |
| WO | WO 03/028713 A2 | 4/2003 |
| WO | WO 03/029176 A1 | 4/2003 |
| WO | WO 2006/009826 A1 | 1/2006 |
| WO | WO 2010/125350 A1 | 11/2010 |

OTHER PUBLICATIONS

Bankovic et al., "Identification of genes associated with non-small-cell lung cancer promotion and progression", Lung Cancer, vol. 67, No. 2, pp. 151-159 (2010).
Barnett et al., "Cytochrome P450 1B1 expression in glial cell tumors: an immunotherapeutic target", Clin. Cancer Res., vol. 13, No. 12, pp. 3559-3567 (2007).
Cali et al., "Luminogenic cytochrome P450 assays", Expert. Opin. Drug Metabolism Toxicol., 2(4): 629-645, 2006.
Carnell et al., "Target validation of cytochrome P450 CYP1B1 in prostate carcinoma with protein expression in associated hyperplastic and premalignant tissue", Int. J. Radiat. Oncol, Biol. Phys., vol. 58, No. 2, 500-509 (2004).
Chang et al., "Real-time polymerase chain reaction analysis of CYP1B1 gene expression in human liver", Toxicol. Sci., vol. 71, No. 1, pp. 11-19 (2003).
Chang and Waxman, "Enzymatic analysis of cDNA-expressed human CYP1A1, CYP1A2, and CYP1B1 with 7-ethoxyresorufin as substrate", Methods Mol. Biol., vol. 320, pp. 85-90 (2006).
Chun et al., "A new selective and potent inhibitor of human cytochrome P450 1B1 and its application to antimutagenesis", Cancer Res., vol. 61, No. 22, pp. 8164-8170 (2001).
De Montellano, (ed.), "Cytochrome P450: structure, mechanism, and biochemistry", Kluwer Academic/Plenum Publishers, New York, 2005 *Title page and Table of Conents only*.
Downie et al., "Profiling cytochrome P450 expression in ovarian cancer: identification of prognostic markers", Clin. Cancer Res., vol. 11, No. 20, pp. 7369-7375 (2005).
Duan et al., "Potent and highly selective hypoxia-activated achiral phosphoramididate mustards as anticancer drugs", J. Med Chem., vol. 51, pp. 2412-2420 (2008).
Edler et al., "Prevalence of asymptomatic bacteriuria among Egyptian elder persons living in the rural areas", Eur. J. Cancer, vol. 45, No. 4. pp. 705-712 (2004).
Everett et al., "Modifying rates of reductive elimination of leaving groups from indolequinone prodrugs: a key factor in controlling hypoxia-selective drug release", Biochem. Pharmacol., vol. 63, pp. 1629-1639 (2002).
Everett et al., "Profiling cytochrome P450 CYP1 enzyme expression in primary melanoma and disseminated disease utilizing spectral imaging microscopy (SIM)", J. Clin. Oncology, vol. 25, pp. 486s, Abstract: 8556 (2007).
Flader et al., "Development of novel quinone phosphorodiamidate prodrugs targeted to DT-diaphorase", J. Med. Chem., vol. 43, No. 16, pp. 3157-3167 (2000).
Gibson et al., "Cytochrome P450 1B1 (CYP1B1) is overexpressed in human colon adenocarcinomas relative to normal colon: implications for drug development", Mol. Cancer Ther., vol. 2, No. 6, pp. 527-534 (2003).
Greer et al., "Cytochrome P450 1B1 (CYP1B1) is expressed during the malignant progression of head and neck squamus cell carcinoma (HNSCC)", Proc. Am. Assoc. Cancer Res., vol. 45, Abstract # 3701 (2004).

(Continued)

*Primary Examiner* — Rei-tsang Shiao
(74) *Attorney, Agent, or Firm* — Seed IP Law Group PLLC

(57) ABSTRACT

The disclosure relates to novel compounds for use in the treatment or prophylaxis of cancers and other proliferative conditions that are for example characterized by cells that express cytochrome P450 1B1 (CYP1B1) and allelic variants thereof. Also provided are pharmaceutical compositions comprising one or more such compounds for use in medical therapy, for example in the treatment of prophylaxis of cancers or other proliferative conditions, as well as methods for treating cancers or other conditions in human or non-human animal patients. Provided are methods for identifying novel compounds for use in the treatment of prophylaxis of cancers and other proliferative conditions that are for example characterized by cells that express CYP1B1 and allelic variants thereof. Finally, provided is a method for determining the efficacy of a compound as described herein in treating cancer.

29 Claims, 3 Drawing Sheets

OTHER PUBLICATIONS

Haas et al., "Expression of xenobiotic and steroid hormone metabolizing enzymes in human breast carcinomas". Int. J. Cancer, vol. 119, No. 8, pp. 1785-1791 2006.

Hernick et al., "Design, synthesis, and biological evaluation of indolequinone phosphoramidate prodrugs targeted to DT-diaphorase", J. Med. Chem., vol. 45, No. 16, pp. 3540-3548 (2002).

Hessel et al., "Differentiation status of human squamous cell carcinoma xenografts does not appear to correlate with the repopulation capacity of cionogenic tumor cells during fractionated irradiation", Int. J. Radiat. Biol., vol. 80, pp. 719-727(2004).

Ingelman-Sundberg, "The human genome project and novel aspects of cytochrome P450 research", Toxicol. Appl. Pharmacol., vol. 207, No. 2, pp. 52-56 (2005).

International Search Report from related PCT Patent Application No. PCT/GB2010/000860 mailed on Jun. 28, 2010, application published as WO 2010/125350 on Nov. 4, 2010.

Jensen et al., "In silico prediction of cytochrome P450 2D6 and 3A4 inhibition using Gaussian kernel weighted k-nearest neighbor and extended connectivity fingerprints, including structural fragment analysis of inhibitors versus noninhibitors", J. Med. Chem., vol. 50, No. 3. pp. 501-511 (2007).

Kumarakulasingham et al., "Cytochrome p450 profile of colorectal cancer: identification of markers of prognosis", Clin. Cancer Res., vol. 11, No. 10, pp. 3758-3765 (2005).

McFadyen et al., "Cytochrome P450 CYP1B1 over-expression in primary and metastatic ovarian cancer", Br. J. Cancer, vol. 85, No. 2, pp. 242-246 (2001).

McFadyen et al. "Cytochrome P450 CYP1B1 protein expression: a novel mechanism of anticancer drug resistance", Biochem. Pharmacol., vol. 62, No. 2, pp. 207-212 (2001).

McFadyen et al., "Cytochrome P450 CYP1B1 activity in renal cell carcinoma", Br. J. Cancer, vol. 91 No. 5, pp. 966-971 (2004).

McFadyen et al., "Cytochrome P450 enzymes: novel options for cancer therapeutics", Mol. Cancer Ther., vol. 3, No. 3, pp. 363-371 (2004).

McFadyen and Murray, "Cytochrome P450 1B1: a novel anticancer therapeutic target", Future Oncol., vol. 1, No. 2, pp. 259-263 (2005).

McKay et al., "Differential expression of CYP1A1 and CYP1B1 in human breast cancer", Biochem. Soc. Trans., vol. 24, No. 2, pp. 327s (1996).

Murray et al., "Tumor-Specific Expression of Cytochrome P450 CYP1B1", Cancer Res., vol. 57, No. 14, pp, 3026-3031 (1997).

Paine et al., "Functional high level expression of Cytochrome P450 CYP2D6 using baculoviral expression systems", Arch. Biochem. Biophys., vol. 328, pp. 143-150 (1996).

Patterson and Murray, "Tumor cytochrome P450 and drug activation", Curr. Pharm Des., vol. 8, No. 15, pp. 1335-1347 (2002).

Reiger et al., "Identification of a novel mammary-restricted cytochrome P450, CYP4Z1, with overexpression in breast carcinoma", Cancer Res., vol. 64, No. 7, pp. 2357-2364 (2004).

Rendic "Summary of information on human CYP enzymes: human P450 metabolism data" Drug Metab. Rev., vol. 34, pp. 83-448 (2002).

Sissung et al., "Pharmacogenetics and regulation of human cytochrome P450 1B1: implications in hormone-mediated tumor metabolism and a novel target for therapeutic intervention", Mol. Cancer Res., vol. 4, No. 3, pp. 135-150 (2006).

Sissung et al., "Association of the CYP1B1*3 allele with survival in patients with prostate cancer receiving docetaxel", Mol. Cancer Ther., vol. 7, No. 1, pp. 19-26 (2008).

Stark and Guengerich, "Characterization of orphan human cytochromes P450", Drug Metab. Rev., vol. 39, No. 2-3, pp. 627-637 (2007).

Su et al., "Overexpression of cytochrome P450 1B1 in advanced non-small cell lung cancer: a potential therapeutic target", Anticancer Res., vol. 29, No. 2, pp. 509-515 (2009).

Sutter et al., "Complete cDNA sequence of a human dioxin-inducible mRNA identifies a new gene subfamily of cytochrome P450 that maps to chromosome 2", J. Biol. Chem., vol. 269, No. 18, pp. 13092-13099 (1994).

Veith et al., "Comprehensive characterization of cytochrome P450 isozyme selectivity across chemical libraries", Nature Biotechnology, vol. 27, pp. 1050-1055 (2009).

Waxman and Change, "The use of 7-ethoxycoumarin to monitor multiple enzymes in the human CYP1, CYP2, CYP3 families", Cytochrome P450 Protocols, Second Edition, edited by Phillips and Shepherd, Methods in Molecular Biology, vol. 320, pp. 153-156 (2006).

Yaromina et al., "Pre-treatment number of clonogenic cells and their radiosensitivity are major determinants of local tumor control after fractionated irradiation", Radiother. Oncol., vol. 83, No. 3, pp. 304-310 (2007).

TREATMENT OR PROPHYLAXIS OF PROLIFERATIVE CONDITIONS

CROSS REFERENCE TO RELATED APPLICATIONS

This application claims the benefit of priority to U.S. Provisional Patent Application No. 61/174,884, filed May 1, 2009, and to U.K. Patent Application No. 0907551.6, also filed May 1, 2009, each of which is incorporated herein by reference in its entirety.

FIELD

The present invention relates to novel compounds for use in the treatment or prophylaxis of cancers and other proliferative conditions that are for example characterized by cells that express cytochrome P450 1B1 (CYP1B1) and allelic variants thereof. The present invention also provides pharmaceutical compositions comprising one or more such compounds for use in medical therapy, for example in the treatment of prophylaxis of cancers or other proliferative conditions, as well as methods for treating cancers or other conditions in human or non-human animal patients. The present invention also provides methods for identifying novel compounds for use in the treatment of prophylaxis of cancers and other proliferative conditions that are for example characterized by cells that express CYP1B1 and allelic variants thereof. The present invention also provides a method for determining the efficacy of a compound of the invention in treating cancer.

BACKGROUND

CYP1B1 is a member of the dioxin-inducible CYP1 gene family which also includes CYP1A1 and CYP1A2 as described by Sutter et al. (*J. Biol. Chem.*, May 6; 269(18): 13092-9, 1994). CYP1B1 is a heme-thiolate mono-oxygenase enzyme that is capable of metabolizing and activating a variety of substrates including steroids, xenobiotics, drugs and/or prodrugs. CYP1B1 protein is expressed to a high frequency in a wide range of primary and metastatic human cancers of different histogenic types and is not expressed or at negligible levels in normal tissue. (see, e.g.: McFadyen M C, Melvin W T and Murray G I, "Cytochrome P450 Enzymes: Novel Options for Cancer Therapeutics", *Mol Cancer Ther.*, 3(3): 363-71, 2004; McFadyen M C and Murray G I, "Cytochrome P450 1B1: a Novel Anticancer Therapeutic Target", *Future Oncol.*, 1(2): 259-63, 2005; Sissung T M, Price D K, Sparreboom A and Figg W D, "Pharmacogenetics and Regulation of Human Cytochrome P450 1B1: Implications in Hormone-Mediated Tumor Metabolism and a Novel Target for Therapeutic Intervention", *Mol. Cancer Res.*, 4(3): 135-50, 2006).

More specifically, CYP1B1 has been shown to be expressed in bladder, brain, breast, colon, head and neck, kidney, lung, liver, ovarian, prostate and skin cancers, without being expressed in the corresponding normal tissue. For example, Barnett, et al., in *Clin. Cancer Res.*, 13(12): 3559-67, 2007, reported that CYP1B1 was over-expressed in glial tumours, including glioblastomas, anaplastic astrocytomas, oligodendrogliomas and anaplastic oligodendrogliomas, but not unaffected brain tissue; Carnell, et al., in *Int. J. Radiat. Oncol. Biol. Phys.*, 58(2): 500-9, 2004, reported that CYP1B1 was over-expressed in prostate adenonocarcinomas, but not in matched normal prostate tissue; Carnell, et al., 2004 (ibid.) also showed that CYP1B1 is expressed in (n=22, 100%) of bladder carcinomas; Downie, et al., in *Clin. Cancer Res.*, 11(20): 7369-75, 2005 and McFadyen, et al., in *Br. J. Cancer*, 85(2): 242-6, 2001, reported increased expression of CYP1B1 in primary and metastatic ovarian cancer, but not in normal ovary tissue; and Gibson, et al., in *Mol. Cancer Ther.*, 2(6): 527-34, 2003, and Kumarakulasingham, et al., in *Clin. Cancer Res.*, 11(10): 3758-65, 2005, reported that CYP1B1 was over-expressed in colon adenocarcinomas as compared to matched normal tissue.

Several studies have shown that CYP1B1 is over-expressed in breast cancer as compared to matched normal tissue (see, e.g.: Murray G I, Taylor M C, McFadyen M C, McKay J A, Greenlee W F, Burke M D and Melvin W T, "Tumor-Specific Expression of Cytochrome P450 CYP1B1", *Cancer Res.*, 57(14): 3026-31, 1997; Haas S, Pierl C, Harth V, Pesch B, Rabstein S, Bruning T, Ko Y, Hamann U, Justenhoven C, Brauch H and Fischer H P, "Expression of Xenobiotic and Steroid Hormone Metabolizing Enzymes in Human Breast Carcinomas". *Int. J. Cancer*, 119(8): 1785-91, 2006; McKay J A, Murray G I, Ah-See A K, Greenlee W F, Marcus C B, Burke M D and Melvin W T, "Differential Expression of CYP1A1 and CYP1B1 in Human Breast Cancer", *Biochem. Soc. Trans.*, 24(2): 327S, 1996).

Everett, et al., in *J. Clin. Oncology*, 25: 18S, 2007, reported that CYP1B1 was over-expressed in malignant melanoma and disseminated disease but not in normal skin. Chang, et al., in *Toxicol. Sci.*, 71(1): 11-9, 2003, reported that CYP1B1 protein is not present in normal liver but Everett, et al., 2007 (ibid.) confirmed CYP1B1 over-expression in melanoma stage IV metastasis to the liver but not in the adjacent normal liver tissue.

Greer, et al., in *Proc. Am. Assoc. Cancer Res.*, 45: 3701, 2004, reported that CYP1B1 was over-expressed during the malignant progression of head and neck squamous cell carcinoma but not in normal epithelium.

McFadyen, et al., in *Br. J. Cancer*, 91(5): 966-71, 2004, detected CYP1B1 in renal carcinomas but not in corresponding normal tissue.

Murray, et al., 2004 (ibid.) used immunohistochemistry to show over-expression of CYP1B1 in lung cancer cells as compared to normal lung tissue. Su, et al., in *Anti-Cancer Res.*, 2, 509-15, 2009, used immunohistochemistry to show over-expression of CYP1B1 in advanced stage IV non-small cell lung cancer compared to earlier stages of the disease.

It is evident from the numerous disclosures cited above that CYP1B1 expression is characteristic of a range of different cancers and other proliferative conditions, and that CYP1B1 expression may be used to define such a range of cancers and other conditions. As normal (non-cancerous) cells do not express significant levels of CYP1B1, it may also be reasonably expected that compounds that exhibit cytotoxicity in cells expressing CYP1B1, but are substantially non-cytotoxic in normal cells, would have utility as targeted anti-cancer agents in cancers characterized by CYP1B1 expression. By "targeted" is meant that such compounds could be delivered systemically and would only be activated in the presence of cancerous cells expressing CYP1B1, remaining substantially non-toxic to the rest of the body.

Furthermore, a number of cytochrome P450 enzymes are known to metabolise and detoxify a variety of anticancer drugs. McFadyen, et al. n (*Biochem Pharmacol.* 2001, Jul. 15; 62(2): 207-12) demonstrated a significant decrease in the sensitivity of docetaxel in cells expressing CYP1B1 as compared with non-CYP1B1 expressing cells. This finding indicates that the presence of CYP1B1 in cells may decrease their sensitivity to some cytotoxic drugs. CYP1B1-activated prodrugs may therefore be useful for the treatment of cancers whose drug resistance is mediated by CYP1B1.

Furthermore, the CYP1B1 gene is highly polymorphic in cancer and several single nucleotide polymorphisms contained within the CYP1B1 gene have been identified that alter the expression and/or activity of the encoded protein. Of these, the CYP1B1*3 (4326C>G; L432V) allele has been characterized by both increased expression and enzyme kinetics of CYP1B1 toward several substrates as described by Sissung, et al. in *Mol Cancer Ther.*, 7(1): 19-26, 2008 and references quoted therein. This finding indicates that not only CYP1B1 but the allelic variants of the enzyme may also contribute to prodrug activation and cancer targeting.

Prodrugs have been investigated as a means to lower the unwanted toxicity or some other negative attribute of a drug without loss of efficacy. A prodrug is a drug that has been chemically modified to render it inactive but that, subsequent to administration, is metabolized or otherwise converted to an active form of the drug in the body. The over-expression of CYP1B1 in primary tumours and metastatic disease compared to normal tissue offers a tremendous opportunity for the development of CYP1B1-activated prodrugs for targeted cancer therapy as reviewed by McFadyen et al., *Mol Cancer Ther.*, 3(3), 363-71, 2004. Indeed, the discovery and development of CYP1B1-activated prodrugs for targeted cancer therapy is likely to offer significant pharmacological advantages over existing non-targeted cytochrome P450-activated prodrugs used clinically such as the prodrug alkylating agents cyclophosphamide, ifosfamide, dacarbazine, procarbazine which are activated by cytochrome P450s expressed in normal tissue as reviewed by Patterson L H and Murray G I in *Curr Pharm Des.*, 8(15): 1335-47, 2002.

The human cytochrome P450 family contains 57 active isozymes, which function in normal metabolism, influence drug pharmacokinetics and effect negative outcomes in patients through drug-drug interactions. The cytochrome P450 isoenzymes metabolize approximately two thirds of known drugs in humans, with 80% of this attributable to five isozymes, namely CYP1A2, CYP2C9, CYP2C19, CYP2D6, and CYP3A4 as described in Ortiz de Montellano, P R (ed.) *Cytochrome P450: structure, mechanism, and biochemistry*, Kluwer Academic/Plenum Publishers, New York, 2005.

Among the genes discovered by initiatives in the human genome project are CYP2R1, CYP2W1, CYP2S1, CYP2S1, CYP2U1 but the function, polymorphism and regulation of these genes are still to be fully elucidated as reviewed by Ingelman-Sundberg, M., *Toxicol. Appl. Pharmacol.*, 207, 52-6, 2005. In addition to CYP1B1 a number of these cytochrome P450 oxidoreductases are extrahepatic and over-expressed in cancer. Several cytochrome P450s including CYP1B1, CYP2A/2B, CYP2F1, CYP2R1, CYP2U1, CYP3A5, CYP3A7, CYP4Z1, CYP26A1, and CYP 51 are present at a significantly higher level of intensity than in normal ovary as determined by immunohistochemistry and light microscopy, as described by Downie et al., *Clin. Cancer Res.*, 11(20): 7369-75, 2005. Furthermore, using similar methods of detection in primary colorectal cancer, several cytochrome P450s, including CYP1B1, CYP2S1, CYP2U1, CYP3A5, and CYP51, are frequently over-expressed compared to normal colon as descried by Kumarakulasingham et al., *Clin. Cancer Res.*, 11(10): 3758-65, 2005. In the same study several cytochrome P450s, including CYP1B1, CYP2A/2B, CYP2F1, CYP4V2, and CYP39, correlated with their presence in the primary tumour. CYP2W1 has also been shown to be over-expressed in colorectal cancer according to Elder et al., *Eur. J. Cancer*, 45(4): 705-12. CYP4Z1 is over-expressed in breast carcinoma is a gene associated with non-small cell lung cancer promotion and progression as described by Reiger et al., *Cancer Res.*, 64(7): 2357-64, 2004 and Bankovic et al., *Lung Cancer*, 67(2): 151-9, 2010, respectively.

A major challenge in the field is elucidation of the function of human cytochrome P450s of so-called 'orphan' status with unknown substrate specificity as reviewed by Strak K and Guengerich F P in *Drug Metab. Rev.*, 39(2-3): 627-37, 2007. A number of substrates are known for CYP1B1 few of which are specifically metabolised by the enzyme, for example 7-ethoxyresorufin undergoes oxidative de-ethylation when activated by all members of the CYP1 family, including CYP1A1, CYP1A2, and CYP1B1, as described by Chang T K and Waxman D J in *Method Mol. Biol.*, 320, 85-90, 2006. A number of fluorgenic and luminogenic probe substrates are available to assess cytochrome P450 activity with high sensitivity but they exhibit broad specificity and as such are metabolised by a range of cytochrome P450 enzymes in the CYP1, CYP2, and CYP3 families. For example, Cali et al., *Expert Opin. Drug Toxicol.*, 2(4): 62-45. 2006 describes the use of luminogenic substrates which couple to firefly luciferase luminescence in a technology called P450-Glo. Another example, is 7-ethoxycoumarin which undergoes cytochrome P450-catalyzed 7-ethoxycoumarin O-deethylation to release the highly fluorescent anion as described by Waxman D J and Change T K H in "The use of 7-ethoxycoumarin to monitor multiple enzymes in the human CYP1, CYP2, CYP3 families" in *Methods in Molecular Biology*, vol. 320, Cytochrome P450 Protocols, Second Edition, edited by Phillips I R and Shephard, E A, 2006.

Everett et al., *Biochem. Pharmacol.*, 63, 1629-39, 2002 describe the reductive fragmentation of model indolequinone prodrugs by cytochrome P450 reductase (not to be confused with cytochrome P450s) in anoxia to release the 7-hydroxy-4-methylcoumarin anion. The model prodrug was non-fluorescent at the pre-selected emission wavelength and reductive fragmentation could be accurately measured by monitoring the production of the coumarin anion ($\lambda_{ex}$=380 nm/$\lambda_{em}$=450 nm) using kinetic spectrofluorometry.

Interactions between a limited number of compounds (typically <100) and cytochrome P450s isozymes have been described but results from such studies are difficult to compare because of the differences in technologies, assay conditions and data analysis methods as described by Rendic, S. "Summary of information on human CYP enzymes: human P450 metabolism data" in *Drug Metab. Rev.*, 34, 83-448, 2002. Many computational strategies have been advanced to generate predictive cytochrome P450 isozyme substrate activity models but these are limited by a lack of a single large, diverse data set of cytochrome P450 isozyme activities as described by Veith et al., *Nature Biotechnology*, 27, 1050-55, 2009. The authors describe the construction of cytochrome P450 bioactivity databases using quantitative high-throughput screening (HTS) with a bioluminescent enzyme substrate inhibition assay to screen 17,143 chemical compounds against five cytochrome P450 isozymes (CYP1A2, 2C9, 2C19, 2D6, and 3A4) expressed in normal tissues mainly the liver and responsible for so-called phase 1 metabolism of drugs. It was concluded that the database should aid in constructing and testing new predictive models for cytochrome P450 activity to aid early stage drug discovery efforts.

Jensen et al., *J. Med. Chem.*, 50, 501-11, 2007 describe the methods for the in silico prediction of CYP2D6 and CYP3A4 inhibition based on a novel Gaussian Kernel weighted k-nearest neighbour (k-NN) algorithm based on Tanimoto similarity searches on extended connectivity fingerprints. The data set included modelling of 1153 and 1182 drug candidates tested for CYP2D6 and CYP3A4 inhibition in human liver microsomes. For CYP2D6, 82% of the classified test compounds were predicted to the correct class and CYP3A4, 88% of the classified test compounds were correctly classified.

Theoretically it may be possible to use cytochrome P450 HTS to build a large database of bioactivities for tumour and normal tissue cytochrome P450s and then develop a substrate prediction model as a basis for the design and synthesis of selective CYP1B1-activated prodrugs while screening out for pharmacological liabilities associated with Phase 1 metabolism by normal tissue cytochrome P450s. However, the reduction to practice is not obvious from prior art and has to be rationalised against prodrug structure and mechanism of conversion to the active drug when activated by tumour-expressing cytochrome P450s.

Utilization of so-called 'trigger-linker-effector' chemistry in prodrug design requires the activation of the trigger to initiate the fragmentation of a linker to release an effector (typically an active drug), the biological activity of which is masked in the prodrug form. The modular design of selective prodrugs targeted at tumour-expressing cytochrome P450s such as CYP1B1 require (1) the identification of selective trigger moieties, (2) the use of bio-stable linkers which fragment efficiently following trigger activation (usually by aromatic hydroxylation), and (3) suitable effectors or drugs which do not interfere with the efficiency of the triggering process.

CYP1B1 mRNA is expressed constitutively in all normal extrahepatic human tissues, though the protein is usually undetectable. In contrast, CYP1B1 protein is expressed at high levels in tumours. It is understood that for a large range of established or immortalized tumour cell lines (such as the MCF-7 breast cancer cells) originating from humans which have undergone significant passaging in vitro but does not constitutively express active CYP1B1 protein. Although CYP1B1 is not constitutively expressed in MCF-7 breast tumour cells it is possible to induce CYP1 enzyme expression both at the mRNA and protein level by treating with aryl hydrocarbon agonists such as the dioxin TCDD.

WO 99/40944 describes prodrugs that comprise a drug moiety bound to a carrier framework, the prodrug being described activated as though hydroxylation by CYP1B1 to release the drug moiety.

SUMMARY

We have surprisingly found that the compounds described herein, distinct over those described in WO 99/40944, are broken down in certain cells, in particular those that express cytochrome P450 1B1 (hereinafter CYP1B1), but not in normal cells, as a consequence of the compounds collapsing upon hydroxylation (e.g. effected by CYP1B1-expressing cells), and in particular by cancerous cells.

According to a first aspect therefore the present invention provides a compound of formula (I):

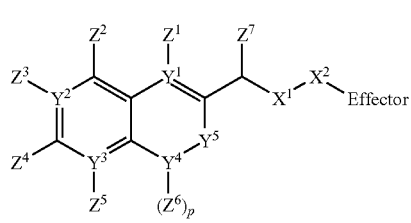

(wherein:
$X^1$ is such that $-X^1-X^2$ is $-O-X^2$, $-SO_2-O-X^2$, $-SO_2NZ^{10}-X^2$, conjugated alkenemethyloxy, conjugated alkenemethylthio, conjugated alkenemethylSO$_2$—O, conjugated alkenemethyl-SO$_2$NZ$^{10}$ or of the formula:

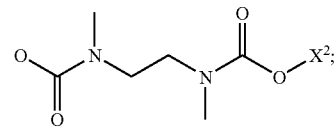

$-X^2$ is absent or is such that $X^1-X^2$-Effector is one of

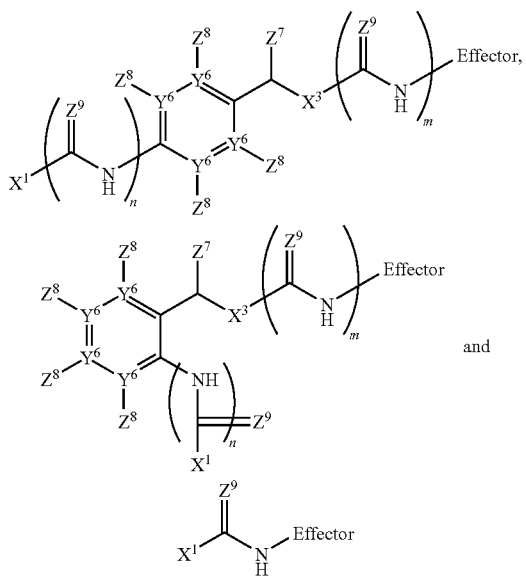

each n and m is independently 0 or 1;
p is 0, 1 or 2;
$X^3$ is oxygen or sulfur and additionally, when m=0, may be $SO_2-O$, $SO_2NZ^{10}$, conjugated alkenemethyloxy, conjugated alkenemethylthio, conjugated alkenemethyl-SO$_2$—O or conjugated alkenemethyl-SO$_2$NZ$^{10}$;
each of $Y^1$, $Y^2$ and $Y^3$ is independently carbon or nitrogen, wherein if $Y^1$ is nitrogen, $Z^1$ is absent, if $Y^2$ is nitrogen, $Z^3$ is absent and if $Y^3$ is nitrogen, $Z^5$ is absent;
$Y^4$ is an oxygen, carbon or nitrogen atom, sulfoxide or sulfone;
—$Y^5$— is either (i) a single bond, (ii) =CH—, wherein the double bond = in =CH— is connected to $Y^4$, or (iii) —$CH_2$— or —$CH_2CH_2$—, or one of (ii) to (iii) wherein the hydrogen atom in (ii) is or one or more hydrogen atoms in (iii) are replaced with a substituent $Z^{11}$, wherein $Z^{11}$ is selected independently from alkyl, alkenyl, alkynyl, aryl, aralkyl, alkyloxy, alkenyloxy, alkynyloxy, aryloxy, aralkyloxy, alkylthioxy, alkenylthioxy, alkynylthioxy, arylthioxy, aralkylthioxy, amino, hydroxy, thio, halo, carboxy, formyl, nitro and cyano;

each of $Z^1$-$Z^4$, where present, are independently selected from hydrogen, alkyl, alkenyl, alkynyl, aryl, aralkyl, alkyloxy, alkenyloxy, alkynyloxy, aryloxy, aralkyloxy, alkylthioxy, alkenylthioxy, alkynylthioxy, arylthioxy, aralkylthioxy, amino, hydroxy, thio, halo, carboxy, formyl, nitro and cyano; and $Z^5$, where present, is independently selected from hydrogen alkyl, alkenyl, alkynyl, aryl, aralkyl, alkyloxy, alkenyloxy, alkynyloxy, aryloxy, aralkyloxy, alkylthioxy, alkenylthioxy, alkynylthioxy, arylthioxy, aralkylthioxy, amino, hydroxy, thio, carboxy, formyl, nitro and cyano, or one of $Z^2$ & $Z^3$, $Z^3$ & $Z^4$ and $Z^4$ and $Z^5$ together with the atoms to which they are connected form an aromatic ring fused to the remainder of the compound, provided that at least one of $Z^1$, $Z^2$ and $Z^4$ is hydrogen;

$Z^6$ is selected from hydrogen, alkyl, alkenyl, alkynyl, aryl and aralkyl;

none, one or two of $Y^6$ may be nitrogen atoms with the remainder being carbon atoms;

each $Z^7$ is independently hydrogen, alkyl or aryl;

each $Z^8$ is independently selected from hydrogen, an electron withdrawing group, unsubstituted $C_1$-$C_6$ alkyl, substituted $C_1$-$C_6$ alkyl, unsubstituted $C_1$-$C_6$ alkoxy, and substituted $C_1$-$C_6$ alkoxy where the substituted alkyl or alkoxy are substituted with one or more groups selected from ether, amino, mono- or di-substituted amino, cyclic $C_1$-$C_5$ alkylamino, imidazolyl, $C_1$-$C_6$ alkylpiperazinyl, morpholino, thiol, thioether, tetrazole, carboxylic acid, ester, amido, mono- or di-substituted amido, N-connected amide, N-connected sulfonamide, sulfoxy, sulfonate, sulfonyl, sulfoxy, sulfinate, sufinyl, phosphonooxy, phosphate and sulfonamide;

each $Z^9$ is independently oxygen or sulfur;

$Z^{10}$ is hydrogen or alkyl, for example a $C_{1-4}$ alkyl;

Effector is a molecule having a pharmacological, diagnostic or screening function), or a pharmaceutically acceptable salt, ester, amide or solvate thereof.

Viewed from a second aspect, the invention provides a composition comprised of a compound according to the first aspect of the invention, or a pharmaceutically acceptable salt, ester, amide or solvate thereof, together with a pharmaceutically acceptable carrier.

Viewed from a third aspect the invention provides a compound according to the first aspect of the invention, or a pharmaceutically acceptable salt, ester, amide or solvate thereof, for use as a medicament.

Viewed from a fourth aspect, the invention provides a compound according to the first aspect of the invention, or a pharmaceutically acceptable salt, ester, amide or solvate thereof, for use in a method of treatment or prophylaxis of a proliferative condition.

Viewed from a fifth aspect, the invention provides a method of treatment or prophylaxis of a proliferative condition, said method comprising administering a therapeutically or prophylactically useful amount of a compound according to the first aspect of the invention, or pharmaceutically acceptable salt, ester, amide or solvate thereof, to a subject in need thereof.

Viewed from a sixth aspect, the invention provides the use of a compound according to the first aspect of the invention or a pharmaceutically acceptable salt, ester, amide or solvate thereof, for the preparation of medicament for use in a method of treatment or prophylaxis of a proliferative condition.

Viewed from a seventh aspect, the invention provides a method of identifying a compound that is specifically activated by a cytochrome P450 enzyme, said method comprising the steps of:

(a) contacting a set of compounds, according to the first aspect of the invention in which Effector is a fluorophore, with said cytochrome P450 enzyme and determining if said contact results in release of said fluorophore from one or more compounds of said set;

(b) contacting said set of compounds with a control tissue, tissue or cell extract, or enzyme and determining if said contact results in release of said fluorophore from one or more compounds of said set; and (c) identifying said compound specifically activated by said cytochrome P450 as any compound in said set of compounds that releases said fluorophore in step (a) but not, or only to a much lesser extent, in step (b).

Viewed from an eighth aspect, the invention provides a method for determining whether a compound of the invention, wherein Effector is a molecule having a pharmacological function, is efficacious in treating cancer, said method comprising administering said compound to an animal having cancer, wherein said cancer is resultant from implantation of either a recombinant cell modified so as to express constitutively a cytochrome P450 enzyme, a tissue taken directly from a tumor or a cancer, or a cell from an early passage cell line derived from a tissue taken directly from a tumor or a cancer that expresses said cytochrome P450 enzyme at levels similar to those from the tumor or cancer from which it originates.

Additional embodiments of the present method, compounds, and the like will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention.

Further aspects and embodiment of the invention will follow from the discussion that follows below.

DETAILED DESCRIPTION

Figure 1:
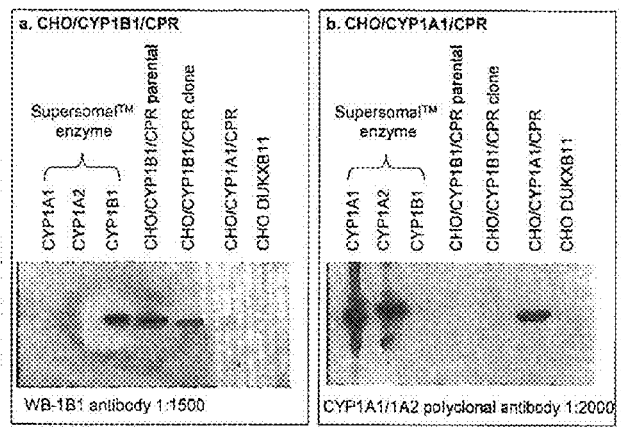
FIG. 1 depicts Western blots showing the detection of CYP1B1 expression in a transfected CHO/CYP1B1/CPR cell line (panel A) and CYP1A1 expression in a transfected CHO/CYP1A1/CPR cell line (panel B). Details are provided in the experimental section below.

The present invention arises from the provision of prodrugs in which a so-called Effector molecule, which may be a cytostatic, cytotoxic, diagnostic or screening molecule as described in greater detail hereinafter, is chemically modified by reacting it whereby to form a compound of formula (I). We have found that hydroxylation of compounds of formula (I), in particular CYP1B1-induced hydroxylation, allows release of the Effector molecules by a collapse of the compounds of formula (I) which happens spontaneously upon direct hydroxylation or hydroxylation via epoxide formation.

In overview, the structure of the compounds of formula (I) may be considered to comprise three parts: a trigger region, a linker and an Effector molecule. The trigger serves as a substrate for the typically CYP1B1-induced hydroxylation and may be generally understood to comprise the bicyclic moiety depicted on the left hand side of formula (I) and the substituents thereof, i.e. comprising that part of the compounds containing $Y^1$-$Y^5$, $Z^1$-$Z^6$ and the remaining carbon atoms to which some of these moieties are attached. The trigger region of the compounds is attached through a linking region comprising the $C(Z^7)$—$X^1$—$X^2$ unit to the Effector molecule which is labelled as such.

The make-up and variability of these three regions—the trigger, linker and Effector regions—of the compounds of formula (I) are now described.

In the discussion that follows, reference is made to a number of terms, which are to be understood to have the meaning provided, below, unless the context dictates to the contrary.

By alkyl is meant herein a saturated hydrocarbyl radical, which may be straight-chain, cyclic or branched (typically straight-chain unless the context dictates to the contrary). Where an alkyl group has one or more sites of unsaturation, these may be constituted by carbon-carbon double bonds or carbon-carbon triple bonds. Where an alkyl group comprises a carbon-carbon double bond this provides an alkenyl group; the presence of a carbon-carbon triple bond provides an alkynyl group. Typically alkyl, alkenyl and alkynyl groups will comprise from 1 to 25 carbon atoms, more usually 1 to 10 carbon atoms, more usually still 1 to 6 carbon atoms it being of course understood that the lower limit in alkenyl and alkynyl groups is 2 carbon atoms and in cycloalkyl groups 3 carbon atoms.

Alkyl, alkenyl or alkynyl groups may be substituted, for example once, twice, or three times, e.g. once, i.e. formally replacing one or more hydrogen atoms of the alkyl group. Examples of such substituents are halo (e.g. fluoro, chloro, bromo and iodo), aryl hydroxy, nitro, amino, alkoxy, alkylthio, carboxy, cyano, thio, formyl, ester, acyl, thioacyl, amido, sulfonamido, carbamate and the like.

By carboxy is meant herein the functional group $CO_2H$, which may be in deprotonated form ($CO_2^-$).

Halo is fluoro, bromo, chloro or iodo.

By acyl and thioacyl are meant the functional groups of formulae —C(O)-alkyl or —C(S)-alkyl respectively, where alkyl is as defined hereinbefore.

By ester is meant a functional group comprising the moiety —OC(=O)—.

By amido is meant a functional group comprising the moiety —N(H)C(=O)—; by carbamate is meant a functional group comprising the moiety —N(H)C(=O)O—; and by sulfonamido is meant a functional group comprising the moiety —$SO_2$N(H)$_2$—, in which each hydrogen atom depicted may be replaced (independently in sulfonamido) with alkyl or aryl.

Alkyloxy (synonymous with alkoxy) and alkylthio moieties are of the formulae —O-alkyl and —S-alkyl respectively, where alkyl is as defined hereinbefore.

Likewise alkenyloxy, alkynyloxy, alkenylthio and alkynylthio are of the formulae —Oalkenyl, —Oalkynyl, —Salkenyl and Salkynyl, where alkenyl and alkynyl are as defined hereinbefore.

By amino group is meant herein a group of the formula —N(R)$_2$ in which each R is independently hydrogen, alkyl or aryl, e.g. an unsaturated, unsubstituted $C_{1-6}$ alkyl such as methyl or ethyl, or in which the two Rs attached to the nitrogen atom N are connected. One example of this is whereby —R—R— forms an alkylene diradical, derived formally from an alkane from which two hydrogen atoms have been abstracted, typically from terminal carbon atoms, whereby to form a ring together with the nitrogen atom of the amine. As is known the diradical in cyclic amines need not necessarily be alkylene: morpholine (in which —R—R— is —(CH$_2$)$_2$O(CH$_2$)$_2$—) is one such example from which a cyclic amino substituent may be prepared.

References to amino herein are also to be understood as embracing within their ambit quaternised or protonated derivatives of the amines resultant from compounds comprising such amino groups. Examples of the latter may be understood to be salts such as hydrochloride salts.

By aryl is meant herein a radical formed formally by abstraction of a hydrogen atom from an aromatic compound.

Arylene diradicals are derived from aromatic moieties, formally, by abstraction of two hydrogen atoms, and may be and typically are, unless the context specifically dictates to the contrary, monocyclic, for example, phenylene. As known to those skilled in the art, heretoaromatic moieties are a subset of aromatic moieties that comprise one or more heteroatoms, typically O, N or S, in place of one or more carbon atoms and any hydrogen atoms attached thereto. Exemplary heteroaromatic moieties, for example, include pyridine, furan, pyrrole and pyrimidine. Further examples of heteroaromatic rings include pyrdidyl, pyridazine (in which 2 nitrogen atoms are adjacent in an aromatic 6-membered ring); pyrazine (in which 2 nitrogens are 1,4-disposed in a 6-membered aromatic ring); pyrimidine (in which 2 nitrogen atoms are 1,3-disposed in a 6-membered aromatic ring); or 1,3,5-triazine (in which 3 nitrogen atoms are 1,3,5-disposed in a 6-membered aromatic ring).

Aryl or arylene radicals may be substituted one or more times with an electron-withdrawing group (for example a group selected from halo, cyano (—CN), haloalkyl, amide, nitro, keto (—COR), alkenyl, alkynyl, quarternary amino (—N$^+$R$_3$), ester, amido (—CONR$_2$), N-connected amido (—NR—C(=O)—R), N-connected sulfonamido (—NR—S(=O)$_2$R), sulfoxy (—S(=O)$_2$OH), sulfonate (S(=O)$_2$OR), sulfonyl (S(=O)$_2$R) and sulfonamide (—S(=O)$_2$—NR$_2$), where (each) R is independently selected from a $C_1$-$C_6$ alkyl group), a $C_3$-$C_{20}$ heterocyclic group, or a $C_3$-$C_{20}$ aryl group, typically a $C_1$-$C_6$ alkyl group, unsubstituted $C_1$-$C_6$ alkoxy, and substituted $C_1$-$C_6$ alkoxy where the substituted alkyl or alkoxy are substituted with one or more groups selected from ether, amino, mono- or di-substituted amino, cyclic $C_1$-$C_5$ alkylamino, imidazolyl, $C_1$-$C_6$ alkylpiperazinyl, morpholino, thiol, thioether, tetrazole, carboxylic acid, ester, amide, mono- or di-substituted amide, N-connected amide (—NR—C(=O)—R), N-connected sulfonamide (—NR—S(=O)$_2$—R), sulfoxy (—S(=O)$_2$OH), sulfonate (S(=O)$_2$OR), sulfonyl (S(=O)$_2$R), sulfoxy (S(=O)OH), sulfinate (S(=O)OR), sulfinyl (S(=O)R), phosphonooxy(—OP(=O)(OH)$_2$), phosphate (OP(=O)(OR)$_2$), and sulfonamide (—S(=O)$_2$—NR$_2$), where in (each) R is independently selected from a $C_1$-$C_6$ alkyl group, a $C_3$-$C_{20}$ heterocyclic group, or a $C_3$-$C_{20}$ aryl group.

The trigger region of the compounds of formula (I) generally comprises a bicyclic moiety comprising an aromatic ring (that comprises the $Y^2$ and $Y^3$ moieties as indicated) fused to a second ring (that comprises the $Y^1$, $Y^4$ and $Y^5$ moieties that may be aromatic or non-aromatic.

Figure 2A:
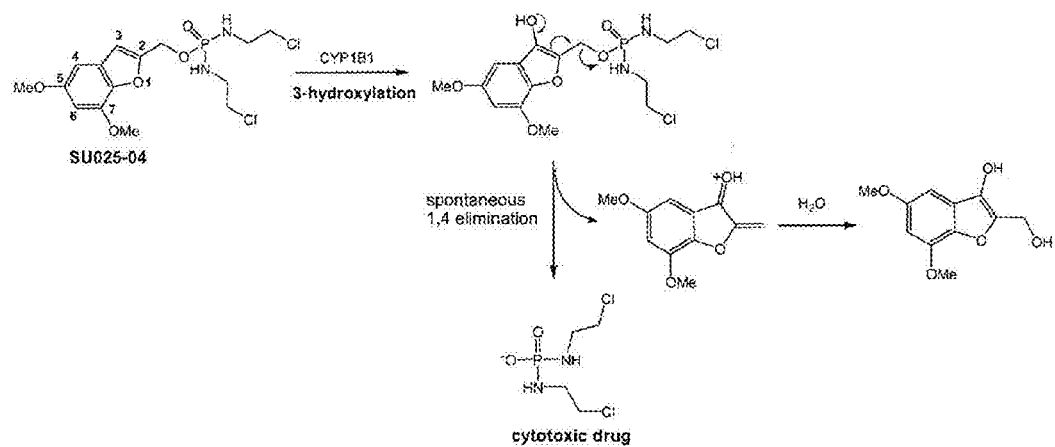
FIG. 2a shows a mechanism for CYP1B1-induced 3-hydroxylation of a compound of the invention (referred to herein as SU025-04) followed by spontaneous release of a cytotoxic Effector molecule (N,N'-bis(2-chloroethyl)phosphorodiamidate (also known as IPM chloride) by 1,4 elimination.
Figure 2B:
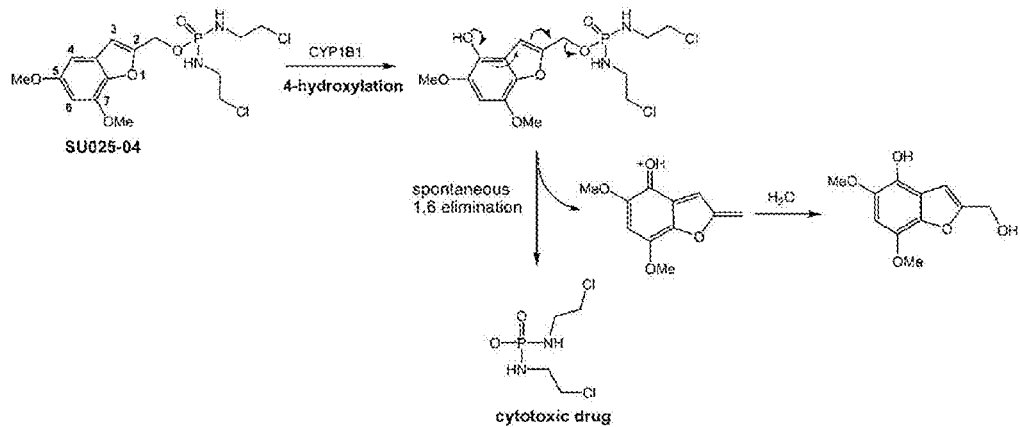
FIG. 2b shows a mechanism for CYP1B1-induced 4-hydroxylation of a compound of the invention (referred to herein as SU025-04) followed by spontaneous release of a cytotoxic Effector molecule (N,N'-bis(2-chloroethyl)phosphordiamidate (also known as IPM chloride) by 1,6 elimination.
Figure 2C:
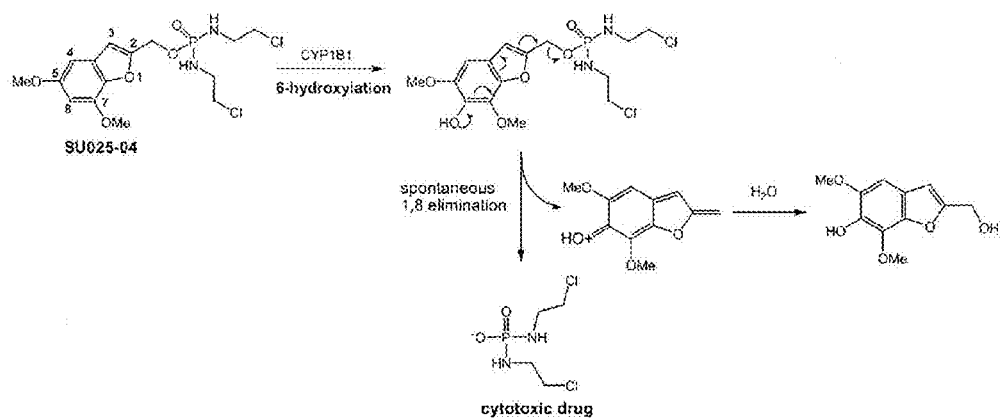
FIG. 2c shows a mechanism for CYP1B1-induced 6-hydroxylation of a compound of the invention (referred to herein as SU025-04) followed by spontaneous release of a cytotoxic Effector molecule (N,N'-bis(2-chloroethyl)phosphordiamidate (also known as IPM chloride) by 1,8 elimination.
Figure 3:
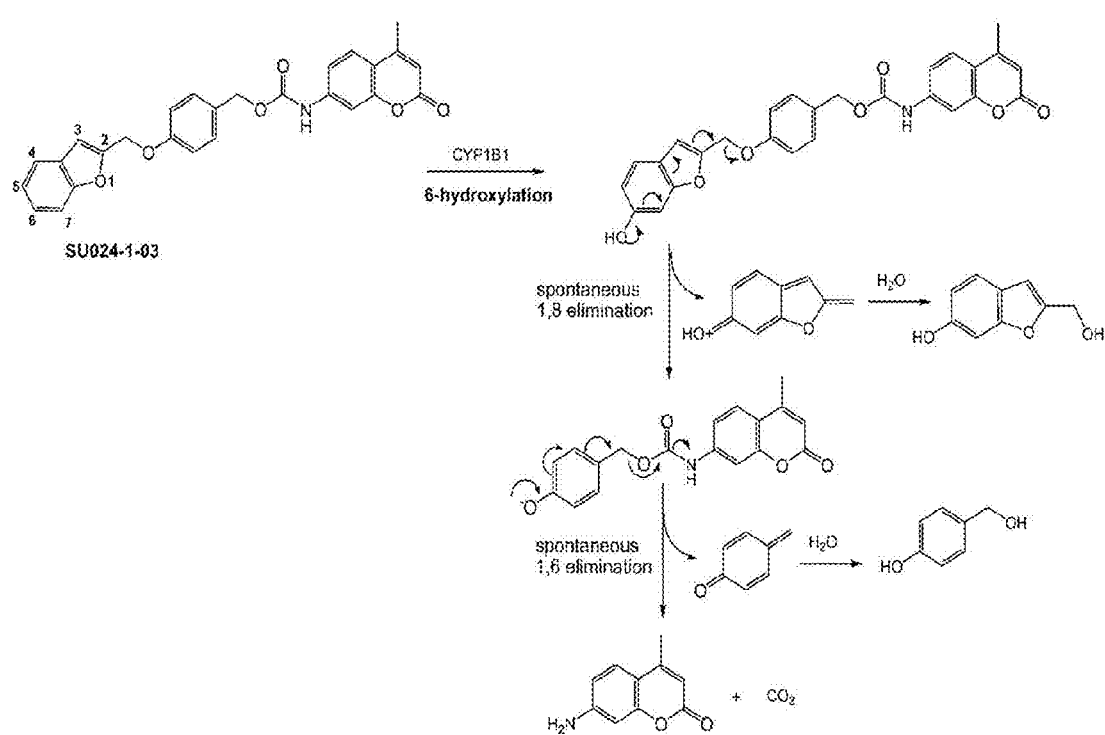
FIG. 3 shows a mechanism for CYP1B1-induced 6-hydroxylation of a compound of the invention (referred to herein as SU024-1-03) followed by spontaneous release of an Effector molecule by 1,8 elimination.

Without being bound by theory, it is believed that the activity of the compounds of formula (I) as substrates for hydroxylation, e.g. effected by CYP1B1, is achieved in part by the structure of the trigger moiety being susceptible to hydroxylation when $Z^2$ or $Z^4$ is hydrogen, or when $Y^1$—$Z^1$ is C—H, the hydroxylation thus taking place at one of the three carbon atoms of those to which $Z^2$ and $Z^4$ are connected, and $Y^1$, where $Y^1$ is carbon. As is depicted in FIG. 2, hydroxylation at any of these positions in a representative compound of the invention, labelled SU025-04, leads to spontaneous collapse of the compound by an elimination process, either a 1,4-, a 1,6- or a 1,8-elimination, depending upon at which of these positions hydroxylation takes place.

It will be noted from the structure of the compounds of formula (I) that, by virtue of the conjugation of carbon atoms to which $Z^2$ and $Z^4$ are attached through $Y^1$ to the linker moiety, that any of the three mechanisms for spontaneous breakdown of the compound may take place independently of the nature of the $Z^6$—$Y^4$—$Y^5$ region of the compounds. Thus a wide variety to the nature of this region of the compounds of formula (I) may be tolerated as discussed below. Also, continuation of the region of conjugation is achieved inter alia by the use of the conjugated $X^1$ moieties described herein.

In the compounds of formula (I), each of the atoms indicated by $Y^1$, $Y^2$ and $Y^3$ may independently be a carbon atom or a nitrogen atom. Where the atom concerned is a nitrogen atom, the respective substituent ($Z^1$, $Z^3$ or $Z^5$ respectively) will be absent. In certain embodiments of the invention $Y^2$ or $Y^3$ is a carbon atom. In particular embodiments of the invention both $Y^2$ and $Y^3$ are carbon atoms. According to either of these embodiments—that in which both $Y^2$ or $Y^3$ is a carbon atom or in which $Y^2$ and $Y^3$ are carbon atoms—or in which neither $Y^2$ or $Y^3$ is a carbon atom, $Y^1$ may be a carbon atom.

The substituents $Z^1$, $Z^2$ and $Z^4$ may be generally as described in claim 1. However, at least one of these moieties is a hydrogen atom so as to allow a site for hydroxylation of the compound. In some embodiments of the invention either $Z^2$ or $Z^4$ is hydrogen. In other embodiments $Z^2$ and $Z^4$ is hydrogen. In either of these embodiments—that in which $Z^2$ or $Z^4$ is a hydrogen atom or in which both $Z^2$ and $Z^4$ are hydrogen atoms—or in which neither $Z^2$ or $Z^4$ is a hydrogen atom, $Z^1$ may be hydrogen. In certain embodiments of the invention each of $Z^1$, $Z^2$ and $Z^4$ is a hydrogen atom.

Either $Z^3$ or $Z^4$ may, together with the adjacent substituent on the aromatic ring (i.e. $Z^2$ or $Z^4$, or $Z^3$ or $Z^5$ respectively) may, together with the atoms of the aromatic ring to which these substituents are connected form an aromatic ring fused to the remainder of the compound. Thus, $Z^2$ and $Z^3$, together with the carbon atom to which $Z^2$ is connected, and $Y^2$, may form an aromatic ring. Similarly, for example, $Z^4$, $Z^5$ and the carbon atom to which $Z^4$ is connected, and $Y^3$, may together form an aromatic ring.

In certain embodiments of the invention, none or only two of the pairs of substituents $Z^2$ & $Z^3$, $Z^3$ & $Z^4$ and $Z^4$ & $Z^5$ together form a fused aromatic ring. Thus, in certain embodiments there are no aromatic rings fused to the aromatic ring comprising $Y^2$ & $Y^3$.

Specifically, substituents $Z^3$ and $Z^5$ are typically not part of an aromatic ring fused to the remainder of the compound of formula (I). Where this is the case, i.e. where these moieties are individual substituents, $Z^3$ may be alkyl, alkenyl, alkynyl, aryl, aralkyl, alkyloxy, alkenyloxy, alkynyloxy, aryloxy, aralkyloxy, alkylthioxy, alkenylthioxy, alkynylthioxy, arylthioxy, aralkylthioxy, amino, hydroxy, thio, halo, carboxy, formyl, nitro and cyano and $Z^5$ may be alkyl, alkenyl, alkynyl, aryl, aralkyl, alkyloxy, alkenyloxy, alkynyloxy, aryloxy, aralkyloxy, alkylthioxy, alkenylthioxy, alkynylthioxy, arylthioxy, aralkylthioxy, amino, hydroxy, thio, carboxy, formyl, nitro and cyano. In certain embodiments of the invention, $Z^3$ may be alkyl, alkenyl, alkynyl, aryl, aralkyl, alkyloxy, alkenyloxy, alkynyloxy, aryloxy, aralkyloxy, alkylthioxy, alkenylthioxy, alkynylthioxy, arylthioxy, aralkylthioxy, amino, hydroxy, thio, halo, carboxy, formyl, nitro and cyano.

In certain embodiments of the invention, $Z^3$ and $Z^5$ are individual substituents other than hydrogen atoms. Where $Z^3$ and $Z^5$ are the same substituent or otherwise, $Z^3$ and $Z^5$ according to certain embodiments of the invention are electron-donating groups such as alkoxy, alkylthioxy, aryloxy, arylthioxy. In particular embodiments of the invention, $Z^3$ or $Z^5$ are both amino or alkoxy, for example, $C_1$-$C_6$ alkoxy. Examples of such alkoxy groups include methoxy, ethoxy, isopropoxy, n-propoxy and the like. In certain embodiments of the invention either $Z^3$ or $Z^5$, or $Z^3$ and $Z^5$, are methoxy. In certain embodiments of this invention $Z^3$ and $Z^5$ are the same and are any of the immediately aforementioned substituents, or classes of substituent. As noted above, the compounds of formula (I) may be varied significantly in their structure in the portion that comprises $Z^6$—$Y^4$—$Y^5$. Thus $Y^4$ may be oxygen, sulfur, sulfoxide or sulfone whereupon there is no $Z^6$ substituent present (p=0), nitrogen (wherein p=0 or 1) or a carbon atom whereupon p=1 or 2. In certain embodiments of the invention p=0 and $Y^4$ is oxygen, sulfur, sulfone or sulfoxide. In particular embodiments of the invention p=0 and $Y^4$ is oxygen or sulfur. In certain embodiments of the invention p=0 and $Y^4$ is oxygen.

—$Y^5$— may be one of (i) a single bond, in which case the trigger moiety is based upon the 6-membered aromatic $Y^2$- and $Y^3$-containing ring fused to a 5-membered ring since in this embodiment $Y^5$ is effectively absent; or (ii) =CH— in which the double bond = is connected to $Y^4$. In these embodiments of the invention the trigger moiety is thus made up of two fused aromatic rings and the skilled person will appreciate that, where —$Y^5$— is =CH— then $Y^4$ is either a nitrogen atom and p=0 or a carbon atom and p=1. Finally, —$Y^5$— may be (iii) —$CH_2$— or —$CH_2CH_2$— in which case the trigger moiety comprises a bicyclic system comprising a 6- or 7-membered ring fused to the aromatic 6-membered ring substituted with $Y^2$ and $Y^3$. In certain embodiments of the invention the or one or more of hydrogen or the hydrogen atoms specified in options (ii) and (iii) for —$Y^5$— may be replaced with a $Z^{11}$ moiety, for example an alkyl or halo moiety. In certain embodiments of the invention no $Z^{11}$ is present. In particular embodiments of the invention —$Y^5$— is a single bond, for example wherein p=0 and $Y^4$ is oxygen, sulfur, sulfone or sulfoxide, p=0 and $Y^4$ is oxygen or sulfur and in particular wherein p=0 and $Y^4$ is oxygen.

The linking moiety $CH(Z^7)$—$X^1$—$X^2$ is now described.

$Z^7$ is hydrogen or an alkyl or aryl group, which, in certain embodiments of the invention is unsubstituted. In certain embodiments of the invention, the or each $Z^7$ is an alkyl group, e.g. an unsubstituted alkyl group such as an unsubstituted $C_1$-$C_6$ alkyl group. Examples of $Z^7$ moieties include methyl and ethyl. In particular embodiments of the invention $Z^7$=hydrogen such that —$CH(Z^7)$— is methylene. In other embodiments the or each $Z^7$ moiety is a substituted alkyl group, e.g. a substituted methyl or ethyl group. Examples of such embodiments include amino-substituted alkyl groups, e.g. morpholino or piperidinyl alkyl groups, or other groups that confer enhanced water solubility. Alternatively the, each, or at least one $Z^7$ may be an optionally substituted heteroaryl moiety such as pyridyl.

$X^1$ may be a variety of linking atoms or divalent linking moieties, for example, $X^1$ may be oxygen, sulfur, sulfonamide or sulfonate ester. In addition, $X^1$ may be ethane-1,2-diylbis(methylcarbamate) or a conjugated alkenemethyloxy moiety.

By a conjugated alkenemethyloxy moiety is meant a moiety of the formula $(=\!CH\!-\!CH)_q\!=\!CH\!-\!CH_2\!-\!O\!-\!$ wherein q is an integer from 0 to 6, for example from 0 to 3, e.g. 0 or 1. The skilled person will understand that the oxygen atom depicted in the alkenemethyloxy moieties may be substituted with a sulfur atom $SO_2\!-\!O$ or $SO_2NZ^{10}$ moiety, whereby to provide conjugated alkenemethyl sulfonate or conjugated alkenemethyl sulfonamide moieties as recited hereinbefore in which the oxygen or sulfur atoms, or sulfonate of sulfonamide moieties ($SO_2\!-\!O$ and $SO_2\!-\!NZ^{10}$) are attached to $X^2$ or, if this is absent, Effector.

According to certain embodiments of the invention $X^1$ is oxygen or sulfur. In many embodiments of the invention $X^1$ is oxygen.

$X^2$ is an optional additional linking moiety, which is either absent or interposed between $X^1$ and the Effector moiety.

$X^2$ may be comprised of a variety of moieties as described herein or may be absent. In certain embodiments of the invention $X^2$ is absent or $X^1$—$X^2$-Effector is one of

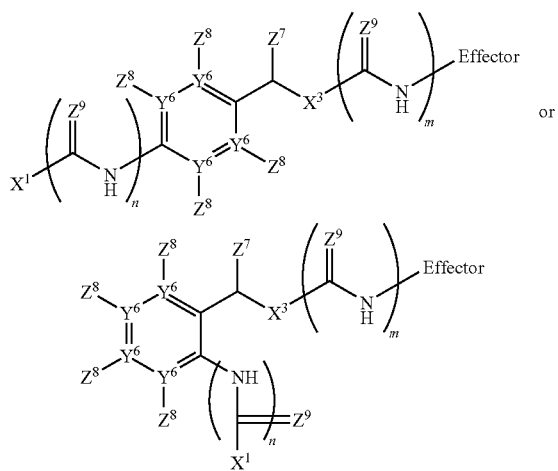

For example, $X^2$ may comprise an arylene-CH($Z^7$)$X^3$ moiety (hereinafter —ArCH($Z^7$)$X^3$— moiety) and/or an amide moiety. Where present, the —Ar—CH($Z^7$)$X^3$— moiety may be flanked by one or two amide or thioamide groups (C($Z^9$) NH). If flanked by one amide or thioamide group, this may be disposed directly between the $X^1$ moiety and the aromatic ring of the —Ar—CH($Z^7$)$X^3$ (wherein n=1) moiety or interposed between $X^3$ and the Effector moiety (wherein m=1). Alternatively, an amide or thioamide group may be present in both or neither of these positions. In certain embodiments of the invention n=0 and m=1. When $X^2$ comprises a —Ar—CH ($Z^7$)$X^3$— moiety, whether or not this is flanked by one or two amide or thioamide moieties, the $X^1$ moiety that is attached to the aromatic ring either directly or indirectly through an amide or thioamide moiety may be attached at either of the two positions in the aromatic ring that are ortho to the CH($Z^7$) $X^3$ moiety of the —Ar—CH($Z^7$)$X^3$ system or at the para position. Engineering these points of attachment in the aromatic rings of the $X^2$ moieties that comprise Ar—CH($Z^7$) $X^3$— moieties permits 1,4-, 1,6- or 1,8-elimination of the Effector molecule. It will be understood that the arylene group present in certain embodiments of $X^2$ may be heteroaromatic, that is to say one or two or atoms $Y^6$ may be nitrogen atoms with the remainder being carbon atoms. An example of such a heteroarylene moiety is pyridylene, in which one $Y^6$ is a nitrogen atom. In many embodiments of the invention each $Y^6$ where present is a carbon atom.

When an arylene group is present in the $X^2$ moiety this may be substituted as indicated at any of the four positions (not connecting the arylene group to the Effector and trigger termini of the compounds of formula (I) that is) by substituents $Z^8$ which may be selected independently as defined in claim 1.

Where $X^2$ comprises one or more amide or thioamide moieties —CH($Z^9$)NH this is typically, where present, (each) $Z^9$ is oxygen whereby to provide one or more amide moieties although, where more than one $Z^9$ is present, each $Z^9$ may be selected independently.

Finally, the Effector part of the compounds of formula (I) is the moiety which provides the desired targeted effect in cells, typically those in which CYP1B1 is expressed. The Effector component may be any molecule having a pharmacological diagnostic or screening function when released from the compound of formula (I). By pharmacological or diagnostic function is meant that the effector component, when released, has a discernable pharmacological or diagnostic effect on the cells in which it is released.

It will be understood by those skilled in the art that the Effector component (Effector) in the compounds of formula (I) when released may comprise an atom described herein as part of $X^1$— e.g. as oxygen or sulfur atom, or part of $X^2$, e.g. $X^3$, e.g. an oxygen or sulfur atom. However, it is to be understood that the distinctions between the trigger, linker and Effector portions of the compounds of formula (I) are made simply to assist in the description of the compounds of the invention; the skilled person will be aware that the Effector portion in the compounds of the invention constitutes the bulk of the Effector molecule that is released upon hydroxylation-induced breakdown but that one or some of the atoms in the Effector molecule that is released may be provided by atoms described herein as being $X^1$, part of $X^1$ or $X^2$ and indeed elsewhere (e.g. hydrogen atoms picked up from water molecules). Alternatively the Effector molecule may be attached to the remainder of the compounds of formula (I) through keto or formyl groups for example.

The Effector molecule, where this has a pharmacological effect, may be, for example, any chemical that has a cytostatic or cytotoxic effect upon the cell that serves to effect its release is expressed (e.g. CYP1B1—expressing cells). As is known, a cytotoxic molecule is a molecule that is toxic to cells whereas a cytostatic agent is one that suppresses the growth and/or replication of cells.

In certain embodiments of the invention the Effector molecule is a cytotoxic agent. Examples of cytotoxic agents that may be used include but are not limited to alkylating agents, antimitotic agents, antifolates, antimetabolites, DNA-damaging agents and enzyme inhibitors (e.g tyrosine kinase inhibitors). Specific examples of possible cytotoxic drug moieties include but are not limited to bis(haloethyl)phosphoroamidates, cyclophosphamides, gemcitabine, cytarabine, 5-fluorouracil, 6-mercaptopurine, camptothecin, topotecan, doxorubicin, daunorubicin duocarmycin, etoposide, duetoposide, combretastatin A-4, vinblastine, vincristine, AQ4N, hydroxyurea, maytansines, enediyenes, epothilones, taxanes, bleomycins, calicheamicins, colchicine, dacarbazine, dactinomycin, epirubicin, epirubicin derivatives, fludarabine, hydroxyureapentatostatin, methotraxate, mitomycin, mitoxantrone, carboplatin, cisplatin, taxels, 6-thioguanine, vinca alkaloids, platinum coordination complexes, anthracenediones, substituted ureas, methyl hydrazine derivatives, and nitrogen mustards.

In certain embodiments of the invention, the Effector molecule is a phosphoramide mustard, that is to say a phosphoric acid derivative in which one or two, typically two, of the hydroxyl groups of phosphoric acid are exchanged for a nitrogen mustard, or an oxygen- or sulfur-containing analogue thereof, and optionally the P(=O) replaced with P(=S). A nitrogen mustard herein is defined as a non-specifically alkylating amine, structurally related to mustard gas (1,5-dichloro-3-thiapentane), in which the sulfur atom is replaced with a nitrogen atom and, optionally, one chlorethyl side chain is replaced by a hydrogen atom or alkyl group, or one or both terminal chloro substituents are replaced by a leaving group such as bromo, iodo or mesylate (—OSO$_2$CH$_3$). Examples of phosphoramide mustards include the compounds known as phosphoramide mustard (PM) and isophosphoramide mustard (IPM):

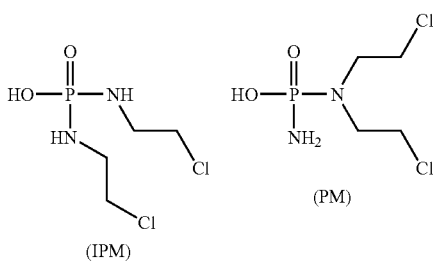

Thus, it will be noted that the compound PM is an example, as well as the name of the class, of compounds known as phosphoramide mustards since it may be regarded as a derivative of phosphoric acid in which one of the hydroxyl groups has been exchanged for a nitrogen mustard (the other hydroxyl group being exchanged for an amino group (NH$_2$)).

In those embodiments of the invention in which the Effector molecule is a phosphoramide mustard, in which one or two, typically two, of the hydroxyl groups of phosphoric acid derivative are exchanged for an oxygen- or sulfur-containing analogue of a of nitrogen mustard, by this is meant analogues of phosphoramide mustards in which the nitrogen mustard is replaced with an analogue in which one chloroethyl arm is absent and the nitrogen atom exchanged for a sulfur or an oxygen atom.

In a particular embodiment of the present invention the Effector molecule is connected to the remainder of the compound through an oxygen or sulfur atom and -Effector is of formula (II):

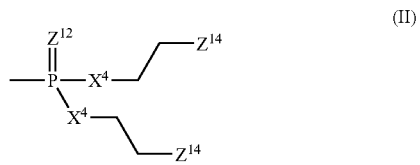

(wherein:
$Z^{12}$ is oxygen or sulfur;
each $X^4$ is independently oxygen, sulfur or $NZ^{13}$ wherein each —$Z^{13}$ is independently —(CH$_2$)$_2$—$Z^{14}$, -alkyl or -hydrogen; and each $Z^{14}$ is independently chloro, bromo, iodo, or mesylate).

In certain embodiments of the invention, $Z^{12}$ is oxygen. In these and other specific embodiments, each $X^4$ is the same. In these and other specific embodiments, each $X^4$ is $NZ^{13}$. In these and other specific embodiments, each $Z^{13}$ is hydrogen. In these and other specific embodiments of the invention, each $Z^{14}$ is the same and/or is bromo or chloro. In particular embodiments of the invention, each $Z^{14}$ present (which may be two, three or four $Z^{14}$ moieties) is bromo.

Alternatively, the Effector molecule may be one that fulfils a diagnostic function, for example allowing identification, or a fuller understanding of the nature, of a tumor in which, for example, CYP1B1 is expressed. An example of a class of Effector molecules that are diagnostic molecules are fluorophoric molecules. These may be useful in the diagnosis of cancerous cells. Examples of fluorophoric compounds include coumarins, resorufins, fluoresceins and rhodamines and it is in fact through a number of experiments conducted on compounds of the invention comprising coumarins as the Effector molecule that the viability of the present invention has been demonstrated (see the examples section below).

It will thus be appreciated that the compounds of formula (I) in which Effector fulfils a diagnostic function may be of use in methods of diagnosis and such methods constitute further aspects of the present invention. Therefore, the invention provides a compound of formula (I), or a pharmaceutically acceptable salt, ester, amide or solvate thereof, for use in a method of diagnosis of a proliferative condition, for example pre-malignant or malignant cellular proliferation, a cancer, a leukaemia, psoriasis, a bone disease, a fibroproliferative disorder or artherosclerosis, for example a proliferative condition selected from bladder, brain, breast, colon, head and neck, kidney, lung, liver, ovarian, prostate and skin cancer, said method comprising administering an amount of a compound, or pharmaceutically acceptable salt, ester, amide or solvate of formula (I) to a subject having or suspected of having such a proliferative and monitoring for the distribution of released Effector molecules in the subject whereby to allow a diagnosis to be made.

Alternatively, the Effector may be one that fulfils a screening function, for example as part of a model prodrug library collection, in order to identify trigger and linker combinations that fragment when activated by CYP1B1 and allelic variants thereof. An example of a class of Effector molecules are fluorophoric molecules. Examples of fluorophoric compounds include the well-known coumarins, resorufins, fluoresceins, and rhodamines. It is in fact through a number of experiments conducted on compounds of the invention comprising coumarins as the Effector molecule that the viability of the present invention has been demonstrated (see Example 1 in the section below). It will thus be appreciated that the compounds of formula (I) in which the effector fulfils a screening function may be of use in identifying trigger and linker combinations for the design and synthesis of prodrugs activated by CYP1B1 and such methods constitute further aspects of the present invention.

It can be thus appreciated that compounds of formula (I) in which an effector fulfils a screening function as part of a model prodrug library collection can be used in combination with cytochrome P450 substrate prediction models to guide the design and synthesis of prodrugs with selectivity for the example CYP1B1, and allelic variants thereof such as CYP1B1*3. For the purpose of clarity, the combination of the model prodrug library with the substrate prediction model links substrate specificity to prodrug activation and fragmentation by CYP1B1, which is a fundamental design principle.

Furthermore, it can be thus appreciated that compounds of formula (I) in which the effector fulfils a screening function can be used in combination with cytochrome P450 substrate prediction models to guide the design and synthesis of prodrugs which are not activated by normal tissue cytochrome P450s exemplified by CYP1A1, CYP1A2, CYP2C9, CYP2C19, CYP2D6, and CYP3A4. An example of a substrate prediction model is the Gaussian Kernel weighted k-NN algorithm based on Tanimoto similarity searches on, but not limited to, descriptors such as extended connectivity fingerprints. Cytochrome P450 substrate prediction models for prodrug design can be built on bioactivity databases derived from cytochrome P450 HTS from structurally diverse compound collections. It is in fact through a number of experiments conducted on compounds of the invention comprising coumarins as the effector molecule used in combination with a CYP1B1 substrate prediction model that the viability of the present invention has been demonstrated (see the Examples 1 and 2).

Alternatively, the Effector may be one that fulfils a screening function as part of a model prodrug library collection in order to identify trigger and linker combinations that fragment when activated by CYP1B1 and/or other cytochrome P450s and allelic variants thereof over-expressed in cancer and other proliferative conditions. An example of a class of Effector molecules are fluorophoric molecules. Examples of fluorophoric compounds include coumarins, resorufins, fluoresceins and rhodamines. Examples of cytochrome P450s other than CYP1B1 which are over-expressed in cancer include CYP2A/2B, CYP2F1, CYP2R1, CYP2S1, CYP2U1, CYP2W1, CYP3A5, CYP3A7, CYP4Z1, CYP26A1, and CYP51.

It can be thus appreciated that compounds of formula (I) in which an effector fulfils a screening function as part of a model prodrug library collection can be used in combination with cytochrome P450 substrate prediction models to guide the design and synthesis of prodrugs with selectivity for CYP1B1 and/or other cytochrome P450s and allelic variants thereof over-expressed in cancer and other proliferative conditions. An example of a class of Effector molecules are fluorophoric molecules. Examples of fluorophoric compounds include coumarins, resorufins, fluoresceins and rhodamines. Examples of cytochrome P450s other than CYP1B1 which are over-expressed in cancer include CYP2A/2B, CYP2F1, CYP2R1, CYP2S1, CYP2U1, CYP2W1, CYP3A5, CYP3A7, $CYP4Z^1$, CYP26A1, and CYP51. An example of a substrate prediction model is the Gaussian Kernel weighted k-NN algorithm based on Tanimoto similarity searches on, but not limited to, descriptors such as extended connectivity fingerprints. Cytochrome P450 substrate prediction models for prodrug design can be built on bioactivity databases derived from cytochrome P450 HTS from structurally diverse compound collections.

According to the aspects and embodiments of the present invention whereby the Effector fulfils a screening function, for example according to the seventh aspect of the invention, a set of compounds will typically comprise a plurality of compounds, for example comprising at least 10, for example at least 20 compounds. In certain embodiments, the set may comprise up to 100, 1000, 10,000 or even 100,000 compounds. Such sets of compounds, i.e. pluralities of compounds according to the first aspect of the invention wherein the Effector is a fluorophore, as well as other pluralities of compounds in which the Effector is not so limited and/or the compounds may be pharmaceutically acceptable salts, esters, amides or solvates, constitute a still further aspect of the present invention.

According to embodiments of the seventh aspect of this invention, where a compound releases the fluorophore in step (a) but not, or only to a much lesser extent, in step (b), by this is meant that the P450 enzyme typically releases at least 10-fold, e.g. at least 20-fold, more of said fluorophore in step (a) as compared to step (b).

Where screening, e.g. according to embodiments of the seventh aspect of this invention yields a hit, e.g. and typically a compound that releases the fluorophore in step (a) but not, or only to a much lesser extent, in step (b), the method of the seventh aspect of the invention optionally includes additional the steps of:

(d) modeling compounds identical in structure to those identified in step (c) except that the fluorophore is replaced with a molecule having a pharmacologic function for binding to an active site of said cytochrome P450 enzyme; and (e) synthesizing compounds modeled in step (d) that are predicted to be substrates for said cytochrome P450 enzyme.

Alternatively, these steps ((d) and (e)) may be practiced independently to the mandatory steps of the seventh aspect of this invention (i.e. (a)-(c)) and so constitute a still further embodiment of the present invention.

Typically the cytochrome P450 enzyme is selected from the group consisting of CYP1B1, CYP2S1, CYP2W1, $CYP4Z^1$ and allelic variants thereof, for example CYP1B1 and allelic variants thereof, e.g. CYP1B1.

An aspect of the present invention is the use of primary human tumour cell lines of early passage number <20 in vitro derived from resected cancer specimens. The primary head and neck squamous cell carcinoma cell lines UT-SCCs described in Examples 4 and 5 below constitutively express CYP1B1 at the mRNA and protein level and can be transplanted subcutaneously into immune-deficient mice, (for example nude or severe combined immune deficient SCID mice) with high engraftment rates to generate primary human tumour xenografts where the constitive expression of cytochrome P450 protein expression matches that of the originating tumour in the patient. These primary human tumour xenograft models, by maintaining cytochrome P450 mRNA/protein expression similarly to the originating patient tumour can therefore be used to assess the efficacy of a compound of the invention, wherein the Effector moiety is an agent having pharmacologic activity, in treating cancer. Furthermore, in the clinical context these primary human tumour xenograft models can be used to check if responses of a compound of the invention, wherein the Effector moiety is an agent having pharmacologic activity, are correlated with clinical responses and outcomes, indicating usefulness for personalized chemotherapy. The primary human tumour models can also be used to compare the efficacy of a compound of claim 1, wherein the Effector moiety is an agent having pharmacologic activity with standard chemotherapeutic regimens and therefore to identify the most effective regimens for compounds of claim 1 alone or in combination with other chemotherapeutic agents.

Furthermore, as part of this invention it is possible to derive primary human tumour xenografts by directly implanting tumour tissue taken directly resected from patients and implanting subcutaneously into, for example, nude, SCID and nonobese diabetic/servere combined immune deficient (NOD/SCID) mice. It is possible to generate first generation primary human tumour xenografts for a range of different cancers which will retain the histological and genetic characteristics of the originating tumor and as such will constitutively express CYP1B1 mRNA/protein at a level similar to the originating tumour. These primary human tumour xenograft models, by maintaining CYP1B1 mRNA/protein expression similarly to the originating patient tumour can therefore be used to assess the efficacy of a compound of the invention, wherein the Effector moiety is an agent having pharmacologic activity, in treating cancer. Furthermore, in the clinical context these primary human tumour xenograft models can be used to check if responses of a compound of claim 1, wherein the Effector moiety is an agent having pharmacologic activity are correlated with clincial responses and outcomes, indicating usefulness for personalized chemotherapy. The primary human tumour models can also be used to compare the efficacy of a compound of the invention, wherein the Effector moiety is an agent having pharmacologic activity, with standard chemotherapeutic regimens and therefore to identify the most effective regimens for compounds of the invention alone or in combination with other chemotherapeutic agents.

Where according to the eighth aspect of this invention, the cancer is resultant from implantation of a cell from an early passage cell line derived from a tissue taken directly from a tumor or a cancer that expresses said cytochrome P450 enzyme at levels similar to those from the tumor or cancer from which it originates, levels may be considered to be similar if they are within 10% to those from the tumor or cancer from which it originates, for example within 5%.

For use according to the present invention, the compounds or a physiologically acceptable salt, solvate, ester or amide thereof described herein may be presented as a pharmaceutical formulation, comprising the compound or physiologically acceptable salt, ester, amide or other physiologically functional derivative thereof, together with one or more pharmaceutically acceptable carriers therefor and optionally other therapeutic and/or prophylactic ingredients. Any carrier(s) are acceptable in the sense of being compatible with the other ingredients of the formulation and not deleterious to the recipient thereof.

Examples of physiologically acceptable salts of the compounds according to the invention include acid addition salts formed with organic carboxylic acids such as acetic, lactic, tartaric, maleic, citric, pyruvic, oxalic, fumaric, oxaloacetic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

The determination of physiologically acceptable esters or amides, particularly esters is well within the skills of those skilled in the art.

It may be convenient or desirable to prepare, purify, and/or handle a corresponding solvate of the compounds described herein, which may be used in the any one of the uses/methods described. The term solvate is used herein to refer to a complex of solute, such as a compound or salt of the compound, and a solvent. If the solvent is water, the solvate may be termed a hydrate, for example a mono-hydrate, di-hydrate, tri-hydrate etc, depending on the number of water molecules present per molecule of substrate.

It will be appreciated that the compounds of the present invention may exist in various stereoisomeric forms and the compounds of the present invention as hereinbefore defined include all stereoisomeric forms and mixtures thereof, including enantiomers and racemic mixtures. The present invention includes within its scope the use of any such stereoisomeric form or mixture of stereoisomers, including the individual enantiomers of the compounds of formulae (I) or (II) as well as wholly or partially racemic mixtures of such enantiomers.

It will also be understood by those skilled in the art that anticancer prodrugs, such as those described herein, can be targeted towards particular tumours by attachment of a tumour-targeting moiety such as tumour-targeting peptide, for example small peptides identified through the development of phage-displayed peptide libraries. Such peptides or other moieties may assist in the targeting of conjugates that comprise them to a particular cancer, particularly a solid tumour. Accordingly, the provision of such conjugates, i.e. of a compound of the invention conjugated to a tumour-targeting moiety, forms a further aspect of this invention as do compositions, uses and methods described herein that comprise or involve use of such conjugates.

The compounds of the present invention may be prepared using reagents and techniques readily available in the art and/or exemplary methods as described hereinafter. It has been found that compounds of the present invention exhibit cytotoxicity in cells expressing CYP1B1 enzyme, but are substantially non-toxic in normal cells that do not express CYP1B1. Compounds of the invention may also exhibit cytotoxicity in cells expressing CYP1A1 enzyme. In practice, therefore, the compounds of the invention are non-toxic prodrugs that are converted (typically by CYP1B1) into cytotoxic agents.

Suitably, the compounds of the invention have a cytotoxicity $IC_{50}$ value as defined below or less than 10 µM, advantageously less than 5 µM, for example less than 1.0 µM or 0.5 µM.

In some embodiments, the cytotoxicity of a compound of the invention may be measured by incubating the compound at different serial dilutions with cells engineered to express CYP1B1. Suitably, said cells may be Chinese Hamster Ovary (CHO) cells, which may contain recombinant CYP1B1 and cytochrome P-450 reductase (CPR). High levels of functional enzyme when co-expressed with human P-450 reductase may be achieved using dihydrofolate reductase (DHFR) gene amplification. Typically, the engineered cells may be incubated with the compound and, after a suitable period of time (e.g., 96 hours), further incubated (e.g., for 1.5 hours) with a suitable assay reagent to provide an indication of the number of living cells in culture. A suitable assay reagent is MTS (see below) which is bioreduced by cells into a formazan product that is soluble in tissue culture medium. The absorbance of the formazan product can be directly measured at 510 nm, and the quantitative formazan product as measured by the amount of absorbance at 490 nm or 510 nm is directly proportional to the number of living cells in culture. Detailed methods for determining the $IC_{50}$ value of a compound according to the invention are described in Example 3 below.

By way of comparison, the $IC_{50}$ values of the compounds of the invention may also be measured in cells (e.g., Chinese Hamster Ovary cells) that do not contain CYP1B1, for example wild type CHO cells. The compounds of the invention may suitably have a fold selectivity for CYP1B1 expressing cells of at least 200, where the "fold selectivity" is defined as the quotient of the $IC_{50}$ value of a given compound in non-CYP1 expressing cells and the $IC_{50}$ value of the same compound in CYP1B1 expressing cells.

In some embodiments, the cytotoxicity of a compound of the invention may be also measured by incubating the compound at different serial dilutions with primary head and neck tumour cells derived from patients with head and neck squamous cell carcinoma as described in Example 4.

In some embodiments, the in vivo efficacy of a compound of the invention may be measured by implanting primary head and neck squamous cell carcinoma tumour cells which constitutively express CYP1B1 subcutaneously into the flank of a nude mouse to generate primary human tumour xenograft models and measuring the effect of prodrug treatment on tumour growth as described in Example 5.

As such, the present invention also embraces the use of one or more of the compounds of the invention, including the aforementioned pharmaceutically acceptable esters, amides, salts, solvates and prodrugs, for use in the treatment of the human or animal body by therapy, particularly the treatment or prophylaxis of proliferative conditions such, for example, as proliferative disorders or diseases, in humans and non-human animals, including proliferative conditions which are in certain embodiments of the invention characterised by cells that express CYP1B1. More particularly, the invention comprehends the use of one or more of the compounds of the invention for the treatment of cancers characterised in certain embodiments of the invention by CYP1B1 expression.

By "proliferative condition" herein is meant a disease or disorder that is characterised by an unwanted or uncontrolled cellular proliferation of excessive or abnormal cells which is undesired, such as, neoplastic or hyperplastic growth, whether in vitro or in vivo. Examples of proliferative conditions are pre-malignant and malignant cellular proliferation, including malignant neoplasms and tumours, cancers, leukemias, psoriasis, bone diseases, fibroproliferative disorders (e.g., of connective tissues) and atherosclerosis.

Said proliferative condition may be characterised in certain embodiments of the invention by cells that express CYP1B1.

Said proliferative condition may be selected from bladder, brain, breast, colon, head and neck, kidney, lung, liver, ovarian, prostate and skin cancer. In some embodiments, said proliferative condition may comprise a solid tumour.

By "treatment" herein is meant the treatment by therapy, whether of a human or a non-human animal (e.g., in veterinary applications), in which some desired therapeutic effect on the proliferative condition is achieved; for example, the inhibition of the progress of the disorder, including a reduction in the rate of progress, a halt in the rate of progress, amelioration of the disorder or cure of the condition. Treatment as a prophylactic measure is also included. References herein to prevention or prophylaxis herein do not indicate or require complete prevention of a condition; its manifestation may instead be reduced or delayed via prophylaxis or prevention according to the present invention. By a "therapeutically-effective amount" herein is meant an amount of the one or more compounds of the invention or a pharmaceutical formulation comprising such one or more compounds, which is effective for producing such a therapeutic effect, commensurate with a reasonable benefit/risk ratio.

The compounds of the present invention may therefore be used as anticancer agents. By the term "anticancer agent" herein is meant a compound that treats a cancer (i.e., a compound that is useful in the treatment of a cancer). The anticancer effect of the compounds of the invention may arise through one or more mechanisms, including the regulation of cell proliferation, the inhibition of angiogenesis, the inhibition of metastasis, the inhibition of invasion or the promotion of apoptosis.

It will be appreciated that appropriate dosages of the compounds of the invention may vary from patient to patient. Determining the optimal dosage will generally involve the balancing of the level of therapeutic benefit against any risk or deleterious side effects of the treatments of the present invention. The selected dosage level will depend on a variety of factors including the activity of the particular compound, the route of administration, the time of administration, the rate of excretion of the compound, the duration of the treatment, other drugs, compounds or materials used in combination with the age, sex, weight, condition, general health and prior medical history of the patient. The amount of compound(s) and route of administration will ultimately be at the discretion of the physician, although generally the dosage will be to achieve local concentrations at the site of action so as to achieve the desired effect.

Administration in vivo can be effected in one dose, continuously or intermittently throughout the course of treatment. Methods of determining the most effective means and dosage of administration are well known to a person skilled in the art and will vary with the formulation used for therapy, the purpose of the therapy, the target cell being treated, and the subject being treated. Single or multiple administrations can be carried out with the dose level and pattern being selected by the treating physician.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. Methods typically include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersible granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release-controlling matrix, or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds.

Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers, which are sealed after introduction of the formulation until required for use. Alternatively, an active compound may be in powder form that is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microliters, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

It should be understood that in addition to the aforementioned carrier ingredients the pharmaceutical formulations described above may include, an appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Pharmaceutically acceptable carriers are well known to those skilled in the art and include, but are not limited to, 0.1 M and preferably 0.05 M phosphate buffer or 0.8% saline. Additionally, pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

Therapeutic formulations for veterinary use may conveniently be in either powder or liquid concentrate form. In accordance with standard veterinary formulation practice, conventional water-soluble excipients, such as lactose or sucrose, may be incorporated in the powders to improve their physical properties. Thus particularly suitable powders of this invention comprise 50 to 100% w/w and preferably 60 to 80% w/w of the active ingredient(s) and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain the compound or a derivative or salt thereof and may optionally include a veterinarily acceptable water-miscible solvent, for example polyethylene glycol, propylene glycol, glycerol, glycerol formal or such a solvent mixed with up to 30% v/v of ethanol. The liquid concentrates may be administered to the drinking water of animals.

In general, a suitable dose of the one or more compounds of the invention may be in the range of about 1 µg to about 5000 µg/kg body weight of the subject per day, e.g., 1, 5, 10, 25, 50, 100, 250, 1000, 2500 or 5000 µg/kg per day. Where the compound(s) is a salt, solvate, prodrug or the like, the amount administered may be calculated on the basis the parent compound and so the actual weight to be used may be increased proportionately.

In some embodiments, the one or more compounds of the present invention may be used in combination therapies for the treatment of proliferative conditions of the kind described above, i.e., in conjunction with other therapeutic agents. Examples of such other therapeutic agents include but are not limited to topoisomerase inhibitors, alkylating agents, antimetabolites, DNA binders and microtubule inhibitors (tubulin target agents), such as cisplatin, cyclophosphamide, doxorubicin, etoposide, irinotecan, fludarabine, 5FU, taxanes or mitomycin C. Other therapeutic agents will be evident to those skilled in the art. For the case of active compounds combined with other therapies the two or more treatments may be given in individually varying dose schedules and via different routes.

The combination of the agents listed above with a compound of the present invention would be at the discretion of the physician who would select dosages using his common general knowledge and dosing regimens known to a skilled practitioner.

Where a compound of the invention is administered in combination therapy with one, two, three, four or more, preferably one or two, preferably one other therapeutic agents, the compounds can be administered simultaneously or sequentially. When administered sequentially, they can be administered at closely spaced intervals (for example over a period of 5-10 minutes) or at longer intervals (for example 1, 2, 3, 4 or more hours apart, or even longer period apart where required), the precise dosage regimen being commensurate with the properties of the therapeutic agent(s).

The compounds of the invention may also be administered in conjunction with non-chemotherapeutic treatments such as radiotherapy, photodynamic therapy, gene therapy, surgery and controlled diets.

All articles, books, patents, patent publications and other publications referenced herein are incorporated by reference in their entireties. In the event that certain disclosure contained in any such item incorporated herein by reference in its entirety is in conflict with disclosure in the instant application, reliance upon the teachings of the instant disclosure is intended.

The invention is now illustrated with reference to the following non-limiting examples:

EXAMPLES

It is to be understood that while the invention has been described in conjunction with certain preferred specific embodiments thereof, the foregoing description as well as the examples that follow are intended to illustrate and not limit the scope of the invention. Other aspects, advantages and modifications within the scope of the invention will be apparent to those skilled in the art to which the invention pertains.

Preparation of Compounds
General $^1$H, $^{13}$C and $^{31}$P nuclear magnetic resonance (NMR) spectra were recorded in the indicated solvent on either a Bruker Avance DPX 500 MHz or Bruker Avance 300 MHz spectrometer. Chemical shifts are expressed in ppm. Signal splitting patterns are described as singlet (s), broad singlet (bs), doublet (d), triplet (t), quartet (q), multiplet (m) or combination thereof. Low resolution electrospray (ES) mass spectra were recorded on a Bruker MicroTof mass spectrometer, run in a positive ion mode, using either methanol/water (95:5) or water acetonitrile (1:1)+0.1% formic acid as a mobile phase. High resolution electrospray measurements were performed on a Bruker Microtof mass spectrometer. LC-MS analysis were performed with an Agilent HPLC 1100 (Phenomenex Gemini Column 5μ C18 110 Å 50×3.0 mm, eluted with (0 to 20% MeOH/H$_2$O) and a diode array detector in series with a Bruker Microtof mass spectrometer. Column chromatography was performed with silica gel (230-400 mesh) or RediSep®0.4, 12, 40 or 80 g silica prepacked columns. All the starting materials are commercially available and were used without further purification. All reactions were carried out under dry and inert conditions unless otherwise stated. [Compounds indicated below with a parenthetical dagger (†) are not examples of the invention but are included for a better understanding of it.]

1. Phosphoroamidate Mustard Prodrugs

| Code | Structure |
|---|---|
| SU025-04 | 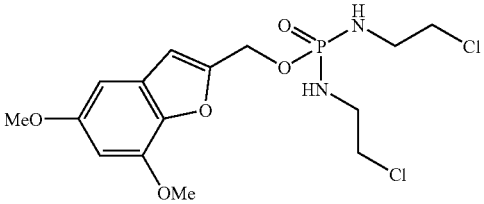 |
| SU046-04 | 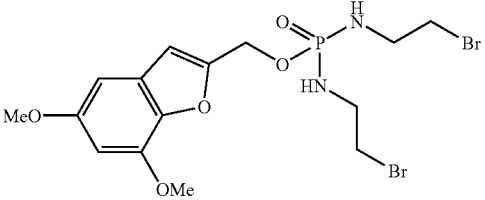 |

Synthesis of the Phosphoroamidate Prodrugs SU025-04 and SU046-04

1. Synthesis of the Trigger Component of the Prodrugs

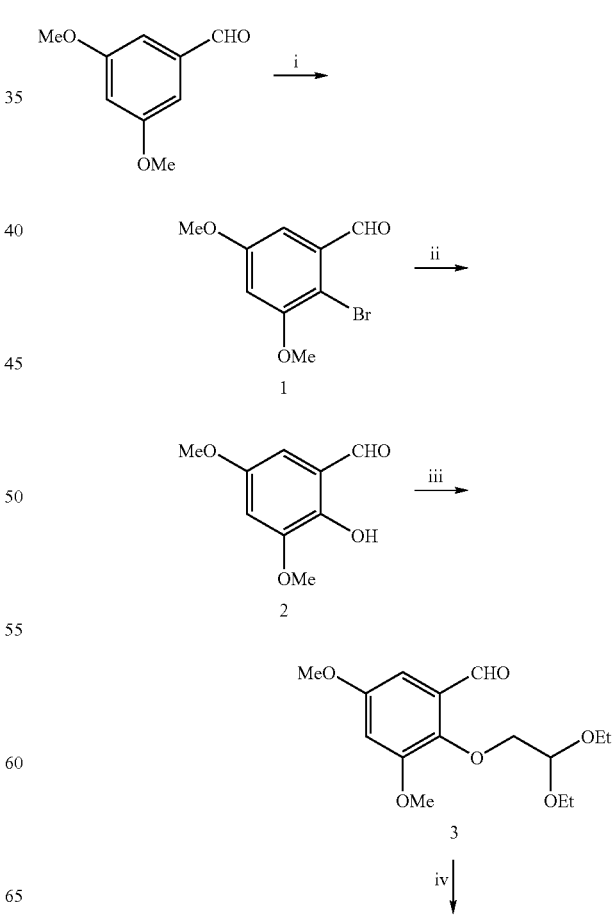

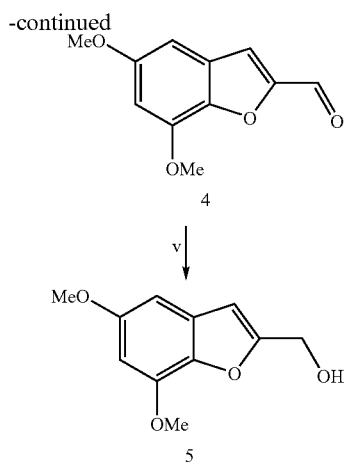

Reagents and conditions: (i) Br₂, CH₃CO₂H, (ii) (a) morpholine, THF, -50° C., 15 min; (b) n-BuLi, -75° C., 35 min; (c) PhNO₂, -75° C., 4 h, H₃O⁺, 15 min; (iii) BrCH₂CH(OEt)₂, DMF, 140° C.; (iv) CH₃CO₂H, 120° C., 24 h; (v) NaBH₄, THF, EtOH, rt

2-Bromo-3,5-dimethoxybenzaldehyde (1)

3,5-dimethoxybenzaldehyde (12.6 g, 76 mmol) was dissolved in acetic acid (350 mL). The resulting colourless solution was cooled to 0° C. A solution of bromine (3.9 mL) in ethanoic acid (50 mL) was added dropwise over 1 h. Once the addition was complete the ice bath was removed and the resulting pale green solution was stirred overnight at room temperature. Cold water was added to the solution. The resulting white solid was collected by vacuum filteration and rinsed with water. The solid was then redissolved in EtOAc and adsorbed on silica gel. The product was purified by flash chromatography, eluting with hexane/EtOAc (4:1) to give 1 (12.5 g, 66%) as a white solid. m/z=345.98 (M+H). $^1$H NMR (500 MHz, CDCl₃): δ: 10.43 (1H, s, CHO), 7.06 (1H, s, ArH), 6.73 (1H, s, ArH), 3.93 (3H, s, CH₃O), 3.86 (3H, s, CH₃O). $^{13}$C NMR (500 MHz, CDCl₃): δ: 192.09 (CHO), 159.92 (C-5), 157.02 (C-3), 134.67 (C-1), 109.12 (C-2), 105.83, 103.37 (C-4 & C-6), 56.60 (OMe), 55.82 (OMe).

2-Hydroxy-3,5-dimethoxybenzaldehyde (2)

Morpholine (2.05 g, 24 mmol) and THF (40 mL) were placed in a three-necked, round bottomed flask equipped with a stirring bar, septum cap, dropping funnel, thermometer, and argon inlet. The flask was cooled in a dry ice-acetone bath to −50° C., and a solution of n-BuLi in hexane (1.6M, 15 mL, 24 mmol) was added all at once. After 10 min a solution of 1 (4.9 g, 20 mmol) in THF (30 mL) was added dropwise via a syringe over a period of 4 min, and the mixture was cooled to ~−75° C. over 20 min. n-BuLi in hexane (1.6M, 20 mL, 32 mmol) was then added dropwise over 45 min, keeping the temperature at −75° C. After complete addition of n-BuLi the solution was stirred for 35 min. A solution of nitrobenzene (6.90 g, 46 mmol) in 10 mL THF was added from the dropping funnel, keeping the temperature at −75° C. The resulting dark mixture was stirred at −75° C. for 4 h and then allowed to warm to room temperature. It was acidified to pH 1 with 6N HCl and stirred for 15 min. After dilution with brine (100 mL), THF was removed in vacuo. The aqueous solution was extracted with diethyl ether (4×40 mL). The combined organic layers were extracted with 2 N NaOH (3×40 mL). The combined NaOH extracts were washed with diethyl ether (3×20 mL) and then acidified to pH 1 with concentrated HCl. The resulting mixture was extracted with CH₂Cl₂ (3×20 mL), and the combined organic extracts were washed with brine, dried (MgSO₄) and adsorbed on silica gel. The product was purified by flash chromatography, eluting with EtOAc/hexane (1:2). Pure 2 was obtained (2.0 g, 55%) as a yellow solid. m/z=183.06 (M+H). $^1$H NMR (500 MHz, CDCl₃): δ: 10.71 (1H, s, OH), 9.91 (1H, s, CHO), 6.77 (1H, d, J$_{4,6}$=2.8 Hz, H-6), 6.61 (1H, d, J$_{4,6}$=2.8 Hz, H-4), 3.92 (3H, s, OMe), 3.84 (3H, s, OMe). $^{13}$C NMR CDEPT135 (500 MHz, CDCl₃): δ: 196.11 (CHO), 107.93 (C-6), 103.90 (C-4), 56.29 (OMe), 55.83 (OMe).

2-(2,2-Diethoxyethoxy)-3,5-dimethoxybenzaldehyde (3)

To a stirred suspension containing 2 (1.1 g, 6.0 mmol) and K₂CO₃ (1.0 g, 7.2 mmol) in DMF (100 mL), bromoacetaldehyde diethyl acetal (0.93 mL, 6.0 mmol) was added dropwise. The mixture was refluxed for 4 h. After cooling, the precipitate was filtered off and the solvent was evaporated in vacuo. The crude residue was adsorbed on silica gel and purified by flash chromatography, eluting with hexane/EtOAc (4:1) to give 3 (1.2 g, 67%) as a clear oil. $^1$H NMR (500 MHz, CDCl₃): δ: 10.50 (1H, s, CHO), 6.88 (1H, d, J$_{4,6}$=2.9 Hz, H-6), 6.74 (1H, d, J$_{4,6}$=2.9 Hz, H-4), 4.83 (1H, t, J$_{4,6}$=5.3 Hz, CH), 4.14 (2H, d, J$_{4,6}$=5.3 Hz, CH₂), 3.88 (3H, s, OMe), 3.83 (3H, s, OMe), 3.77-3.71) (2H, m, CH₂CH₃), 3.63-3.58 (2H, m, CH₂CH₃), 1.24 (6H, t, J=7.1 Hz, 2×CH₃).

5,7-dimethoxybenzofuran-2-carbaldehyde (4)

A stirred solution of 3 (1.2 g, 4.0 mmol) in acetic acid (35 mL) was refluxed for 16 h. After cooling, the solution was evaporated to dryness. The crude product was adsorbed on silica gel and purified by flash chromatography, eluting with hexane/EtOAc (2:1) to give 4 (230 mg, 28%) as a white solid. $^1$H NMR (500 MHz, CDCl₃): δ: 9.89 (1H, s, CHO), 7.50 (1H, s, H-3), 6.69 (1H, d, J$_{4,6}$=2.2 Hz, H-6), 6.64 (1H, d, J$_{4,6}$=2.2 Hz, H-4), 4.01 (3H, s, OMe), 3.87 (3H, s, OMe). $^{13}$C NMR CDEPT 135, (500 MHz, CDCl₃): δ: 179.91 (CHO), 153.37 (C-2), 116.10 (C-3), 101.80 (C-6), 94.90 (C-4), 56.20 (OMe), 55.88 (OMe).

(5,7-dimethoxybenzofuran-2-yl)methanol (5)

Compound 4 (460 mg, 2.23 mmol) was dissolved in THF (5 mL) and EtOH (1 mL). NaBH₄ (102 mg, 2.68 mmol) was added portionwise at 0° C., with vigorous stirring. The suspension was stirred at 0° C. for 15 min and then at room temperature for 1 h. Solvents were evaporated off in-vacuo. The crude residue was taken up in EtOAc and washed with water, brine and dried (MgSO₄). The residue was adsorbed on silica gel and purified by flash chromatography, eluting with hexane/EtOAc (1:1) to give 5 (388 mg, 82%) as an oil. m/z=209.08 (M+H). $^1$H NMR (500 MHz, CDCl₃): δ: 6.62 (1H, s, H-3), 6.60 (1H, s, H-6), 6.46 (1H, s, H-4), 4.76 (2H, s, 2-CH₂), 3.99 (3H, s, OMe), 3.85 (3H, s, OMe). $^{13}$C NMR (500 MHz, CDCl₃): δ: 157.23 (C-5), 156.72 (C-1), 145.36 (C-7), 139.50 (C-1a), 129.38 (C-4a), 104.62 (C-3), 96.96 (C-6), 94.58 (C-4), 57.98 (2-CH₂), 55.95 (OMe), 55.83 (OMe).

2. Synthesis of the Effector Components of the Prodrugs

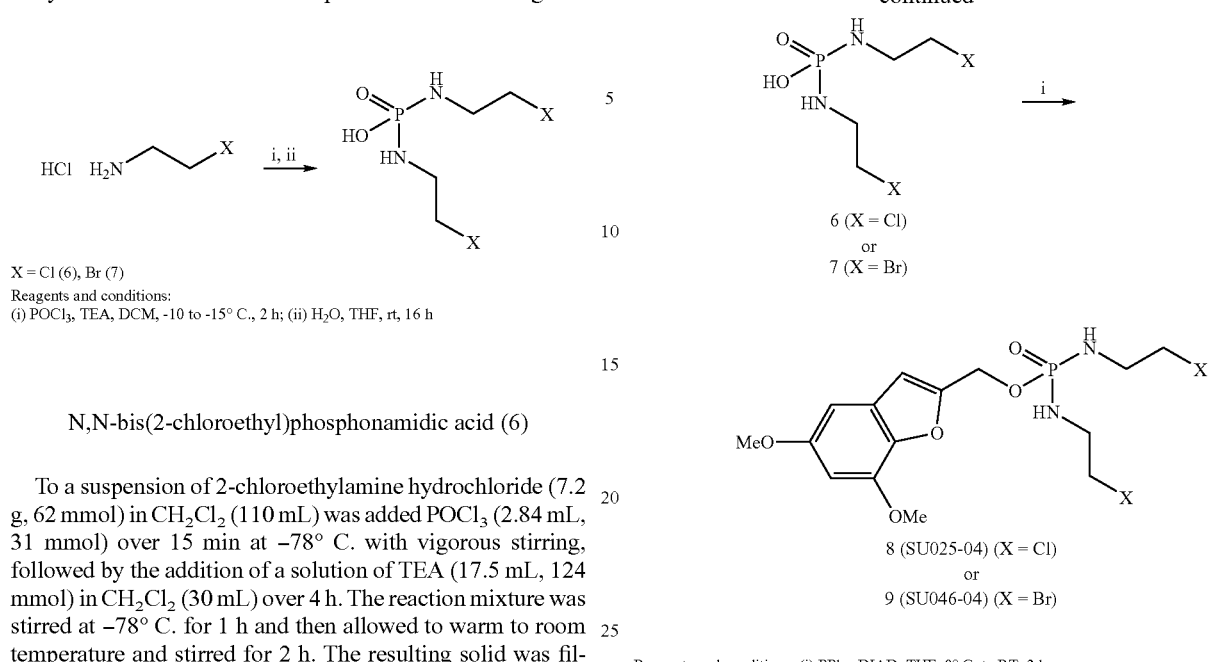

X = Cl (6), Br (7)
Reagents and conditions:
(i) POCl₃, TEA, DCM, -10 to -15° C., 2 h; (ii) H₂O, THF, rt, 16 h

N,N-bis(2-chloroethyl)phosphonamidic acid (6)

To a suspension of 2-chloroethylamine hydrochloride (7.2 g, 62 mmol) in $CH_2Cl_2$ (110 mL) was added $POCl_3$ (2.84 mL, 31 mmol) over 15 min at −78° C. with vigorous stirring, followed by the addition of a solution of TEA (17.5 mL, 124 mmol) in $CH_2Cl_2$ (30 mL) over 4 h. The reaction mixture was stirred at −78° C. for 1 h and then allowed to warm to room temperature and stirred for 2 h. The resulting solid was filtered and washed with cold EtOAc. The solid was discarded. The filtrate was concentrated under vacuum to about 5 mL and EtOAc was added (10 mL). The resulting suspension was filtered and washed with EtOAc (2×10 mL). The solid was again discarded. The filtrate was concentrated under vacuum to dryness. The residue was then dissolved in THF (7 mL) followed by addition of an aqueous NaBr solution (NaBr (5 g) in 100 mL water) at 0° C. over 20 min. The mixture was then warmed to room temperature and stirred for 15 h in a water bath. A white solid precipitated from the reaction mixture. The mixture was then kept at −20° C. in the freezer for 2 h. The crystalline solid was filtered and washed with cold water (2×50 mL, 0° C.) and cold EtOAc (2×50 mL, 0° C.). After drying at room temperature under vacuum overnight, the product 6 was obtained (1.8 g, 26%) as a white solid. $^1H$ NMR (500 MHz, DMSO-$d_6$): δ: 5.29 (3H, br, OH & NH), 3.55 (4H, t, J=7.0 Hz, 2×CH₂), 3.01 (4H, dt, J=12.2, 7.0 Hz, 2×CH₂). $^{31}P$ NMR (500 MHz, DMSO-$d_6$) δ: 12.28 ppm.

N,N-bis(2-bromoethyl)phosphonamidic acid (7)

Compound 7 was synthesized using a similar method as above. It was obtained in 18% yield (1.64 g). $^1H$ NMR (500 MHz, DMSO-$d_6$): δ: 6.08 (3H, s, OH & NH), 3.46 (4H, t, J=7.0 Hz, 2×CH₂), 3.01 (4H, dt, J=12.2, 7.0 Hz, 2×CH₂). $^{31}P$ NMR (500 MHz, DMSO-$d_6$) δ: 12.23 ppm.

3. Coupling Reaction for the Synthesis of SU025-04 and SU046-04

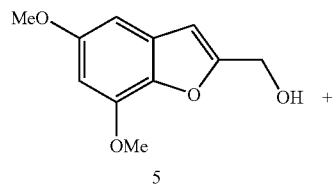

5,7-Dimethoxybenzofuran-2-yl)methylN,N'-bis(2-chloroethyl)phosphordiamidate (8) SU025-04

To a suspension of 5 (300 mg, 1.44 mmol), 6 (479 mg, 2.16 mmol) and PPh₃ (565 mg, 2.16 mmol) in THF (20 mL) was added DIAD (0.426 mL, 2.16 mmol), dropwise at 0° C. The resulting suspension was warmed to room temperature and stirred for 2 h. The solvent was removed, and the residue was purified by flash chromatography (70% acetone in toluene) to give 8 (250 mg, 42%) as an oil. m/z=823.08 (2M+H). $^1H$ NMR (500 MHz, DMSO-$d_6$): δ 7.27 (2H, s, 2×NH), 6.75 (1H, s, ArH-3), 6.62 (1H, d, $J_{4,6}$=2.3 Hz, ArH-4), 6.49 (1H, d, $J_{4,6}$=2.3 Hz, ArH-6), 5.13 (2H, d, J=9.3 Hz, 2H), 3.99 (3H, s, OMe), 3.86 (3H, s, OMe), 3.29 (4H, m, 2×CH₂), $^{31}P$ NMR (500 MHz, DMSO-$d_6$) δ: 14.76 ppm. HRMS: Calcd for $C_{15}H_{21}N_2O_5PCl_2Na$, 433.0463; found 433.0471.

5,7-Dimethoxybenzofuran-2-yl)methylN,N'-bis(2-bromoethyl)phosphordiamidate (9) SU046-04

Compound 9 (SU046-04) was synthesized using a similar method as above. It was obtained in 25% yield (10 mg). m/z=500.96 (M+H), 1000.93 (2M+H). $^1H$ NMR (500 MHz, CDCl₃): δ 6.76 (1H, s, ArH-3), 6.61 (1H, d, $J_{4,6}$=2.2 Hz, ArH-4), 6.48 (1H, d, $J_{4,6}$=2.2 Hz, ArH-6), 5.13 (2H, d, J=9.4 Hz, 2H), 3.99 (3H, s, OMe), 3.86 (3H, s, OMe), 3.49-3.45 (4H, m, 2×CH₂), 3.40-3.33 (4H, m, 2×CH₂) 3.23 (2H, bs, NH). $^{13}C$ NMR (500 MHz, CDCl₃): δ: 156.98, 152.91, 145.58, 139.97, 129.06, 128.24, 107.45, 97.70, 94.56, 59.73, 56.00, 42.90, 34.76, 30.98. HRMS: Calcd for $C_{15}H_{21}N_2O_5PBr_2Na$, 520.9453; found 520.9454.

2. Ether and Thioether-Linked Model Prodrugs
TLE-M2-SU010A
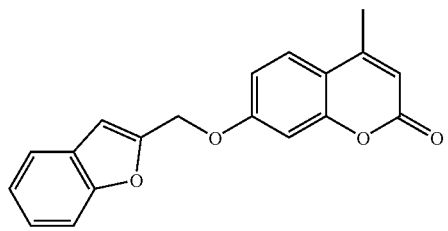
VG015-05
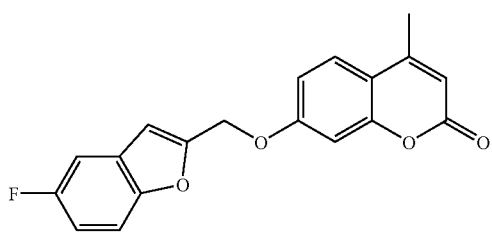
VG016-05 (†)
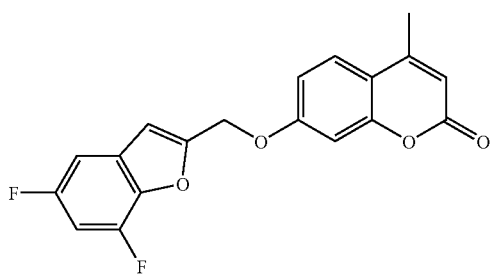
VG017-05
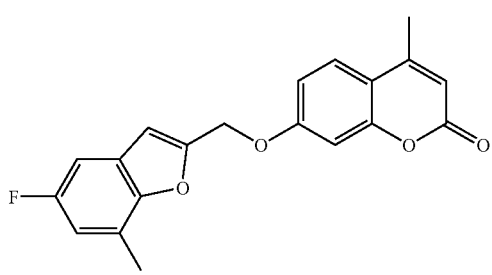
VG027-05
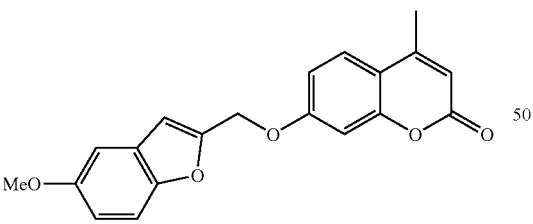
VG029-05
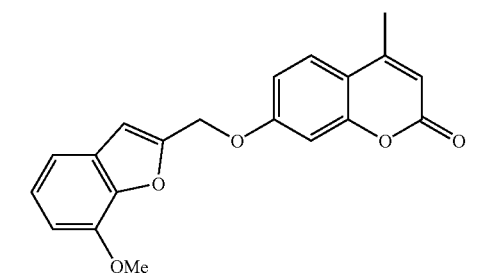
VG035-04
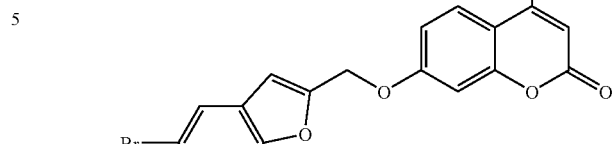
VG028-05
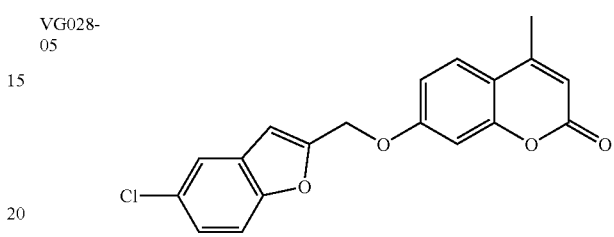
VG035-05
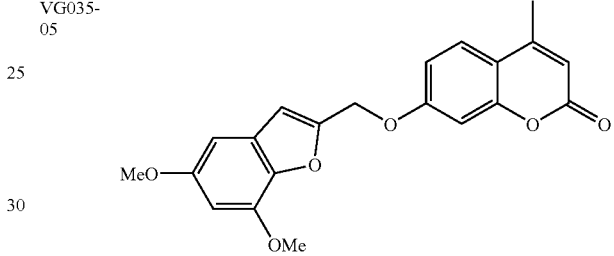
TLE-M1-SU001A (†)
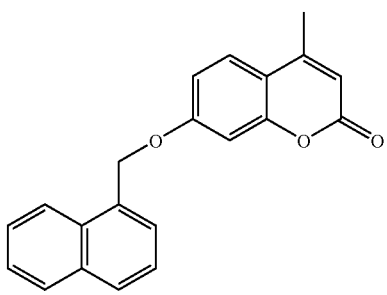
VG040-03
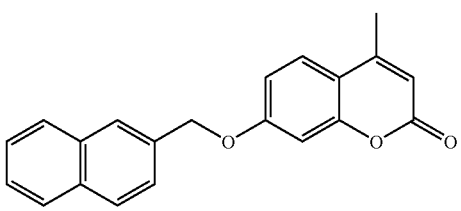
TLE-M1-SU004A (†)
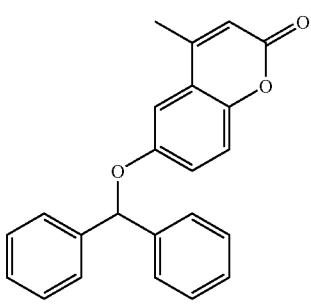

| | |
|---|---|
| VG039-03 | 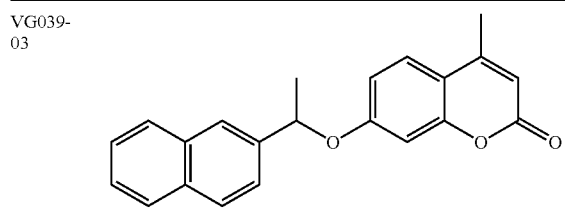 |
| SU06-02 (†) | 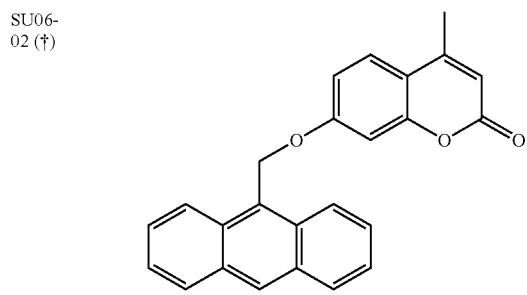 |
| SU010-02 (†) | 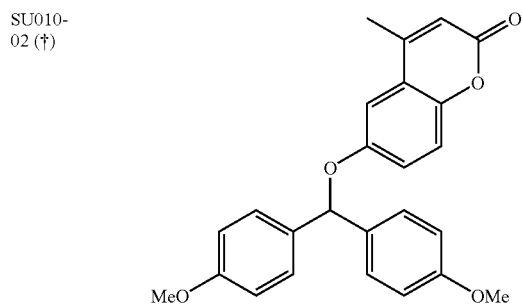 |
| VG033-03 | 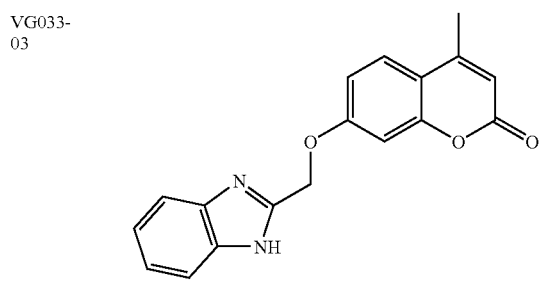 |
| VG015-04 (†) | 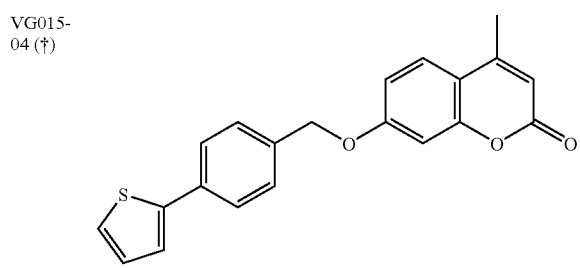 |
| VG014-04 | 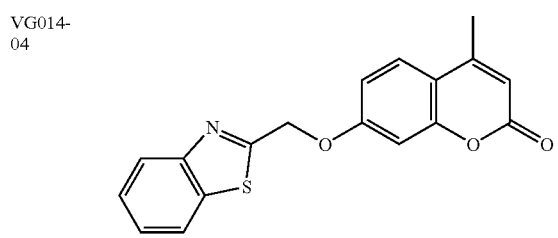 |
| VG015-02 (†) | 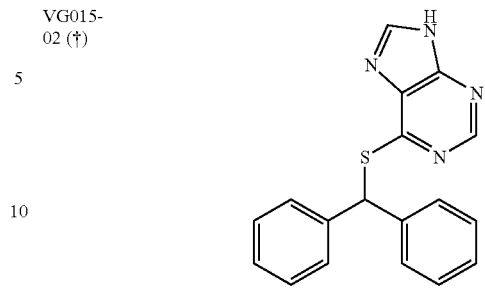 |

Synthesis of Ether and Thioether Linked Prodrugs 7-(benzofuran-2-ylmethoxy)-4-methyl-2H-chromen-2-one (10) TLE-M2-SU010A

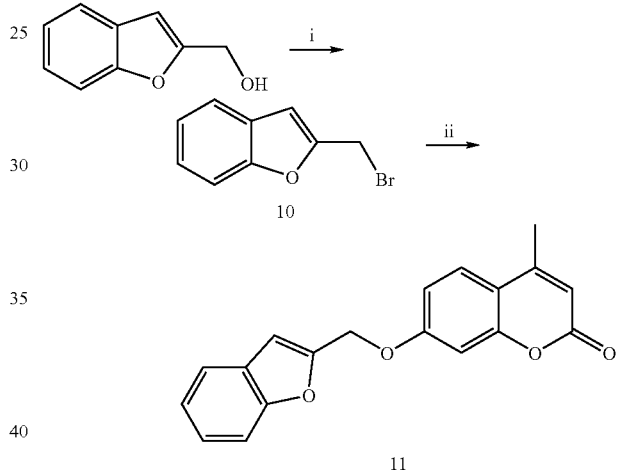

(TLE-M2-SU010A)

Reagents and conditions: (i) PBr₃, pyridine, toluene; (ii) Sodium ethoxide, 7-hydroxy-4-methylcoumarin, DMF 2-(bromomethyl)benzofuran (10)

Benzofuran-2yl methanol (1.0 g, 6.7 mmol) was dissolved in toluene (50 mL) and pyridine (653 µL, 8.1 mmol) was added. The solution was cooled to 0° C. PBr$_3$ (760 µL, 8.1 mmol) was added dropwise over 15 min. The reaction mixture was then brought up to room temperature and stirred for 1 h. The mixture was washed with K$_2$CO$_3$ solution and extracted with EtOAc (3×30 mL). The EtOAc layer was washed with brine and dried (MgSO$_4$). The solvent was evaporated off in-vacuo and product was purified by flash chromatography, eluting with hexane:EtOAc (4:1) to give 10 (780 mg, 55%) as an oil. $^1$H NMR (500 MHz, CDCl$_3$): δ: 7.57 (1H, d, J=7.75 Hz, H-4), 7.52 (1H, d, J=8.40, H-7), 7.35 (1H, t, J=8.90, H-4), 7.27 (1H, t, J=8.9 Hz, H-5), 6.79 (1H, s, H-3), 4.64 (2H, s, 2-CH$_2$). $^{13}$C NMR CDEPT 135, (500 MHz, CDCl$_3$): δ: 155.34 (C-2), 152.65 (C7a), 129.08 (C3a), 125.20 (C-6), 123.16 (C-5), 121.34 (C—C-4), 111.46 (C-7), 106.30 (C-3), 23.61 (CH$_2$—Br).

7-(benzofuran-2-ylmethoxy)-4-methyl-2H-chromen-2-one (11) TLE-M2-SU010A

Sodium ethoxide (77 mg, 1.13 mmol) was added to DMF (10 mL) at 0° C., and the suspension was stirred for 10 min. 7-hydroxy-4-methylcoumarin (200 mg, 1.13 mmol) was slowly added and resulting mixture was stirred at this temp for 0.5 h. To this mixture 10 (200 mg, 0.94 mmol) was added portionwise. Resulting reaction mixture was stirred at room temperature for 2 h. DMF was evaporated off in-vacuo and the residue was taken up in EtOAc, and washed with brine, water and 1M NaOH (2×30 mL). The organic layer was dried (MgSO$_4$) and product was purified by flash chromatography, eluting with hexane:EtOAc (2:1) to give 11 (35 mg, 12%) as a white solid. m/z=307 (M+H). H$^1$ NMR (500 MHz, DMSO-d$_6$): δ=7.75-7.60 (2H, m, ArH), 7.40-7.25 (2H, m, ArH), 7.23 (1H, s, ArH), 7.12 (2H, d, CH), 6.25 (1H, s, CH), 5.41 (2H, s, CH$_2$), 2.38 (3H, s, CH$_3$).

7-((5-fluorobenzofuran-2-yl)methoxy)-4-methyl-2H-chromen-2-one (16) VG015-05

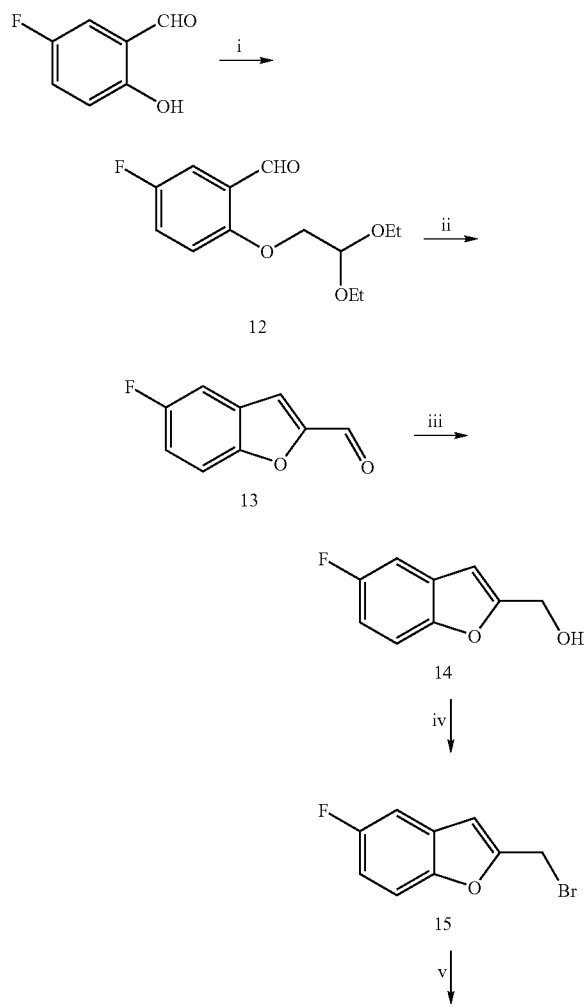

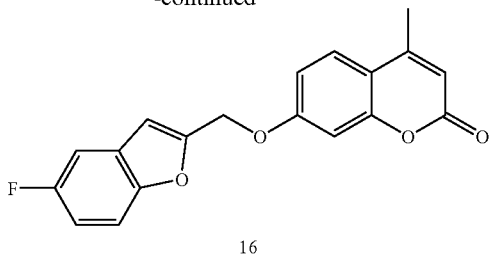

(VG015-05)

Reagents and conditions: (i) BrCH$_2$CH(OEt)$_2$, DMF, 140° C.; (ii) CH$_3$CO$_2$H, 120° C., 24 h; (iii) NaBH$_4$, THF, EtOH, rt (iv) PBr$_3$, pyridine, toluene, rt; (v) Sodium ethoxide, 7-hydroxy-4-methylcoumarin, DMF, rt

2-(2,2-Diethoxyethoxy)-5-fluorobenzaldehyde (12)

To a stirred suspension containing 2-hydroxy-5-fluorobenzaldehyde (500 mg, 3.57 mmol) and K$_2$CO$_3$ (524 mg, 13.79 mmol) in DMF (10 mL), bromoacetaldehyde diethyl acetal (0.6 mL, 3.93 mmol) was added dropwise. The mixture was refluxed for 4 h. After cooling, the precipitate was filtered off and the solvent was evaporated in vacuo. The crude residue was adsorbed on silica gel and purified by flash chromatography, eluting with hexane/EtOAc (4:1) to give 12 (300 mg, 33%) as an oil. $^1$H NMR (500 MHz, CDCl$_3$): δ: 10.30 (1H, s, CHO), 7.31 (1H, d, J=7.85 Hz), 7.10 (1H, t, J=7.80 Hz), 6.87 (1H, d, J=8.86 Hz), 4.75 (1H, s, CH), 3.97 (2H, d, J=2.35 Hz, CH$_2$), 3.67-3.64 (2H, m, CH$_2$CH$_3$), 3.53-3.50 (2H, m, CH$_2$CH$_3$), 1.11 (6H, t, J=6.00 Hz, 2×CH$_3$).

5-fluorobenzofuran-2-carbaldehyde (13)

A stirred solution of 12 (300 mg, 4.0 mmol) in acetic acid (10 mL) was refluxed for 24 h. After cooling, the solution was evaporated to dryness. The crude product was adsorbed on silica gel and purified by flash chromatography, eluting with hexane/EtOAc (4:1) to give the 13 (180 mg, 94%) as a white solid, $^1$H NMR (500 MHz, CDCl$_3$): δ: 9.89 (1H, s, CHO), 7.57 (2H, m, ArH), 7.41 (1H, d, J=7.20 Hz), 7.26 (1H, d, J=6.94 Hz, H-4). $^{13}$C NMR CDEPT 135, (500 MHz, CDCl$_3$): δ: 179.74 (CHO), 117.73 (C-3), 117.25 (C-7), 113.81 (C-6), 108.68 (C-4).

(5-fluorobenzofuran-2-yl)methanol (14)

Compound 13 (180 mg, 1.10 mmol) was dissolved in EtOH (12 mL). NaBH$_4$ (45 mg, 1.21 mmol) was added portionwise at 0° C., with vigorous stirring. The suspension was stirred at 0° C. for 15 min and then at room temperature for 1.5 h. Solvents were evaporated off in-vacuo. The crude residue was taken up in EtOAc and washed with water, brine and dried (MgSO$_4$). The solvent was evaporated off in vacuo. The residue was adsorbed on silica gel and purified by flash chromatography, eluting with hexane/EtOAc (3:1) to give 14 (150 mg, 91%) as a white solid. $^1$H NMR (500 MHz, CDCl$_3$): δ: 7.36 (1H, d, J=8.35 Hz, H-7), 7.19 (1H, d, J=7.80, H-4), 7.00 (1H, t, J=8.75H-6), 6.60 (1H, s, H-3), 4.75 (2H, s, CH$_2$).

2-(bromomethyl)-5-fluorobenzofuran (15)

Compound 14 (150 mg, 0.90 mmol) was dissolved in toluene (10 mL) and the solution was cooled to 0° C. PBr$_3$ (102 µL, 1.08 mmol) was added dropwise over 15 min. The reaction mixture was then brought up to room temperature and stirred for 1 h. The solvent was evaporated off in-vacuo. The residue was adsorbed on silica gel and purified by flash chromatography, eluting with hexane/EtOAc (4:1) to give 15 (150 mg, 72%) as an oil. $^1$H NMR (500 MHz, CDCl$_3$): δ: 7.43 (1H, d, J=7.60 Hz, H-7), 7.21 (1H, t, J=8.10, H-4), 7.06 (1H, t, J=8.90, H-4), 6.75 (1H, s, H-3), 4.60 (2H, s, 2-CH$_2$). $^{13}$C NMR CDEPT 135, (500 MHz, CDCl$_3$): δ: 113.08 (C-7), 112.08 (C-6), 106.87 (C-4), 106.34 (C-3), 60.42 (CH$_2$—Br).

7-((5-fluorobenzofuran-2-ylmethoxy)-4-methyl-2H-chromen-2-one (16) VG015-05

Sodium ethoxide (8.9 mg, 0.13 mmol) was added to DMF (3 ml) at 0° C., and the suspension was stirred for 10 min. 7-hydroxy-4-methylcoumarin (25.4 mg, 0.14 mmol) was slowly added and resulting mixture was stirred at this temp for 0.5 h. To this mixture 15 (30 mg, 0.13 mmol) was added portionwise. Resulting reaction mixture was stirred at room temperature for 2 h. DMF was evaporated off in-vacuo and the residue was purified by flash chromatography, eluting with hexane:EtOAc (3:1) to give 16 (9.0 mg, 21%) as a white solid. m/z=325.20 (M+H).

7-((5,7-difluorobenzofuran-2-ylmethoxy)-4-methyl-2H-chromen-2-one (19) VG016-05

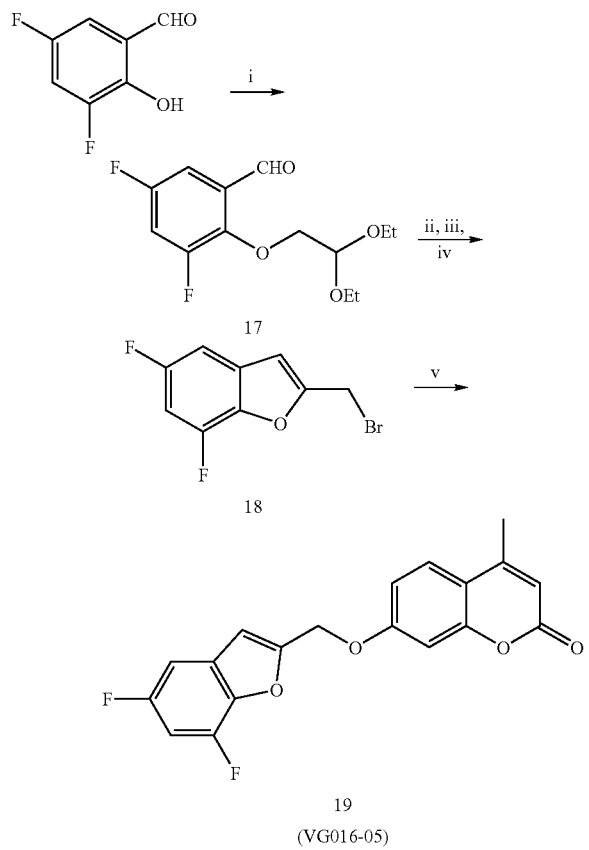

19
(VG016-05)
Reagents and conditions: (i) BrCH$_2$CH(OEt)$_2$, DMF, 140° C.; (ii) CH$_3$CO$_2$H, 120° C., 24 h; (iii) NaBH$_4$, THF, EtOH, rt (iv) PBr$_3$, pyridine, toluene, rt; (v) Sodium ethoxide, 7-hydroxy-4-methylcoumarin, DMF, rt 2-(2,2-diethoxyethoxy)-3,5-difluorobenzaldehyde (17)

To a stirred suspension containing 2-hydroxy-3,5-fluorobenzaldehyde (1.0 g, 6.32 mmol) and K$_2$CO$_3$ (960 mg, 6.95 mmol) in DMF (10 mL), bromoacetaldehyde diethyl acetal (1.07 mL, 6.95 mmol) was added dropwise. The mixture was refluxed for 4 h. After cooling, the precipitate was filtered off and the solvent was evaporated in vacuo. The crude residue was adsorbed on silica gel and purified by flash chromatography, eluting with hexane/EtOAc (4:1) to give 17 (380 mg, 22%) as an oil, $^1$H NMR (500 MHz, CDCl$_3$): δ: 10.41 (1H, s, CHO), 7.29 (1H, d, J=6.80 Hz), 7.10 (1H, t, J=8.30 Hz), 4.80 (1H, s, CH), 4.20 (2H, d, J=3.25 Hz, CH$_2$), 3.71 (2H, t, J=7.10 Hz, CH$_2$CH$_3$), 3.57 (2H, t, J=7.45 Hz, CH$_2$CH$_3$), 1.19 (6H, t, J=6.25 Hz, 2×CH$_3$).

2-(bromomethyl)-5,7-difluorobenzofuran (18)

A stirred solution of 17 (380 mg, 1.39 mmol) in acetic acid (10 mL) was refluxed for 24 h. After cooling, the solution was evaporated to dryness. The crude product (300 mg) was dissolved in EtOH (5 mL). NaBH$_4$ (73 mg, 1.98 mmol) was added portionwise at 0° C., with vigorous stirring. The suspension was stirred at 0° C. for 15 min and then at room temperature for 1.5 h. Solvents were evaporated off in-vacuo. The crude residue (280 mg) was dissolved in toluene (20 mL) and the solution was cooled to 0° C. PBr$_3$ (142 μL, 1.52 mmol) was added dropwise over 15 min. The reaction mixture was then brought up to room temperature and stirred for 1 h. The solvent was evaporated off in-vacuo. The residue was adsorbed on silica gel and purified by flash chromatography, eluting with hexane/EtOAc (4:1) to give 18 (210 mg, 61%). $^1$H NMR (500 MHz, CDCl$_3$): δ: 7.03 (1H, d, J=7.50 Hz, H-4), 6.87 (1H, t, J=9.80, H-5), 6.79 (1H, s, H-3), 4.59 (2H, s, 2-CH$_2$).

7-((5,7-difluorobenzofuran-2-yl)methoxy)-4-methyl-2H-chromen-2-one (19) VG016-05

Sodium ethoxide (8.9 mg, 0.13 mmol) was added to DMF (3 mL) at 0° C., and the suspension was stirred for 10 min. 7-hydroxy-4-methylcoumarin (25.4 mg, 0.14 mmol) was slowly added and resulting mixture was stirred at this temp for 0.5 h. To this mixture 2-(bromomethyl)-5-fluorobenzofuran (30 mg, 0.12 mmol) was added portionwise. Resulting reaction mixture was stirred at room temperature for 2 h. DMF was evaporated off in-vacuo and the residue was purified by flash chromatography, eluting with hexane: EtOAc (3:1) to give 19 (8.8 mg, 21%) as a white solid. m/z=343.12 (M+H).

7-((5,7-difluorobenzofuran-2-yl)methoxy)-4-methyl-2H-chromen-2-one (22) VG017-05

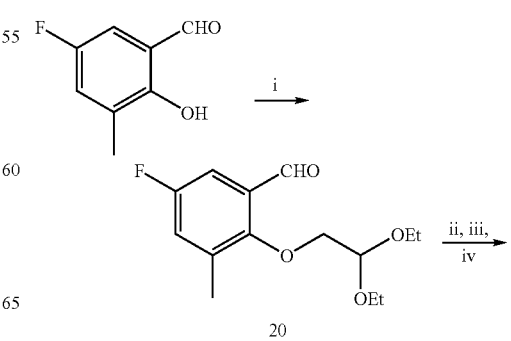

20

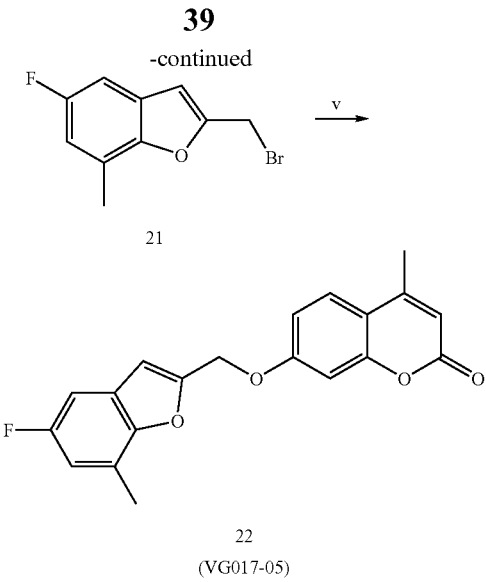

22
(VG017-05)

Reagents and conditions: (i) BrCH₂CH(OEt)₂, DMF, 140° C.; (ii) CH₃CO₂H, 120° C., 24 h; (iii) NaBH₄, THF, EtOH, rt (iv) PBr₃, pyridine, toluene, rt; (v) Sodium ethoxide, 7-hydroxy-4-methylcoumarin, DMF, rt 2-(2,2-diethoxyethoxy)-5-fluoro-3-methylbenzaldehyde (20)

To a stirred suspension containing 5-fluoro-2-hydroxy-3-methylbenzaldehyde (1.0 g, 6.49 mmol) and $K_2CO_3$ (980 mg, 7.10 mmol) in DMF (8 mL), bromoacetaldehyde diethyl acetal (1.10 mL, 7.15 mmol) was added dropwise. The mixture was refluxed for 4 h. After cooling, the precipitate was filtered off and the solvent was evaporated in vacuo. The crude residue was adsorbed on silica gel and purified by flash chromatography. The product was eluted with hexane/EtOAc (4:1) to give 20 (350 mg, 20%) as an oil, $^1$H NMR (500 MHz, CDCl₃): δ: 10.40 (1H, s, CHO), 7.32 (1H, d, J=7.30 Hz, ArH), 7.14 (1H, d, J=7.75 Hz, ArH), 4.85 (1H, s, CH), 3.95 (2H, s, CH₂), 3.75 (2H, t, J=7.15 Hz, CH₂CH₃), 3.61 (2H, t, J=7.20 Hz, CH₂CH₃), 2.36 (3H, s, $\overline{CH_3}$), 1.24 (6H, t, J=5.65 Hz, 2×$\overline{CH_3}$).

2-(bromomethyl)-5-fluoro-7-methylbenzofuran (21)

A stirred solution of 20 (350 mg, 1.30 mmol) in acetic acid (10 mL) was refluxed for 24 h. After cooling, the solution was evaporated to dryness. The crude product (300 mg) was dissolved in THF (5 mL). NaBH₄ (78 mg, 2.02 mmol) was added portionwise at 0° C., with vigorous stirring. The suspension was stirred at 0° C. for 15 min and then at room temperature for 1.5 h. Solvents were evaporated off in-vacuo. The crude residue (260 mg) was dissolved in toluene (20 mL) and the solution was cooled to 0° C. PBr₃ (135 μL, 1.44 mmol) was added dropwise over 15 min. The reaction mixture was then brought up to room temperature and stirred for 1 h. The solvent was evaporated off in-vacuo. The residue was adsorbed on silica gel and purified by flash chromatography, eluting with hexane/EtOAc (4:1) to give 21 (200 mg, 36%). $^1$H NMR (500 MHz, CDCl₃): δ: 7.03 (1H, d, J=7.50 Hz, H-4), 6.88 (1H, t, J=9.80, H-5), 6.75 (1H, s, H-3), 4.69 (2H, s, 2-CH₂), 2.54 (3H, s, CH₃).

7-((5,7-difluorobenzofuran-2-ylmethoxy)-4-methyl-2H-chromen-2-one (22) VG017-05

Sodium ethoxide (8.9 mg, 0.13 mmol) was added to DMF (3 mL) at 0° C., and the suspension was stirred for 10 min.

7-hydroxy-4-methylcoumarin (25.4 mg, 0.14 mmol) was slowly added and resulting mixture was stirred at this temp for 0.5 h. To this mixture 21 (30 mg, 0.12 mmol) was added portionwise. Resulting reaction mixture was stirred at room temperature for 2 h. DMF was evaporated off in-vacuo and the residue was purified by flash chromatography, eluting with hexane:EtOAc (3:1) to give 22 as a white solid (11 mg, 26%). m/z=33.20 (M+H).

7-((5-methoxybenzofuran-2-ylmethoxy)-4-methyl-2H-chromen-2-one (27) VG027-05

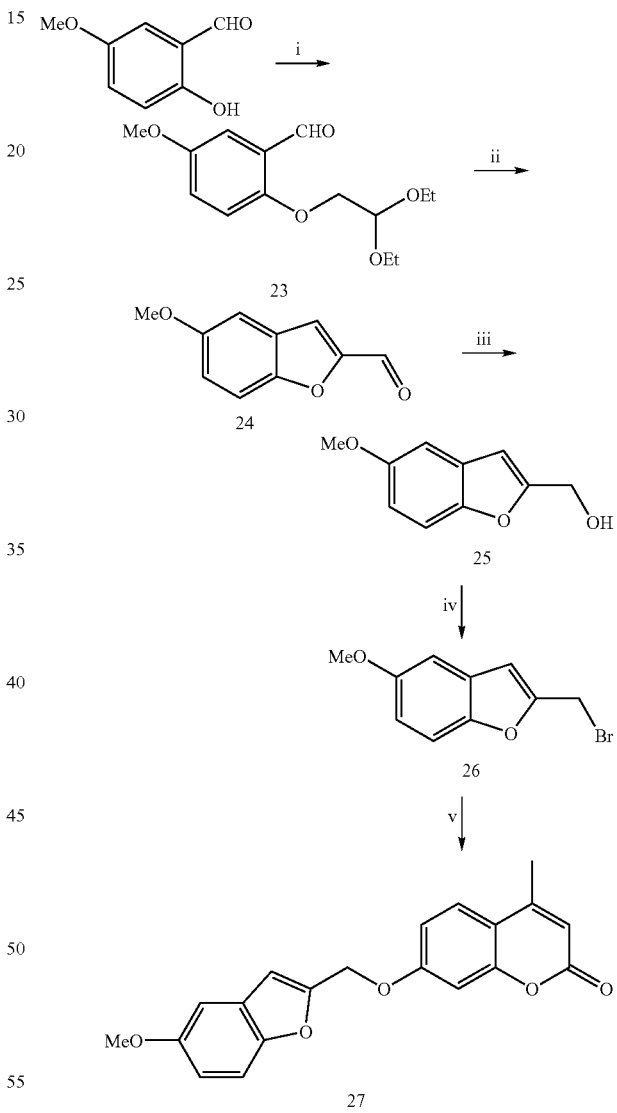

VG027-05

Reagents and conditions: (i) BrCH₂CH(OEt)₂, DMF, 140° C.; (ii) CH₃CO₂H, 120° C., 24 h; (iii) NaBH₄, THF, EtOH, rt (iv) PBr₃, pyridine, toluene, rt; (v) Sodium ethoxide, 7-hydroxy-4-methylcoumarin, DMF, rt 2-(2,2-diethoxyethoxy)-5-methoxybenzaldehyde (23)

To a stirred suspension containing 2-hydroxy-5-methoxybenzaldehyde (2.0 g, 13.16 mmol) and $K_2CO_3$ (2.18 g, 15.79 mmol) in DMF (20 mL), bromoacetaldehyde diethyl acetal (2.43 mL, 15.79 mmol) was added dropwise. The mixture was refluxed for 4 h. After cooling, the precipitate was filtered off and the solvent was evaporated in vacuo. The crude residue was adsorbed on silica gel and purified by flash chromatography. The product was eluted with hexane/EtOAc (4:1) to give the target compound 23 (1.10 g, 31%) as an oil. $^1$H NMR (500 MHz, CDCl$_3$): δ: 10.49 (1H, s, CHO), 7.33 (1H, d, J=3.30 Hz, ArH), 7.12 (1H, dd, J=5.75 & 3.30 Hz, ArH), 6.97 (1H, d, J=9.05 Hz), 4.87 (1H, t, J=5.25 Hz, CH), 4.09 (2H, d, J=5.25 Hz, CH$_2$), 3.81-3.78 (2H, m, CH$_2$CH$_3$), 3.67-3.64 (2H, m, CH$_2$CH$_3$), 1.26 (6H, t, J=7.05 Hz, 2×CH$_3$).

5-methoxybenzofuran-2-carbaldehyde (24)

A stirred solution of 23 (1.0 g, 3.74 mmol) in acetic acid (10 mL) was refluxed for 16 h. After cooling, the solution was evaporated to dryness. The crude product was adsorbed on silica gel and purified by flash chromatography, eluting with hexane/EtOAc (4:1) to give 24 (160 mg, 24%) as a white solid. $^1$H NMR (500 MHz, CDCl$_3$): δ: 9.80 (1H, s, CHO), 7.49-7.45 (2H, m, ArH), 7.12-7.09 (2H, m, ArH), 3.85 (3H, s, OCH$_3$).

(5-methoxybenzofuran-2-yl)methanol (25)

Compound 24 (3.5 g, 19.9 mmol) was dissolved in EtOH (20 mL). NaBH$_4$ (957 mg, 25.87 mmol) was added portionwise at 0° C., with vigorous stirring. The suspension was stirred at 0° C. for 15 min and then at room temperature for 1.5 h. Solvent was evaporated off in-vacuo. The residue was adsorbed on silica gel and purified by flash chromatography, eluting with hexane/EtOAc (2:1) to give 25 (3.0 g, 85%) as a white solid. $^1$H NMR (500 MHz, CDCl$_3$): δ: 7.36 (1H, d, J=8.90 Hz, H-7), 7.02 (1H, d, J=2.6, H-4), 6.90 (1H, dd, J=6.30 & 2.60, H-6), 6.61 (1H, s, H-3), 4.76 (2H, s, 2-CH$_2$), 3.86 (3H, s, OCH$_3$), 2.16 (1H, bs, OH). $^{13}$C NMR CDEPT 135, (500 MHz, CDCl$_3$): δ: 113.07 (C-7), 111.69 (C-6), 104.34 (C-4), 103.60 (C-3), 58.24 (CH$_2$), 55.92 (OCH$_3$).

2-(bromomethyl)-5-methoxybenzofuran (26)

Compound 25 (40 mg, 0.22 mmol) was dissolved in toluene (5 mL) and the solution was cooled to 0° C. PBr$_3$ (21 μL, 0.22 mmol) was added dropwise over 10 min. The reaction mixture was then brought up to room temperature and stirred for 1 h. The solvent was evaporated off in-vacuo. The residue was adsorbed on silica gel and purified by flash chromatography, eluting with hexane/EtOAc (4:1) to give 26 (40 mg, 74%) as an oil. $^1$H NMR (500 MHz, CDCl$_3$): δ: 7.39 (1H, d, J=8.90 Hz, H-7), 7.01 (1H, d, J=2.55, H-4), 6.94 (1H, dd, J=6.35 & 2.60, H-6), 6.72 (1H, s, H-3), 4.61 (2H, s, 2-CH$_2$), 3.86 (3H, s, OCH$_3$).

7-((5-methoxybenzofuran-2-yl)methoxy)-4-methyl-2H-chromen-2-one (27) VG027-05

Sodium ethoxide (12 mg, 0.18 mmol) was added to DMF (5 mL) at 0° C., and the suspension was stirred for 10 min. 7-hydroxy-4-methylcoumarin (32 mg, 0.17 mmol) was slowly added and resulting mixture was stirred at this temp for 0.5 h. To this mixture 26 (40 mg, 0.17 mmol) was added portionwise. Resulting reaction mixture was stirred at room temperature for 2 h. DMF was evaporated off in-vacuo and the residue was purified by flash chromatography, eluting with hexane:EtOAc (3:1) to give 27 (17 mg, 30%) as a white solid. m/z=337.04 (M+H), 673.13 (2M+H).

7-((7-methoxybenzofuran-2-yl)methoxy)-4-methyl-2H-chromen-2-one (31) VG029-05

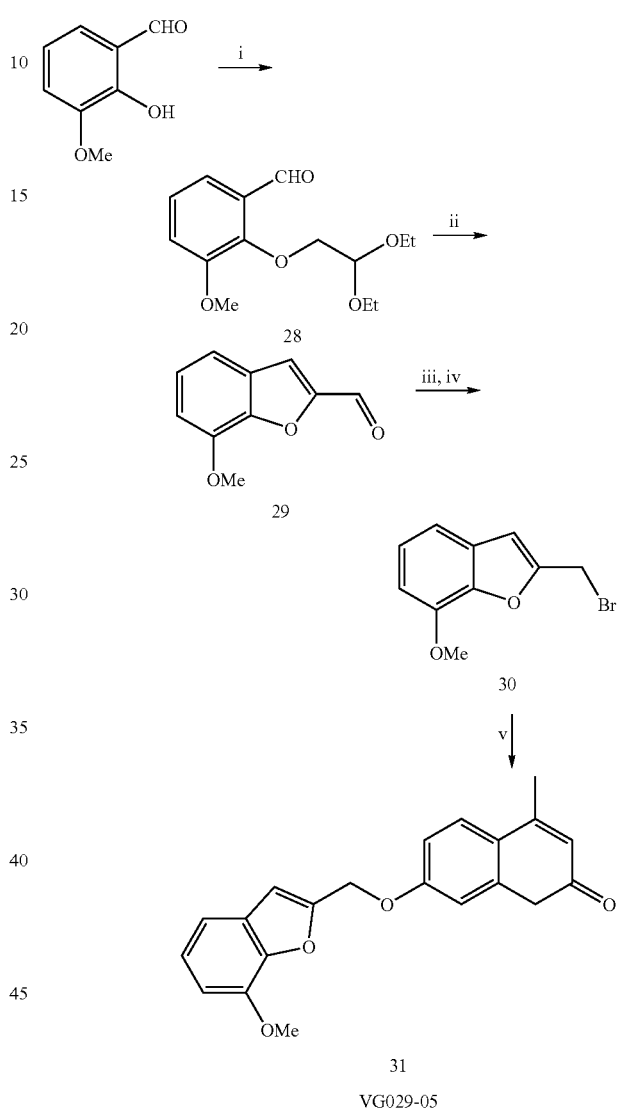

VG029-05

Reagents and conditions: (i) BrCH$_2$CH(OEt)$_2$, DMF, 140° C.; (ii) CH$_3$CO$_2$H, 120° C., 24 h; (iii) NaBH$_4$, THF, EtOH, rt (iv) PBr$_3$, pyridine, toluene, rt; (v) Sodium ethoxide, 7-hydroxy-4-methylcoumarin, DMF, rt 2-(2,2-diethoxyethoxy)-3-methoxybenzaldehyde (28)

To a stirred suspension containing 2-hydroxy-3-methoxybenzaldehyde (4.0 g, 26.3 mmol) and K$_2$CO$_3$ (4.36 g, 31.60 mmol) in DMF (15 mL), bromoacetaldehyde diethyl acetal (4.86 mL, 31.60 mmol) was added dropwise. The mixture was refluxed for 4 h. After cooling, the precipitate was filtered off and the solvent was evaporated in vacuo. The crude residue was adsorbed on silica gel and purified by flash chromatography eluting with hexane/EtOAc (4:1) to give 28 (2.60 g, 36%). $^1$H NMR (500 MHz, CDCl$_3$): δ: 10.53 (1H, s, CHO), 7.42 (1H, m, ArH), 7.14-7.12 (2H, m, ArH), 4.83 (1H, t, J=5.30 Hz, CH), 4.21 (2H, d, J=5.35 Hz, CH$_2$), 3.90 (3H, s, OCH$_3$), 3.74-3.71 (2H, m, CH$_2$CH$_3$), 3.60-3.57 (2H, m, CH$_2$CH$_3$), 1.22 (6H, t, J=7.05 Hz, 2×CH$_3$).

7-methoxybenzofuran-2-carbaldehyde (29)

A stirred solution of 28 (2.0 g, 7.46 mmol) in acetic acid (10 mL) was refluxed for 24 h. After cooling, the solution was evaporated to dryness. The crude product was adsorbed on silica gel and purified by flash chromatography, eluting with hexane/EtOAc (4:1) to give 29 (450 mg, 34%) as a white solid. $^1$H NMR (500 MHz, CDCl$_3$): δ: 9.89 (1H, s, CHO), 7.55 (1H, s, ArH), 7.30 (1H, d, J=6.95 Hz, ArH), 7.24 (1H, t, J=7.85, ArH), 6.97 (1H, d, J=6.90 Hz), 4.02 (3H, s, OCH$_3$).

2-(bromomethyl)-7-methoxybenzofuran (30)

Compound 29 (450 mg, 2.56 mmol) was dissolved in EtOH (10 mL). NaBH$_4$ (104 mg, 2.81 mmol) was added portionwise at 0° C., with vigorous stirring. The suspension was stirred at 0° C. for 15 min and then at room temperature for 1.5 h. Solvent was evaporated off in-vacuo. The resulting crude alcohol residue was dissolved in toluene (5 mL) and the solution was cooled to 0° C. PBr$_3$ (240 µL, 2.56 mmol) was added dropwise over 10 min.

The reaction mixture was then brought up to room temperature and stirred for 1 h. The solvent was evaporated off in-vacuo. The residue was adsorbed on silica gel and purified by flash chromatography, eluting with hexane/EtOAc (4:1) to give 30 (150 mg, 24%) as an oil. $^1$H NMR (500 MHz, CDCl$_3$): δ: 7.19-7.17 (2H, m, ArH), 6.85 (1H, d, J=5.60, ArH), 6.78 (1H, s, ArH), 4.62 (2H, s, 2-CH$_2$), 4.04 (3H, s, OCH$_3$).

7-((7-methoxybenzofuran-2-yl)methoxy)-4-methyl-2H-chromen-2-one (31) VG029-05

Sodium ethoxide (12 mg, 0.18 mmol) was added to DMF (5 mL) at 0° C., and the suspension was stirred for 10 min. 7-hydroxy-4-methylcoumarin (32 mg, 0.17 mmol) was slowly added and resulting mixture was stirred at this temp for 0.5 h. To this mixture 30 (40 mg, 0.17 mmol) was added portionwise. Resulting reaction mixture was stirred at room temperature for 2 h. DMF was evaporated off in-vacuo and the residue was purified by flash chromatography, eluting with hexane:EtOAc (3:1) to give 31 (14 mg, 25%) as a white solid m/z 337.04 (M+H), 673.13 (2M+H).

7-((5-bromobenzofuran-2-yl)methoxy)-4-methyl-2H-chromen-2-one (32) VG035-04

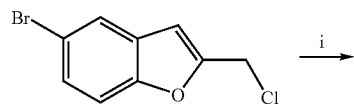

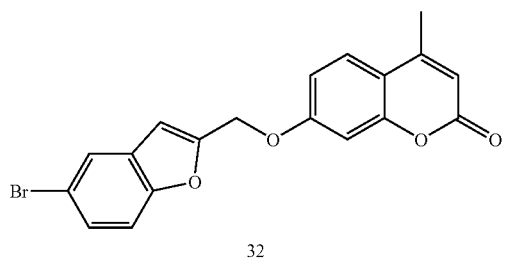

32

VG035-04

Reagents and conditions: (i) ) Sodium ethoxide, 7-hydroxy-4-methylcoumarin, DMF 7-((5-bromobenzofuran-2-yl)methoxy)-4-methyl-2H-chromen-2-one (VG035-04)

Sodium ethoxide (76 mg, 1.10 mmol) was added to DMF (10 mL) at 0° C., and the suspension was stirred for 10 min. 7-hydroxy-4-methylcoumarin (215 mg, 1.22 mmol) was slowly added and resulting mixture was stirred at this temp for 0.5 h. To this mixture 5-bromo-2-(chloromethyl)benzofuran (250 mg, 1.02 mmol) was added portionwise. Resulting reaction mixture was stirred at room temperature for 2 h. DMF was evaporated off in-vacuo and the residue was purified by flash chromatography, eluting with hexane: EtOAc (3:1) to give 32 (120 mg, 31%) as a white solid. m/z 386 (M+H). H$^1$ NMR (500 MHz, DMSO-d$_6$): δ=7.91 (1H, d, J=2.0 Hz, ArH), 7.71 (1H, d, J=8.80 Hz, ArH), 7.61 (1H, d, J=8.75, ArH), 7.49 (1H, dd, J=6.70 & 2.05 Hz, ArH), 7.20 (1H, d, J=2.45 Hz, ArH), 7.13 (1H, s, ArH), 7.09 (1H, dd, J=6.30 & 2.50, ArH), 6.25 (1H, s, CH), 5.43 (2H, s, CH$_2$), 2.41 (3H, s, CH$_3$). $^{13}$C NMR CDEPT 135, (500 MHz, CDCl$_3$): δ: 127.55 (ArCH), 126.59 (ArCH), 124.04 (ArCH), 113.32 (ArCH), 112.56 (ArCH), 111.44 (ArCH), 106.87 (ArCH), 101.66 (ArCH), 62.40 (CH$_2$), 16.11 (CH$_3$).

7-((5-chlorobenzofuran-2-yl)methoxy)-4-methyl-2H-chromen-2-one (36) VG028-05

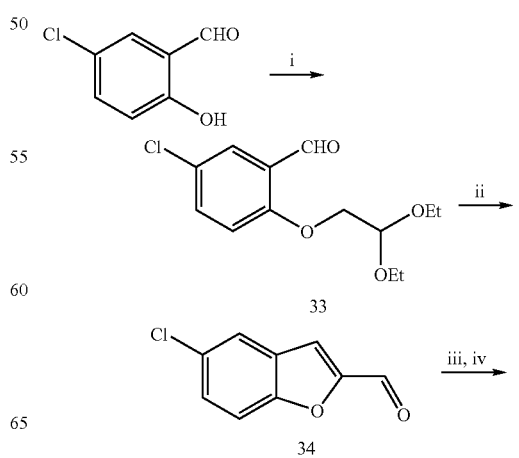

-continued

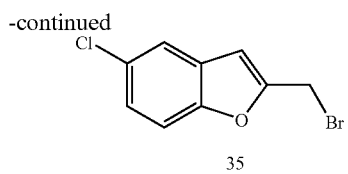
35 v↓

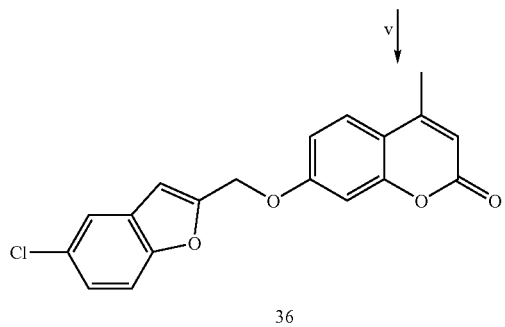
36
VG028-05

Reagents and conditions: (i) BrCH$_2$CH(OEt)$_2$, DMF, 140° C.; (ii) CH$_3$CO$_2$H, 120° C., 24 h; (iii) NaBH$_4$, THF, EtOH, rt (iv) PBr$_3$, pyridine, toluene, rt; (v) Sodium ethoxide, 7-hydroxy-4-methylcoumarin, DMF, rt 5-chloro-2-(2,2-diethoxyethoxy)benzaldehyde (33)

To a stirred suspension of 5-chloro-2-hydroxybenzaldehyde (5.0 g, 32.1 mmol) and K$_2$CO$_3$ (4.87 g, 35.3 mmol) in DMF (20 mL), bromoacetaldehyde diethyl acetal (5.43 mL, 35.3 mmol) was added dropwise. The mixture was refluxed for 4 h. After cooling, the precipitate was filtered off and the solvent was evaporated in vacuo. The crude residue was adsorbed on silica gel and purified by flash chromatography. The product was eluted with hexane/EtOAc (4:1) to give 33 (4.10 g, 38%) as an oil. $^1$H NMR (500 MHz, CDCl$_3$): δ: 10.42 (1H, s, CHO), 7.76 (1H, d, J=2.8 Hz, ArH), 7.46 (1H, dd, J=6.15 & 2.75 Hz, ArH), 6.96 (1H, d, J=8.90 Hz, ArH), 4.87 (1H, t, J=5.25 Hz, CH), 4.10 (2H, d, J=5.25 Hz, CH$_2$), 3.80-3.77 (2H, m, CH$_2$CH$_3$), 3.67-3.62 (2H, m, CH$_2$CH$_3$), 1.24 (6H, t, J=7.05 Hz, 2×CH$_3$).

5-chlorobenzofuran-2-carbaldehyde (34)

A stirred solution of 33 (4.10 g, 15.07 mmol) in acetic acid (20 mL) was refluxed for 24 h. After cooling, the solution was evaporated to dryness. The crude product was adsorbed on silica gel and purified by flash chromatography, eluting with hexane/EtOAc (4:1) to give 34 (550 mg, 20%) as a white solid. $^1$H NMR (500 MHz, CDCl$_3$): δ: 9.91 (1H, s, CHO), 7.76 (1H, d, J=1.85 Hz, ArH), 7.57 (1H, d, J=8.90 Hz, ArH), 7.53 (1H, s, ArH), 7.50 (1H, dd, J=8.90 & 2.10 Hz, ArH).

2-(bromomethyl)-5-chlorobenzofuran (35)

Compound 34 (160 mg, 0.89 mmol) was dissolved in EtOH (5 mL). NaBH$_4$ (36 mg, 0.98 mmol) was added portionwise at 0° C., with vigorous stirring. The suspension was stirred at 0° C. for 15 min and then at room temperature for 1.5 h. Solvent was evaporated off in-vacuo. The resulting crude alcohol residue was dissolved in toluene (5 mL) and the solution was cooled to 0° C. PBr$_3$ (92 μL, 0.98 mmol) was added dropwise over 10 min. The mixture was then brought up to room temperature and stirred for 1 h. The solvent was evaporated off in-vacuo. The residue was adsorbed on silica gel and purified by flash chromatography, eluting with hexane/EtOAc (4:1) to give 35 (128 mg, 57%) as an oil. $^1$H NMR (500 MHz, CDCl$_3$): δ: 7.48 (1H, d, J=2.05 Hz, ArH), 7.37 (1H, d, J=8.70 Hz, ArH), 7.25 (1H, dd, J=8.80 & 2.05 Hz ArH), 6.68 (1H, s, ArH), 4.55 (2H, s, 2-CH$_2$).

7-((5-chlorobenzofuran-2-yl)methoxy)-4-methyl-2H-chromen-2-one (36) VG028-05

Sodium ethoxide (60 mg, 0.24 mmol) was added to DMF (5 mL) at 0° C., and the suspension was stirred for 10 min. 7-hydroxy-4-methylcoumarin (47 mg, 0.27 mmol) was slowly added and resulting mixture was stirred at this temp for 0.5 h. To this mixture 2-(bromomethyl)-5-methoxybenzofuran (40 mg, 0.17 mmol) was added portionwise. Resulting reaction mixture was stirred at room temperature for 2 h. DMF was evaporated off in-vacuo and the residue was purified by flash chromatography, eluting with hexane: EtOAc (3:1) to give the target compound as a white solid (2.7 mg, 3%). m/z 341.10 (M+H).

7-((5,7-dimethoxybenzofuran-2-yl)methoxy)-4-methyl-2H-chromen-2-one (42) VG035-05

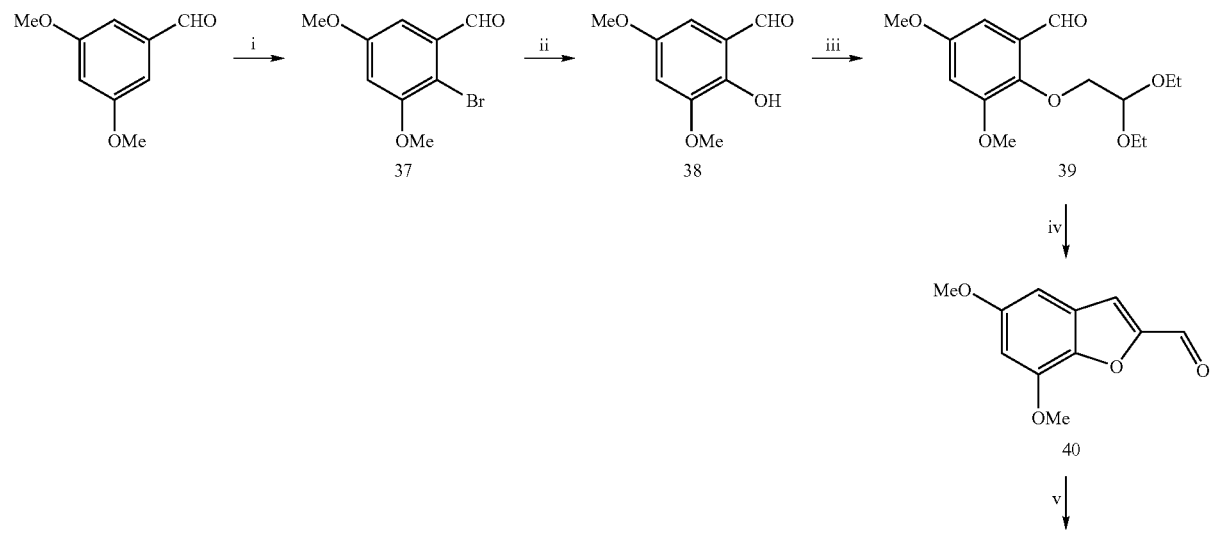

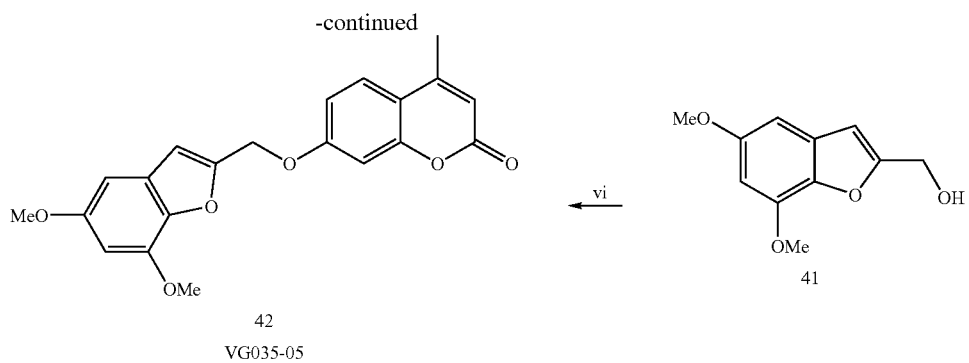

-continued

42

VG035-05

Reagents and conditions: (i) Br₂, CH₃CO₂H; (ii) (a) morpholine, THF, -50° C., 15 min; (b) n-BuLi, -75° C., 35 min; (c) PhNO₂, -75° C., 4 h, H₃O⁺, 15 min;
(iii) BrCH₂CH(OEt)₂, DMF, 140° C.; (iv) CH₃CO₂H, 120° C., 24 h; (v) NaBH₄, THF, EtOH, rt

2-Bromo-3,5-dimethoxybenzaldehyde (37)

3,5-dimethoxybenzaldehyde (12.6 g, 76 mmol) was dissolved in acetic acid (350 mL). The resulting colourless solution was cooled to 0° C. A solution of bromine (3.9 mL) in acetic acid (50 mL) was added dropwise over 1 h. Once the addition was complete the ice bath was removed and the resulting pale green solution was stirred overnight at room temperature. Cold water was added to the solution. The resulting white solid was collected by vacuum filtration and rinsed with water. The solid was then redissolved in EtOAc and adsorbed on silica gel. The product was purified by flash chromatography, eluting with hexane/EtOAc (4:1) to give 37 (12.5 g, 66%) as a white solid. m/z=344.98 (M+H). $^1$H NMR (500 MHz, CDCl₃): δ: 10.43 (1H, s, CHO), 7.06 (1H, s, ArH), 6.73 (1H, s, ArH), 3.93 (3H, s, CH₃O), 3.86 (3H, s, CH₃O). $^{13}$C NMR (500 MHz, CDCl₃): δ: 192.09 (CHO), 159.92 (C-5), 157.02 (C-3), 134.67 (C-1), 109.12 (C-2), 105.83, 103.37 (C-4 & C-6), 56.60 (OMe), 55.82 (OMe).

2-Hydroxy-3,5-dimethoxybenzaldehyde (38)

Morpholine (2.05 g, 24 mmol) and THF (40 mL) were placed in a dry, three-necked, round bottomed flask equipped with a stirring bar, septum cap, dropping funnel, thermometer, and argon inlet. The flask was cooled in a dry ice-acetone bath to -50° C., and a solution of n-BuLi in hexane (1.6M, 15 mL, 24 mmol) was added all at once. After 10 min a solution of the 2-bromo-3,5-dimethoxybenzaldehyde 37 (4.9 g, 20 mmol) in THF (30 mL) was added dropwise via a syringe over a period of 4 min, and the mixture was cooled to ~-75° C. over 20 min. n-BuLi in hexane (1.6M, 20 mL, 32 mmol) was then added dropwise over 45 min, keeping the temperature at -75° C. After complete addition of n-BuLi the solution was stritted for 35 min. A solution of nitrophenol (6.90 g, 46 mmol) in 10 mL THF was added from the dropping funnel, keeping the temperature at -75° C. The resulting dark mixture was stirred at -75° C. for 4 h and then allowed to warm to room temperature. It was acidified to pH 1 with 6N HCl and stirred for 15 min. After dilution with brine (100 mL), THF was removed in-vacuo. The aqueous solution was extracted with diethyl ether (4×40 mL). The combined organic layers were extracted with 2 N NaOH (3×40 mL). The combined NaOH extracts were washed with diethyl ether (3×20 mL) and then acidified to pH 1 with concentrated HCl. The resulting mixture was extracted with CH₂Cl₂ (3×20 mL), and the combined organic extracts were washed with brine, dried (MgSO₄) and adsorbed on silica gel. The product was purified by flash chromatography, eluting with EtOAc/hexane (1:2) to give 38 (2.0 g, 55%) as a yellow solid. m/z=183.06 (M+H). $^1$H NMR (500 MHz, CDCl₃): δ: 10.71 (1H, s, OH), 9.91 (1H, s, CHO), 6.77 (1H, d, $J_{4,6}$=2.8 Hz, H-6), 6.61 (1H, d, $J_{4,6}$=2.8 Hz, H-4), 3.92 (3H, s, OMe), 3.84 (3H, s, OMe). $^{13}$C NMR CDEPT 135 (500 MHz, CDCl₃): δ: 196.11 (CHO), 107.93 (C-6), 103.90 (C-4), 56.29 (OMe), 55.83 (OMe).

2-(2,2-Diethoxyethoxy)-3,5-dimethoxybenzaldehyde (39)

To a stirred suspension containing 38 (1.1 g, 6.0 mmol) and K₂CO₃ (1.0 g, 7.2 mmol) in DMF (100 mL), bromoacetaldehyde diethyl acetal (0.93 mL, 6.0 mmol) was added dropwise. The mixture was refluxed for 4 h. After cooling, the precipitate was filtered off and the solvent was evaporated in vacuo. The crude residue was adsorbed on silica gel and purified by flash chromatography. The product was eluted with hexane/EtOAc (4:1) to give 39 (1.2 g, 67%) as an oil. $^1$H NMR (500 MHz, CDCl₃): δ: 10.50 (1H, s, CHO), 6.88 (1H, d, $J_{4,6}$=2.9 Hz, H-6), 6.74 (1H, d, $J_{4,6}$=2.9 Hz, H-4), 4.83 (1H, t, $J_{4,6}$=5.3 Hz, CH), 4.14 (2H, d, $J_{4,6}$=5.3 Hz, CH₂), 3.88 (3H, s, OMe), 3.83 (3H, s, OMe), 3.77-3.71 (2H, m, CH₂CH₃), 3.63-3.58 (2H, m, CH₂CH₃), 1.24 (6H, t, J=7.1 Hz, 2×CH₃).

5,7-dimethoxybenzofuran-2-carbaldehyde (40)

A stirred solution of 39 (1.2 g, 4.0 mmol) in acetic acid (35 mL) was refluxed for 16 h. After cooling, the solution was evaporated to dryness. The crude product was adsorbed on silica gel and purified by flash chromatography, eluting with hexane/EtOAc (2:1) to give 40 (230 mg, 28%) as a white solid. $^1$H NMR (500 MHz, CDCl₃): δ: 9.89 (1H, s, CHO), 7.50 (1H, s, H-3), 6.69 (1H, d, $J_{4,6}$=2.2 Hz, H-6), 6.64 (1H, d, $J_{4,6}$=2.2 Hz, H-4), 4.01 (3H, s, OMe), 3.87 (3H, s, OMe). $^{13}$C NMR CDEPT 135, (500 MHz, CDCl₃): δ: 179.91 (CHO), 153.37 (C-2), 116.10 (C-3), 101.80 (C-6), 94.90 (C-4), 56.20 (OMe), 55.88 (OMe).

(5,7-dimethoxybenzofuran-2-yl)methanol (41)

Compound 39 (460 mg, 2.23 mmol) was dissolved in THF (5 mL) and EtOH (1 mL). NaBH₄ (102 mg, 2.68 mmol) was added portionwise at 0° C., with vigorous stirring. The suspension was stirred at 0° C. for 15 min and then at room temperature for 1 h. Solvents were evaporated off in-vacuo. The crude residue was taken up in EtOAc and washed with water, brine and dried (MgSO₄). The residue was adsorbed on silica gel and purified by flash chromatography, eluting with hexane/EtOAc (1:1) to give 41 (388 mg, 82%) as a white solid. m/z=209.08 (M+H). $^1$H NMR (500 MHz, CDCl$_3$): δ: 6.62 (1H, s, H-3), 6.60 (1H, s, H-6), 6.46 (1H, s, H-4), 4.76 (2H, s, 2-CH$_2$), 3.99 (3H, s, OMe), 3.85 (3H, s, OMe). $^{13}$C NMR (500 MHz, CDCl$_3$): δ: 157.23 (C-5), 156.72 (C-1), 145.36 (C-7), 139.50 (C1a), 129.38 (C4a), 104.62 (C-3), 96.96 (C-6), 94.58 (C-4), 57.98 (2-CH$_2$), 55.95 (OMe), 55.83 (OMe).

7-((5,7-dimethoxybenzofuran-2-yl)methoxy)-4-methyl-2H-chromen-2-one (42) VG035-05

Compound 41 (130 mg, 0.63 mmol) was dissolved in toluene (5 mL) and the solution was cooled to 0° C. PBr$_3$ (64 µL, 0.69 mmol) was added dropwise over 10 min. The reaction mixture was then brought up to room temperature and stirred for 1 h. The solvent was evaporated off in-vacuo. The crude residue was used in the next step. Sodium ethoxide (80 mg, 0.24 mmol) was added to DMF (5 mL) at 0° C., and the suspension was stirred for 10 min. 7-hydroxy-4-methylcoumarin (47 mg, 0.27 mmol) was slowly added and resulting mixture was stirred at this temp for 0.5 h. To this mixture 2-(bromomethyl)-5-methoxybenzofuran (40 mg, 0.17 mmol) was added portionwise. Resulting reaction mixture was stirred at room temperature for 2 h. DMF was evaporated off in-vacuo and the residue was purified by flash chromatography, eluting with hexane:EtOAc (3:1) to give 42 (2.7 mg, 3%) as a white solid. m/z=367.05 (M+H), 733.15 (2M+H).

4-methyl-7-(naphthalene-1-ylmethoxy)-2H-chromen-2-one (43) TLE-M1-SU001A

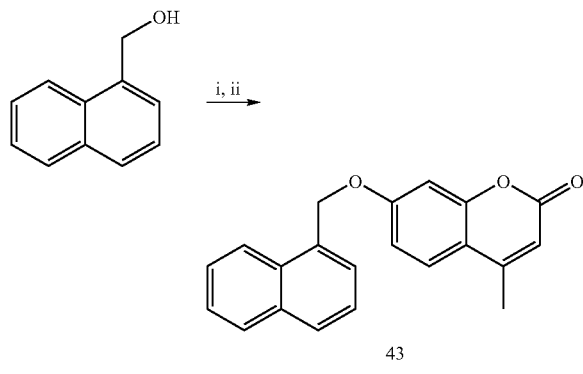

43
TLE-M1-SU001A
Reagents and conditions: (i) PBr$_3$, pyridine, toluene; (ii) Sodium ethoxide, 7-hydroxy-4-methylcoumarin, DMF 1-Naphthalene methanol (2.0 g, 12.7 mmol) was dissolved in toluene (30 mL) and pyridine (1.02 mL, 12.7 mmol) was added. The solution was cooled to 0° C. PBr$_3$ (1.19 mL, 12.7 mmol) was added dropwise over 15 min. The reaction mixture was then brought up to room temperature and stirred for 1 h. The mixture was washed with K$_2$CO$_3$ solution and extracted with EtOAc (3×30 mL). The EtOAc layer was washed with brine and dried (MgSO$_4$). The solvent was evaporated off in-vacuo to give 1-(bromomethyl)naphthalene (1.5 g, 53%) as a colourless oil, This intermediate was used in the following reaction. Sodium ethoxide (169 mg, 2.49 mmol) was added to DMF (5 mL) at 0° C., and the suspension was stirred for 10 min. 7-hydroxy-4-methylcoumarin (438 mg, 2.49 mmol) was slowly added and resulting mixture was stirred at this temp for 0.5 h, then allowed to reach room temperature. To this mixture 1-(bromomethyl)naphthalene (500 mg, 2.26 mmol) was added portionwise. Resulting reaction mixture was stirred at room temperature for 16 h. DMF was evaporated off in-vacuo and the residue was taken up in EtOAc, and washed with brine (2×50 mL), water (2×50 mL) and 1M NaOH (2×30 mL). The organic layer was dried (MgSO$_4$) and product was purified by flash chromatography, eluting with hexane:EtOAc (2:1) to give 43 (200 mg, 28%) as a white solid. Mpt=181-183° C. H$^1$ NMR (500 MHz, acetone-d$_6$): δ=8.10 (1H, d, ArH), 8.00-7.99 (2H, m, Ar), 7.97-7.71 (2H, m, ArH), 7.70-7.53 (3H, m, ArH), 7.24 (1H, s, ArH), 7.09 (1H, d, CH), 6.23 (1H, s, CH), 5.68 (2H, s, CH$_2$), 2.40 (3H, s, CH$_3$).

4-methyl-7-(naphthalen-2-ylmethoxy)-2H-chromen-2-one (44) VG040-03

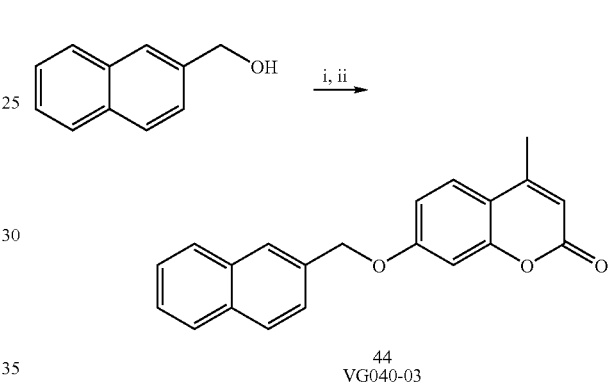

44
VG040-03
Reagents and conditions: (i) PBr$_3$, pyridine, toluene; (ii) Sodium ethoxide, 7-hydroxy-4-methylcoumarin, DMF Naphthalen-2-ylmethanol (2.0 g, 12.7 mmol) was dissolved in toluene (30 mL) and pyridine (1.02 mL, 12.7 mmol) was added. The solution was cooled to 0° C. PBr$_3$ (1.19 mL, 12.7 mmol) was added dropwise over 15 min. The mixture was then brought up to room temperature and stirred for 1 h. The mixture was washed with K$_2$CO$_3$ solution and extracted with EtOAc (3×30 mL). The EtOAc layer was washed with brine and dried (MgSO$_4$). The solvent was evaporated off in-vacuo to give crude 1-(bromomethyl)naphthalene. This intermediate was used in the following reactions. Sodium ethoxide (169 mg, 2.49 mmol) was added to DMF (5 mL) at 0° C., and the suspension was stirred for 10 min. 7-hydroxy-4-methylcoumarin (438 mg, 2.49 mmol) was slowly added and resulting mixture was stirred at this temp for 0.5 h, then allowed to reach room temp. To this mixture 1-(bromomethyl)naphthalene (500 mg, 2.26 mmol) was added portionwise. Resulting reaction mixture was stirred at room temperature for 16 h. DMF was evaporated off in-vacuo and the residue was taken up in EtOAc, and washed with brine (2×50 mL), water (2×50 mL) and 1M NaOH (2×30 mL). The organic layer was dried (MgSO$_4$) and product was purified by flash chromatography, eluting with hexane:EtOAc (2:1) to give 44 (1.44 g, 36%) as a white solid. m/z=317.12 (M+H), 633.24 (2M+H). H$^1$ NMR (500 MHz, CDCl$_3$): δ=7.93-7.87 (4H, m, ArH), 7.58-7.52 (4H, m, Ar), 6.97 (1H, t, J=2.43 Hz, ArH), 6.16 (1H, s, ArH), 5.32 (2H, s, CH$_2$), 2.41 (3H, s, CH$_3$).

7-(benzhydryloxy)-4-methyl-2H-chromen-2-one (45) TLE-M1-SU004A

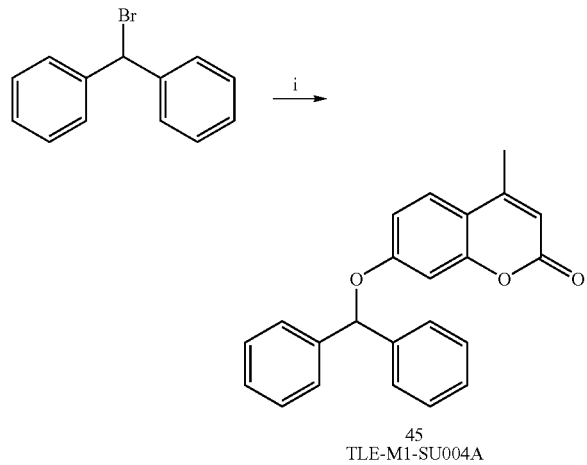

45
TLE-M1-SU004A

Reagents and conditions: (i) Sodium ethoxide, 7-hydroxy-4-methylcoumarin, DMF

Sodium ethoxide (165 mg, 2.43 mmol) was added to DMF at 0° C., and the suspension was stirred for 10 min. 7-hydroxy-4-methylcoumarin (428 mg, 2.43 mmol) was slowly added and resulting mixture was stirred at this temp for 0.5 h, then allowed to reach room temp. To this mixture diphenylmethyl bromide (500 mg, 2.02 mmol) was added portionwise. Resulting reaction mixture was stirred at room temperature for 16 h. DMF was evaporated off in-vacuo and the residue was taken up in EtOAc, and washed with brine (2×30 mL), water (2×30 mL) and 1M NaOH (2×30 mL). The organic layer was dried (MgSO$_4$) and product was purified by flash chromatography, eluting with hexane: EtOAc (2:1) to give 45 (200 mg, 29%) as a white solid. Mpt=146-148° C. H$^1$ NMR (500 MHz, DMSO-d$_6$): δ=7.63 (1H, d, ArH), 7.53 (4H, d, ArH), 7.38 (4H, t, ArH), 7.29 (2H, t, ArH), 7.09 (2H, d, ArH), 7.04 (1H, d, ArH), 6.75 (1H, s, ArH), 6.18 (1H, s, CH), 2.37 (3H, s, CH$_3$). $^{13}$C NMR (500 MHz, DMSO-d$_6$, DEPT 135): δ=160.2, 154.4, 153.2, 140.8, 129.90, 128.0, 126.8, 113.7, 111.4, 111.2, 102.9, 80.2, 18.2.

4-methyl-7-(1-(naphthalen-2-yl)ethoxy)-2H-chromen-2-one (46) VG039-03

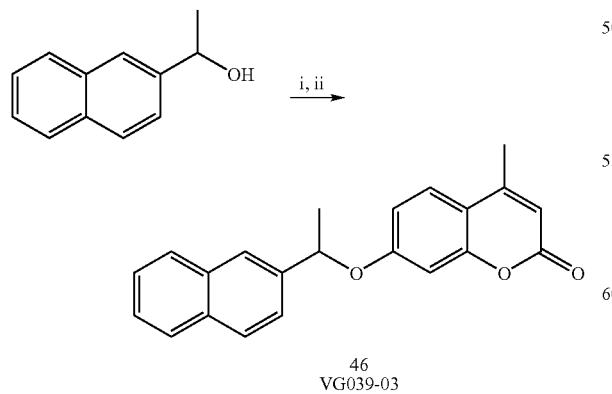

46
VG039-03

Reagents and conditions: (i) PBr$_3$, pyridine, toluene; (ii) Sodium ethoxide, 7-hydroxy-4-methylcoumarin, DMF 1-(Naphthalen-2-yl)ethanol (2.0 g, 11.6 mmol) was dissolved in toluene (30 mL). The solution was cooled to 0° C. PBr$_3$ (1.09 mL, 11.6 mmol) was added dropwise over 15 min. The reaction mixture was then brought up to room temperature and stirred for 1 h. The mixture was washed with K$_2$CO$_3$ solution and extracted with EtOAc (3×30 mL). The EtOAc layer was washed with brine and dried (MgSO$_4$). The solvent was evaporated off in-vacuo to give crude 2-(1-bromoethyl) naphthalene. This intermediate was used in the following step.

Sodium ethoxide (63.4 mg, 0.93 mmol) was added to DMF (5 mL) at 0° C., and the suspension was stirred for 10 min. 7-hydroxy-4-methylcoumarin (147 mg, 0.84 mmol) was slowly added and resulting mixture was stirred at this temperature for 0.5 h, then allowed to reach room temperature. To this mixture 2-(1-bromoethyl)naphthalene (200 mg, 0.85 mmol) was added portionwise. Resulting reaction mixture was stirred at room temperature for 16 h. DMF was evaporated off in-vacuo and the residue was taken up in EtOAc, and washed with brine (2×50 mL), water (2×50 mL) and 1M NaOH (2×30 mL). The organic layer was dried (MgSO$_4$) and product was purified by flash chromatography, eluting with hexane:EtOAc (2:1) to give 46 (60 mg, 21%) as a white solid. m/z=331.15 (M+H), 661.29 (2M+H). H$^1$ NMR (500 MHz, DMSO-d$_6$): δ=7.97 (1H, s, ArH), 7.93-7.86 (3H, m, ArH), 7.60-7.50 (4H, m, Ar), 6.99 (1H, q, J=6.45 & 2.35 Hz, ArH), 6.96 (1H, d, J=2.40 Hz, ArH), 6.13 (1H, s, ArH), 5.84 (1H, q, J=6.35 Hz, CH), 2.26 (3H, s, CH$_3$), 1.67 (3H, d, J=6.35 Hz, CH$_3$).

7-(anthracen-9-ylmethoxy)-4-methyl-2H-chromen-2-one (48) SU06-02

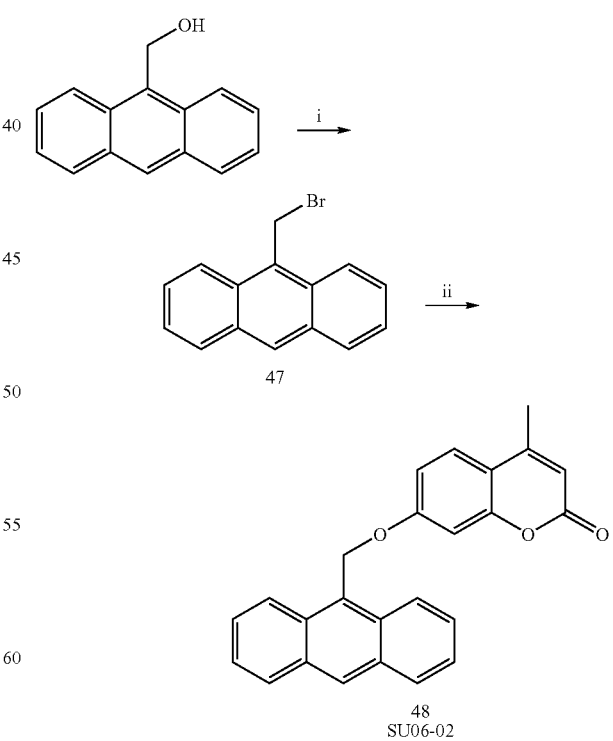

48
SU06-02

Reagents and conditions: (i) PBr$_3$, pyridine, toluene; (ii) Sodium ethoxide, 7-hydroxy-4-methylcoumarin, DMF

9-(bromomethyl)anthracene (47)

To a stirring suspension of 9-anthracenemethanol (2.0 g, 9.6 mmol) at 0° C. in toluene (100 ml) was added PBr$_3$ (1.2 mL, 12.51 mmol) and the suspension was stirred at 0° C. for 1 h. The reaction mixture was then brought up to room temperature and let to stir for further 1 h. The mixture turned into a yellow solution. K$_2$CO$_3$ (10 mL) was added to quench the reaction. Toluene was evaporated off in-vacuo. The residue was taken up in EtOAc and washed with saturated aqueous K$_2$CO$_3$, water and brine and dried (MgSO$_4$). The solvent was evaporated off in-vacuo and the crude residue was purified by flash chromatography, eluting with hexane:EtOAc (2:1) to give 47 (1.4 g, 54%) as yellow solid. H$^1$ NMR (500 MHz, CDCl$_3$): δ=8.45 (1H, s, Ar-10H), 8.27 (2H, d, Ar-1, 8H), 8.00 (2H, d, Ar-4, 6H), 7.62 (2H, d, Ar-2, 7H), 7.48 (2H, d, Ar-3, H), 5.50 (2H, s, CH$_2$).

7-(anthracen-9-ylmethoxy)-4-methyl-2H-chromen-2-one (48) SU06-02

Sodium ethoxide (151 mg, 2.21 mmol) was added to DMF (5 mL) at 0° C., and the suspension was stirred for 10 min. 7-hydroxy-4-methylcoumarin (390 mg, 2.21 mmol) was slowly added and resulting mixture was stirred at this temp for 0.5 h, then allowed to reach room temp. To this mixture 47 (500 mg, 1.85 mmol) was added portionwise. Resulting reaction mixture was stirred at room temperature for 16 h. DMF was evaporated off in-vacuo and the residue was taken up in EtOAc, and washed with brine, water and 1M NaOH (2×30 mL). The organic layer was dried (MgSO$_4$) and product was purified by flash chromatography, eluting with hexane:E-tOAc (2:1) to give 48 (200 mg, 30%) as a yellow solid. Mpt=216-218° C. H$^1$ NMR (500 MHz, DMSO-d$_6$): δ=8.10 (1H, d, ArH), 8.00-7.99 (2H, m, Ar), 7.97-7.71 (2H, m, ArH), 7.70-7.53 (3H, m, ArH), 7.24 (1H, s, ArH), 7.09 (1H, d, CH), 6.23 (1H, s, CH), 5.68 (2H, s, CH$_2$), 2.40 (3H, s, CH$_3$). $^{13}$C NMR (500 MHz, DMSO-d$_6$, DEPT 135): δ=160.8 (qC), 152.0 (2×qC), 129.0 (2×CH), 128.9 (2×CH), 126.8, (2×CH), 126.8 (Ar CH), 126.5 (Ar CH), 125.3 (Ar CH), 124.1 (Ar CH), 112.9 (coumarin 3-CH), 111.2 (coumarin 6-CH), 101.7 (coumarin 8-CH), 62.9 (CH$_2$), 18.2 (CH$_3$).

7-(bis(4-methoxyphenyl)methoxy)-4-methyl-2H-chromen-2-one (49) SU010-02

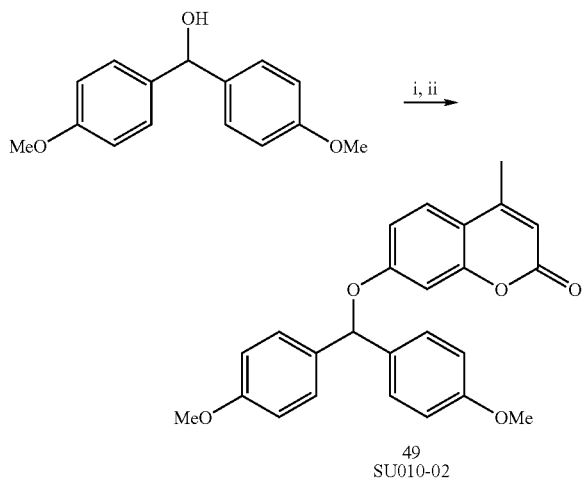

49
SU010-02
Reagents and conditions: (i) PBr$_3$, pyridine, toluene; (ii) Sodium ethoxide, 7-hydroxy-4-methylcoumarin, DMF Bis(4-methoxyphenyl)methanol (2.0 g, 8.2 mmol) was dissolved in toluene (60 mL) and pyridine (661 μL, 8.2 mmol)) was added. The solution was cooled to 0° C. PBr$_3$ (768 μL, 8.2 mmol) was added dropwise over 15 min. The reaction mixture was warmed to room temperature and stirred for 1 h. The mixture was washed with K$_2$CO$_3$ solution and extracted with EtOAc (3×30 mL). The EtOAc layer was washed with brine and dried (MgSO$_4$). The solvent was evaporated off in-vacuo to give the crude product 4,4'-(bromomethylene)bis(methoxybenzene) (780 mg, 31%), as a colourless oil. This was used in the next reaction step without further purification. Sodium ethoxide (133 mg, 1.96 mmol) was added to DMF (5 mL) at 0° C., and the suspension was stirred for 10 min. 7-hydroxy-4-methylcoumarin (345 mg, 1.96 mmol) was slowly added and resulting mixture was stirred at this temp for 0.5 h. To this mixture 4,4'-(bromomethylene)bis(methoxybenzene (500 mg, 1.63 mmol) was added portionwise. Resulting reaction mixture was stirred at room temperature for 16 h. DMF was evaporated off in-vacuo and the residue was taken up in EtOAc, and washed with brine, water and 1M NaOH (2×30 mL). The organic layer was dried (MgSO$_4$) and product was purified by flash chromatography, eluting with hexane:EtOAc (2:1) to give 49 (100 mg, 15%) as a white solid. Mpt=142-145° C. m/z=403 (M+H). H$^1$ NMR (500 MHz, acetone-d$_6$): δ=7.60 (1H, d, ArH), 7.45 (4H, d, ArH), 7.04 (1H, d, ArH), 6.94 (5H, d, ArH), 6.56 (1H, s ArH), 6.10 (1H, s, qCH), 3.78 (6H, s, 2×CH$_3$O), 2.39 (3H, s, CH$_3$). $^{13}$C NMR (500 MHz, acetone-d$_6$, DEPT 135): δ=206.3 (qC), 134.1 (2×qC), 129.3 (2×CH), 129.2 (2×CH), 129.0, (2×CH), 126.9 (Ar CH), 114.4 (Ar CH), 114.7 (Ar CH), 115.1 (Ar CH), 112.5 (Ar CH), 104.0 (Ar CH), 81.7 (CH), 55.6 (2×CH$_3$), 18.2 (CH$_3$).

7-((1H-benzo[d]imidazol-2-yl)methoxy)-4-methyl-2H-chromen-2-one (50) VG033-03

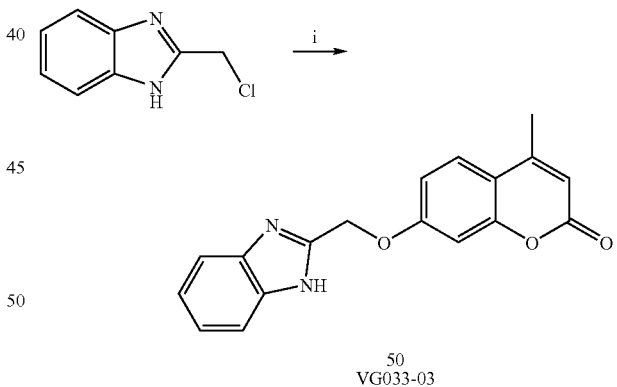

50
VG033-03
Reagents and conditions: (i) Sodium ethoxide, 7-hydroxy-4-methylcoumarin, DMF Sodium ethoxide (82 mg, 1.20 mmol) was added to DMF (10 mL) at 0° C., and the suspension was stirred for 10 min. 7-hydroxy-4-methylcoumarin (253 mg, 1.44 mmol) was slowly added and resulting mixture was stirred at this temp for 0.5 h. To this mixture 2-(chloromethyl)-1H-benzo[d]imidazole (200 mg, 1.20 mmol) was added portionwise. Resulting reaction mixture was stirred at room temp for 2 h. DMF was evaporated off in-vacuo and the residue was purified by flash chromatography, eluting with hexane:EtOAc (3:1) to give 50 (200 mg, 54%) as a white solid. m/z=307.11 (M+H), 613.22 (2M+H). H$^1$ NMR (500 MHz, DMSO-d$_6$): δ=12.75

(1H, brs, NH), 7.74 (1H, d, J=8.85 Hz, ArH), 7.60-7.59 (2H, m, ArH), 7.23-7.12 (4H, m, ArH), 6.25 (1H, s, ArH), 5.48 (2H, s, CH$_2$), 2.40 (3H, s, CH$_3$). $^{13}$C NMR CDEPT 135, (500 MHz, CDCl$_3$): δ: 206.52 (qC), 160.80, 160.03, 154.52, 153.33, 149.27, 126.57, 126.28, 122.04, 119.42, 113.64, 112.50, 111.47, 101.86, 101.77, 64.23, 30.67, 18.10.

7-(benzo[d]thiazol-2-ylmethoxy)-4-methyl-2H-chromen-2-one (51) VG014-04

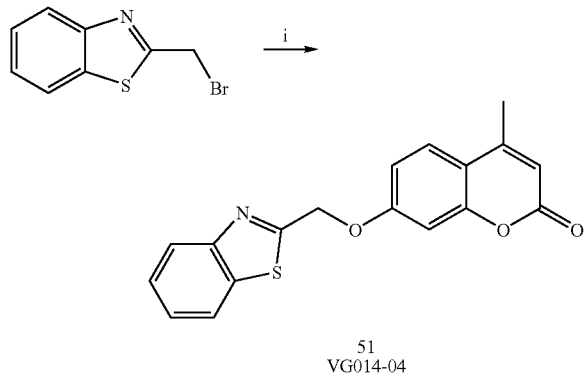

51
VG014-04

Reagents and conditions: (i) Sodium ethoxide, 7-hydroxy-4-methylcoumarin, DMF

Sodium ethoxide (30 mg, 0.44 mmol) was added to DMF (10 mL) at 0° C., and the suspension was stirred for 10 min. 7-hydroxy-4-methylcoumarin (77 mg, 0.44 mmol) was slowly added and resulting mixture was stirred at this temp for 0.5 h. To this mixture 2-(chloromethyl)-1H-benzo[d]imidazole (100 mg, 0.44 mmol) was added portionwise. Resulting reaction mixture was stirred at room temperature for 2 h. DMF was evaporated off in-vacuo and the residue was purified by flash chromatography, eluting with hexane: EtOAc (3:1) to give 51 (25 mg, 18%) as a white solid. m/z=324.06 (M+H), 647.12 (2M+H).

4-methyl-7-(4-(thiophen-2-yl)benzyloxy)-2H-chromen-2-one (52) VG015-04

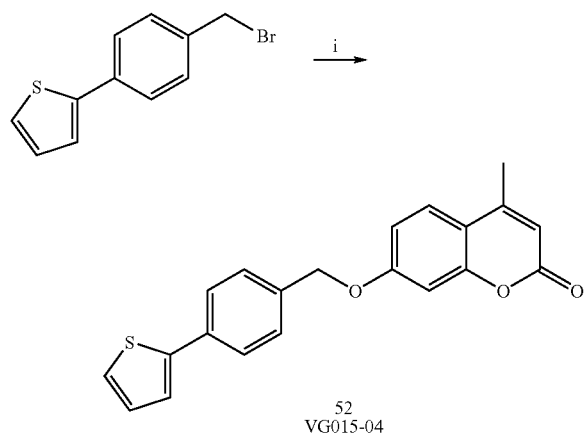

52
VG015-04

Reagents and conditions: (i) Sodium ethoxide, 7-hydroxy-4-methylcoumarin, DMF

Sodium ethoxide (27 mg, 0.40 mmol) was added to DMF (10 mL) at 0° C., and the suspension was stirred for 10 min. 7-hydroxy-4-methylcoumarin (70 mg, 0.40 mmol) was slowly added and resulting mixture was stirred at this temp for 0.5 h. To this mixture 2-(chloromethyl)-1H-benzo[d]imidazole (100 mg, 0.40 mmol) was added portionwise. Resulting reaction mixture was stirred at room temp for 2 h. DMF was evaporated off in-vacuo and the residue was purified by flash chromatography, eluting with hexane:EtOAc (3:1) to give 52 (30 mg, 18%) as a white solid. m/z=349.09 (M+H), 697.16 (2M+H).

6-(benzhydrylthio)-9H-purine (53) (VG015-02)

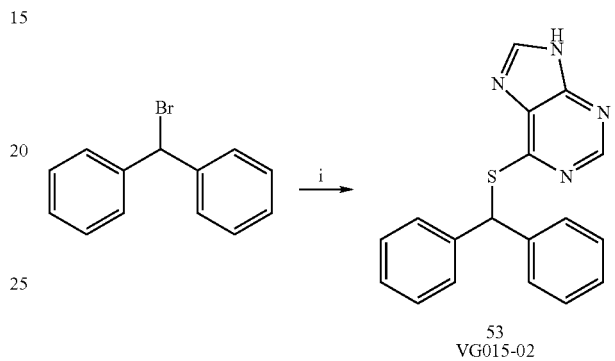

53
VG015-02

Reagents and conditions: (i) 9H-purine-6-thiol, K$_2$CO$_3$, DMF

6-Mercaptopurine (151 mg, 0.88 mmol) was dissolved in DMF (5 mL). K$_2$CO$_3$ (122 mg, 1.2 mmol) was added and to the resulting suspension, diphenyl methylbromide (200 mg, 0.8 mmol) was added. The resulting reaction mixture was stirred at room temperature for 4 h. The mixture was poured on ice and the resulting precipitate was separated by filteration, washed with ether and dried in vacuo to give 53 (35 mg, 14%) as a white solid. m/z=319 (M+H). H$^1$ NMR (500 MHz, acetone): δ=8.46 (1H, s, CH), 8.2 (1H, s, CH), 7.4 (4H, m, CH, J=3), 7.2 (4H, m, CH, J=3.83), 7.1 (2H, m, CH, J=2.12), 6.7 (1H, s, CH).

3. Carbamate-Linked Nucleoside Analogue Prodrugs

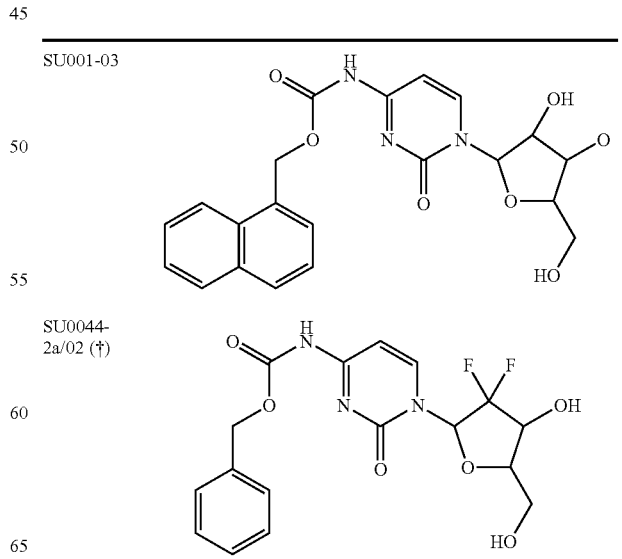

| | |
|---|---|
| SU0023/02 | 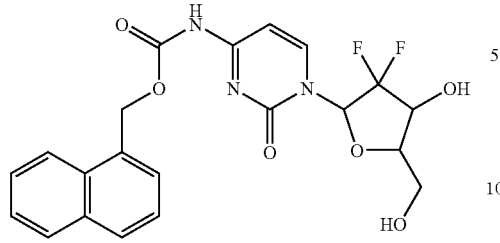 |
| SU0044-3a/02 (†) | 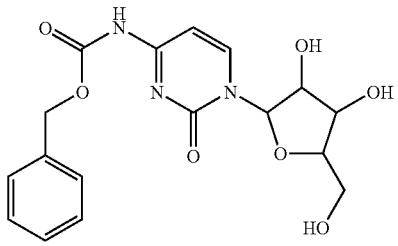 |
| SU050-03 | 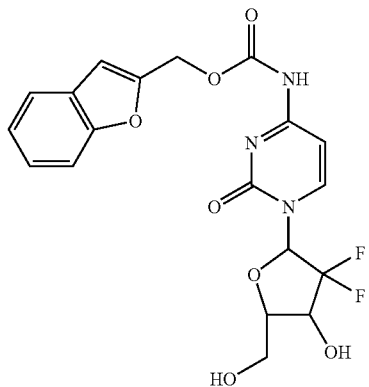 |
| SU048-04 | 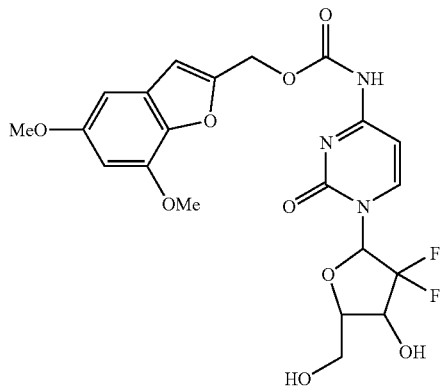 |

Naphthalen-1-ylmethyl 1-(3,4-dihydroxy-5-(hydroxymethyl)tetrahydrofuran-2-yl)-2-oxo-1,2-dihydropyrimidin-4-ylcarbamate (55) SU001-03

Reagents and conditions: (i) 20% phosgene in toluene, THF, 2 h; (ii) cytarabine·HCl, KHCO₃, DMA, 16 h Naphthalen-1-ylmethanol (3.0 g, 19.0 mmol) was added in one portion to $COCl_2$ (13.3 mL, as 20% solution of $COCl_2$ in toluene) in THF (30 mL). The reaction was stirred at room temperature for 2 h. Excess $COCl_2$ and THF was removed under reduced pressure. The solid residue was dissolved in hot hexane and filtered. The hexane was then slowly evaporated off in vacuo to obtain the chloroformate intermediate 54 as a white solid. This was used straight away in the following step. 54 (330 mg, 1.5 mmol) and KHCO₃ (252 mg, 2.52 mmol) were added to a solution of cytarabine.HCl (243 mg, 0.87 mmol) in dimethyl acetamide (5 mL), and the mixture was stirred for 16 h at room temperature. The solvent was evaporated off in vacuo and the product was purified by flash chromatography, eluting with a gradient of 2.5%-12% MeOH in DCM to obtain 55 (38 mg, 10%) as a white solid. m/z=428.15 (M+H).

Naphthalen-1-ylmethyl 1-(3,3-difluoro-4-hydroxy-5-(hydroxymethyl)tetrahydrofuran-2-yl)-2-oxo-1,2-dihydropyrimidin-4-ylcarbamate (56) SU0023-02

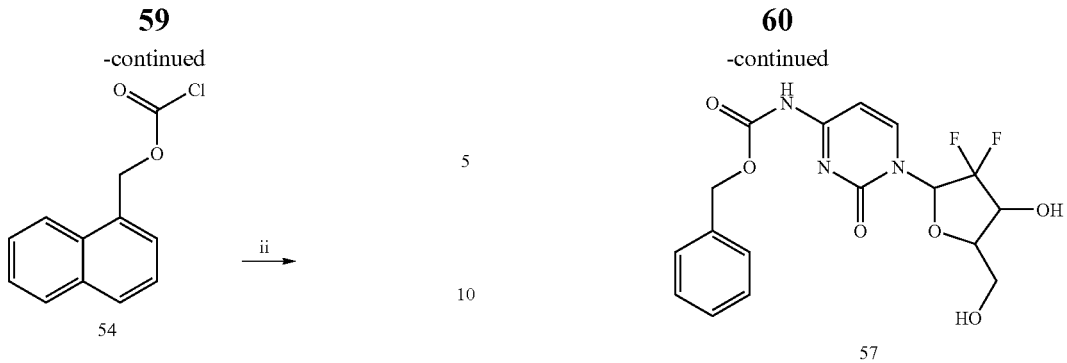

Reagents and conditions: (i) Gemcitabine•HCl, KHCO₃, H₂O, EtOAc, 80° C., 16 h

Gemcitabine.HCl (200 mg, 0.67 mmol) was dissolved in H₂O (2 mL). To this was added KHCO₃ (67 mg, 0.67 mmol) and benzyl carbonochloridate (95 μL, 0.67 mmol), predissolved in ethyl acetate (5 mL). The mixture was stirred at 80° C. for 16 h. The solvent was evaporated off in vacuo and the product was purified by flash chromatography, eluting with 3% MeOH in ethyl acetate to give 57 (40 mg, 15%) as an oil. m/z=398.12 (M+H).

Benzyl 1-(3,4-dihydroxy-5-(hydroxymethyl)tetrahydrofuran-2-yl)-2-oxo-1,2-dihydropyrimidin-4-ylcarbamate (58) SU0044-3a/02

Reagents and conditions: (i) 20% COCl₂ in toluene, THF, 2 h; (ii) gemcitabine•HCl, KHCO₃, DMA, 100° C., 16 h Naphthalen-1-ylmethanol (1.0 g, 6.3 mmol) was added in one portion to COCl₂ (4.4 mL, as 20% solution of COCl₂ in toluene) in THF (20 mL). The reaction was stirred at room temperature for 2 h. Excess COCl₂ and THF was removed under reduced pressure. The solid residue was dissolved in hot hexane and filtered. The hexane solvent was then slowly evaporated off in vacuo to obtain the chloroformate intermediate 54 as a white solid. This was used straight away in the following step. Gemcitabine.HCl (200 mg, 0.67 mmol) was dissolved in H₂O (2 mL). To this was added KHCO₃ (67 mg, 0.67 mmol) and 54 (147 mg, 0.67 mmol), predissolved in ethyl acetate (5 mL). The mixture was stirred at 100° C. for 16 h. The solvent was evaporated off in vacuo and the product was purified by flash chromatography, eluting with 3% MeOH in ethyl acetate to obtain 56 (15 mg, 5%) as an oil. m/z=448.13 (M+H).

Benzyl 1-(3,3-difluoro-4-hydroxy-5-(hydroxymethyl)tetrahydrofuran-2-yl)-2-oxo-1,2-dihydropyrimidin-4-ylcarbamate (57) SU0044-2a/02

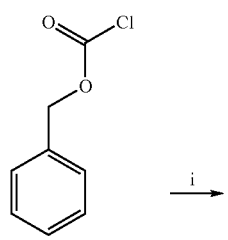

Reagents and conditions: (i) Cytarabine•HCl, KHCO₃, H₂O, EtOAc, 80° C., 16 h

Cytarabine.HCl (200 mg, 0.72 mmol) was dissolved in H₂O (2 mL). To this was added KHCO₃ (72 mg, 0.72 mmol) and benzyl carbonochloridate (107 μL, 0.72 mmol), predissolved in ethyl acetate (5 mL). The mixture was stirred at 80° C. for 16 h. The solvent was evaporated off in vacuo and the product was purified by flash chromatography, eluting with 3% MeOH in ethyl acetate to give 58 (40 mg, 15%) as an oil. m/z=378.13 (M+H).

Benzofuran-2-ylmethyl 4-nitrophenyl carbonate (60) and (5,7-dimethoxybenzofuran-2-yl)methyl 4-nitrophenyl carbonate (61)

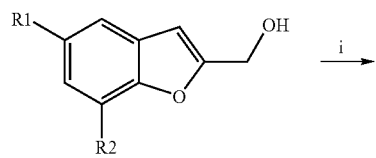

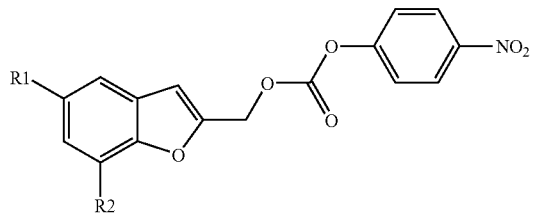

60: R1 and R2 = H
61: R1 and R2 = OMe

Reagents and conditions: (i) 4-nitrophenyl chloroformate, TEA, THF, rt, 2 h

Benzofuran-2-ylmethyl 4-nitrophenyl carbonate (60)

A solution of benzofuran-2-ylmethanol 59 (300 mg, 2.03 mmol) in THF (5 mL) was cooled to 0° C. TEA (280 µL, 2.03 mmol) was added dropwise followed by the portionwise addition of p-nitrophenyl chloroformate (282 mg, 3.05 mmol). The resulting solution was stirred at room temperature for 2 h. Solvent was evaporated off in vacuo and the crude residue was purified by flash chromatography, eluting with hexane:EtOAc (3:1) to give 60 (350 mg, 54%) as a white solid. $H^1$ NMR (500 MHz, CDCl$_3$): δ=8.31 (2H, m, ArH), 7.62 (1H, d, J=7.70 Hz, ArH), 7.54 (1H, d, J=7.70 Hz, ArH), 7.43-7.27 (3H, m, ArH), 7.29 (1H, t, J=7.72 Hz, ArH), 6.93 (1H, s, ArH), 5.43 (2H, s, CH$_2$). $^{13}$C NMR CDEPT 135, (500 MHz, CDCl$_3$): δ=125.47, 125.37, 123.23, 121.80, 121.66, 111.60, 108.53, 62.95.

(5,7-dimethoxybenzofuran-2-yl)methyl 4-nitrophenyl carbonate (61)

A solution of (5,7-dimethoxybenzofuran-2-yl)methanol 6 (100 mg, 0.48 mmol) in THF (3 mL) was cooled to 0° C. TEA (69 uL, 0.48 mmol) was added dropwise followed by the portionwise addition of p-nitrophenyl chloroformate (100 mg, 0.72 mmol). The resulting solution was stirred at room temperature for 2 h. Solvent was evaporated off in vacuo and the crude residue was purified by flash chromatography, eluting with hexane:EtOAc (3:1), to give 61 (120 mg, 67%) as a white solid. $H^1$ NMR (500 MHz, CDCl$_3$): δ=8.29 (2H, d, J=9.0 Hz, ArH), 7.40 (2H, d, J=9.0 Hz, ArH), 6.82 (1H, s, ArH), 6.63 (1H, s, ArH), 6.52 (1H, s, ArH), 5.39 (2H, s, CH$_2$), 4.00 (3H, s, OCH$_3$), 3.85 (3H, s, OCH$_3$).

Benzofuran-2-ylmethyl 1-(3,3-difluoro-4-hydroxy-5-(hydroxymethyl)tetrahydrofuran-2-yl)-2-oxo-1,2-dihydropyrimidin-4-ylcarbamate (65) SU050-03 and (5,7-dimethoxybenzofuran-2-yl)methyl 1-(3,3-difluoro-4-hydroxy-5-(hydroxymethyl)-tetrahydrofuran-2-yl)-2-oxo-1,2-dihydropyrimidin-4-ylcarbamate (66) SU048-04

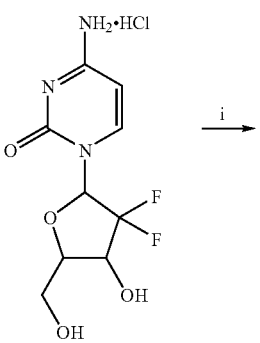

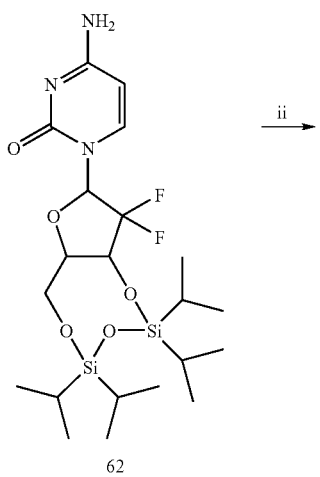

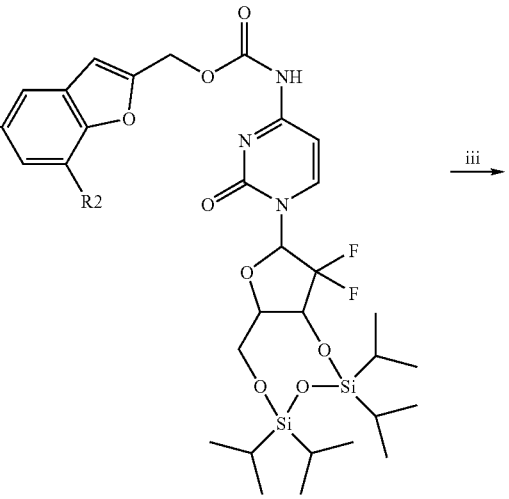

63: R1, R2 = H
64: R1, R2 = OMe

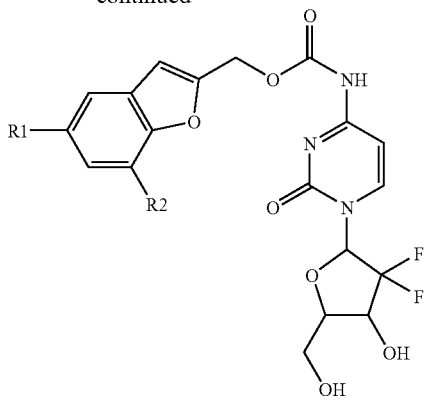

65: R1, R2 = H (SU050-03)
66: R1, R2 = OMe (SU048-04)

Reagents and conditions: (i) 1,1,3,3,-tetraisopropyldisiloxane, pyridine, 120° C., 1 h; (ii) 60 or 61, THF, 100° C., 4 days

4-amino-1-(9,9-difluoro-2,2,4,4-tetraisopropyltetrahydro-6H-furo[3,2-f][1,3,5,2,4]trioxadisilocin-8-yl)pyrimidin-2(1H)-one (62)

Gemcitabine.HCl (1.0 g, 3.3 mmol), was stirred in pyridine (10 mL) for 10 min (2×5 mL). The pyridine was evaporated off. The pyridine (10 mL) was added and 1,1,3,3,-tetraisopropyldisiloxane (1.17 mL, 3.63 mmol) was added dropwise. Resulting mixture was stirred at 100° C. for 16 h. A further portion of 1,1,3,3,-tetraisopropyldisiloxane (1 mL) was added and the mixture was stirred at 120° C. for 1 h. Reaction mixture was cooled to room temperature and solvent was evaporated off in vacuo. The resulting crude solid was recrystalised from EtOAc/ether (1:1) to give 62 (600 mg, 36%) as a white solid. m/z=506.23 (M+H).

Benzofuran-2-ylmethyl 1-(9,9-difluoro-2,2,4,4-tetraisopropyltetrahydro-6H-furo[3,2-f][1,3,5,2,4]trioxadisilocin-8-yl)-2-oxo-1,2-dihydropyrimidin-4-ylcarbamate (63)

To a stirred solution of 62 (300 mg, 0.59 mmol) in THF (5 mL) was added benzofuran-2-ylmethyl 4-nitrophenyl carbonate (223 mg, 0.71 mmol). The resulting solution was stirred at 100° C. for 4 days. Solvent was evaporated off in vacuo and the product was purified by preparative HPLC to give 63 (350 mg, 87%) as an oil. m/z=680.0 (M+H), 1359.49 (2M+H).

Benzofuran-2-ylmethyl 1-(3,3-difluoro-4-hydroxy-5-(hydroxymethyl)tetrahydrofuran-2-yl)-2-oxo-1,2-dihydropyrimidin-4-ylcarbamate (65) SU050-03

Compound 63 (200 mg, 0.29 mmol) was dissolved in THF (1.5 mL). To this was added tetra-n-butylammonium fluoride and the resulting solution was stirred at room temperature for 15 min. Solvent was evaporated off in vacuo. The product was purified by flash chromatography, eluting with 5% MeOH in EtOAc to give 65 (30 mg, 23%) as an oil. m/z=438.14 (M+H), 874.24 (2M+H).

(5,7-dimethoxybenzofuran-2-yl)methyl 1-(3,3-difluoro-4-hydroxy-5-(hydroxymethyl)-tetrahydrofuran-2-yl)-2-oxo-1,2-dihydropyrimidin-4-ylcarbamate (66) SU048-04

To a stirred solution of 62 (108 mg, 0.21 mmol) in THF (5 mL) was added 61 (100 mg, 0.27 mmol). The resulting solution was stirred at 100° C. for 4 days. Solvent was evaporated off in vacuo to give 64 as an oil. This was used in the next step without further purification. Compound 64 (100 mg, 0.14 mmol) was dissolved in THF (1.5 mL). To this was added tetra-n-butylammonium fluoride and the resulting solution was stirred at room temperature for 15 min. Solvent was evaporated off in-vacuo. The product was purified by flash chromatography, eluting with 5% MeOH in EtOAc to give 66 (18 mg, 26%) as an oil. m/z=498.14 (M+H), 995.29 (2M+H). H$^1$ NMR (500 MHz, acetone-d$_6$): δ=9.60 (1H, bs, NH), 8.34 (1H, d, J=7.62 Hz, ArH), 7.26 (1H, d, J=9.00 Hz, ArH), 6.92 (1H, s, ArH), 6.71 (1H, d, J=2.20 Hz, ArH), 6.56 (1H, d, J=2.20 Hz, ArH), 6.26 (1H, t, J=7.56 Hz, CH), 5.64 (2H, s, CH$_2$), 4.55-4.45 (1H, m, CH), 4.05-4.02 (2H, m, CH$_2$), 3.97 (3H, s, OCH$_3$), 3.91-3.3.87 (1H, m, CH), 3.82 (3H, s, OCH$_3$), 2.92 (2H, bs, OH).

4. Carbamate-Linked Nitrogen and Aniline Mustard Prodrugs

VG042-04

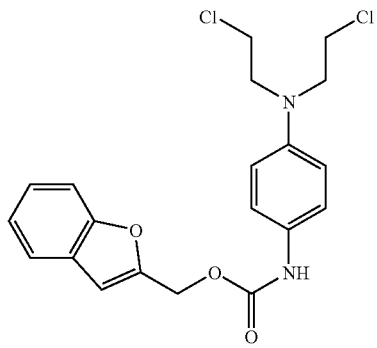

VG0445-04

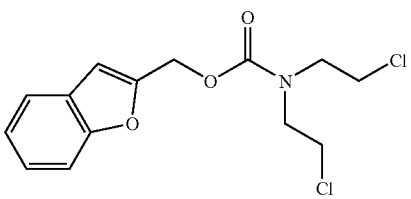

Benzofuran-2-ylmethyl 4-(bis(2-chloroethyl)amino) phenylcarbamate (VG042-04)

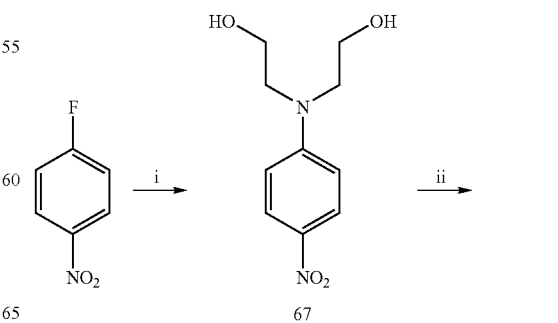

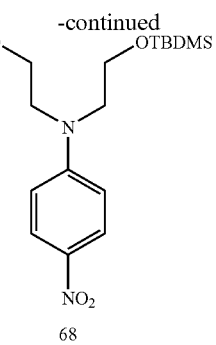

68

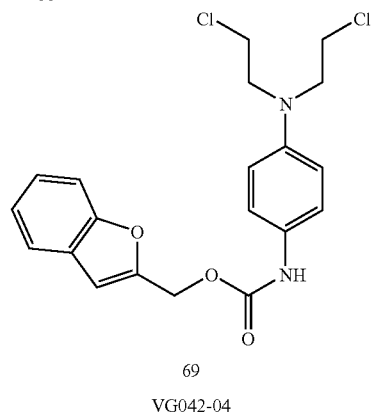

69
VG042-04

Reagents and conditions:

(i) diethanolamine, DMF, 140° C., 3 h;
(ii) tert-butyl dimethyl silyl chloride, imidazole, DMF, rt, 48 h;
(iii) a. 10% Pd/C, EtOH, rt, 16 h;
    b. triphosgene, TEA, THF, rt, 1 h;
    c. 59, THF, rt, 16 h,
    d. TBAF, 15 min, rt.
    e. pyridine, methane sulphonyl chloride

2,2'-(4-nitrophenylazanediyl)diethanol (67)

Diethanolamine (2.70 mL, 2.5 mmol) was added to 1-fluoro-4-nitrobenzene (1.0 g, 7.09 mmol) in DMF (30 mL). The resulting mixture was stirred at 140° C. for 3.5 h. The solution was cooled to room temperature and solvent was evaporated off in vacuo. The residue was dissolved in EtOAc (30 mL) and washed with water (3×10 mL) and brine (3×20 mL) and dried (MgSO$_4$). Solvent was evaporated off in vacuo and the product was purified by flash chromatography, eluting with EtOAc to give 67 (400 mg, 25%) as a yellow solid. H$^1$ NMR (500 MHz, CDCl$_3$): δ=8.06 (2H, d, J=9.50 Hz, ArH), 6.87 (2H, d, J=9.50 Hz, ArH), 4.27 (2H, t, J=5.35 Hz, 2×OH), 3.83 (4H, q, J=5.55 & 5.45 Hz, 2×CH$_2$), 3.74 (4H, t, J=5.62 Hz, 2×CH$_2$).

N,N-bis(2-(tert-butyldimethylsilyloxy)ethyl)-4-nitroaniline (68)

To a cooled solution of 67 (400 mg, 1.77 mmol) and imidazole (481 mg, 7.08 mmol) in DMF (10 mL) was added dropwise tert-butyl dimethyl silyl chloride (2.72 mg, 3.54 mmol). The mixture was allowed to reach room temperature and stirred for 48 h. The solvent was evaporated off in vacuo and the product was purified by flash chromatography, eluting with 10% EtOAc in ether to give 68 (200 mg, 25%) as a yellow solid. H$^1$ NMR (500 MHz, CDCl$_3$): δ=8.06 (2H, d, J=9.45 Hz, ArH), 6.65 (2H, d, J=9.45 Hz, ArH), 3.80 (4H, t, J=5.80 Hz, 2×CH$_2$), 3.62 (4H, t, J=5.80 Hz, 2×CH$_2$), 0.85 (18H, s, 6×CH$_3$), −0.01 (12H, s, 4×CH$_3$).

Benzofuran-2-ylmethyl 4-(bis(2-chloroethyl)amino) phenylcarbamate (69) VG042-04

Compound 68 (200 mg, 0.44 mmol) was treated with hydrogen in the presence of 10% Pd on carbon (20 mg). After 16 h stirring, the mixture was filtered through Celite and the solvent was evaporated off in vacuo to give the intermediate amino aniline product. This was then reacted with triphosgene (195 mg, 0.70 mmol) in the presence of triethylamine (260 uL, 0.70 mmol) in THF (15 mL). After 1 h stirring at room temperature a white precipitate was filtered off and the solvent was evaporated off in vacuo to give a crude residue of isocyanate aniline. This was used straight away in the following step. Isocyanate intermediate was dissolved in THF (10 mL). The solution was cooled to 0° C. Benzofuran-2-ylmethanol 59 (100 mg, 1.35 mmol) was added and the resulting mixture was stirred at room temperature for 16 h. The mixture was cooled on ice and TBAF (996 μL, 3.38 mmol) was added dropwise over 5 min. The resulting mixture was allowed to warm to room temperature and then stirred for 20 min. THF was evaporated off in vacuo. The intermediate was dissolved in pyridine (5 mL) and to this was added methane sulphonyl chloride (12.5 μL, 0.16 mmol). The mixture was stirred at room temperature for 1 h. Pyridine was evaporated off in vacuo and the crude product was purified by flash chromatography, eluting with hexane:EtOAc (3:1) to give 69 (5 mg, 2%) as a white solid. m/z=408.07 (M+H), 837.16 (2M+H).

Benzofuran-2-ylmethyl bis(2-chloroethyl)carbamate (70) VG045-04

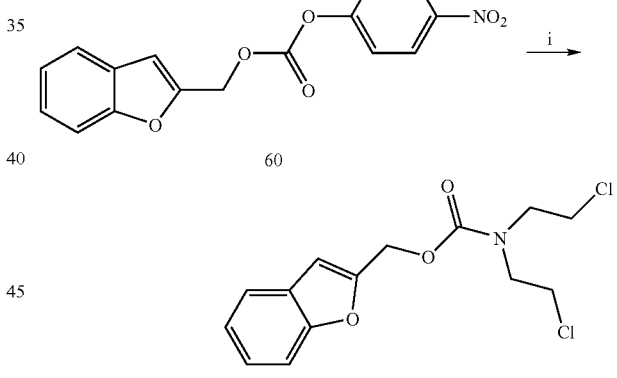

70
VG045-04

Reagents and conditions:

(i) bis-(2-chloroethylamine)•HCl, pyridine, rt, 16 h.

A solution of 60 (200 mg, 0.64 mmol) in pyridine (3 mL) was added to a solution of bis(2-chloroethylamine).hydrochloride (227 mg, 1.28 mmol) in pyridine (25 mL). The mixture was stirred at room temperature for 16 h. DCM (10 mL) was added and the mixture was washed with 2% citric acid solution (2×50 mL), water (50 mL), brine (50 mL) and dried (MgSO$_4$). Solvent was evaporated off in vacuo and the product was purified by flash chromatography, eluting with CH$_2$Cl$_2$:hexane (2:1) to give 70 (125 mg, 62%) as an oil. m/z=338.05 (M+Na). H$^1$ NMR (500 MHz, CDCl$_3$): δ=7.60 (1H, d, J=7.70 Hz, ArH), 7.51 (1H, d, J=8.05 Hz, ArH), 7.33 (1H, t, J=6.80 Hz, ArH), 7.26 (1H, t, J=6.80 Hz, ArH), 6.79 (1H, s, ArH), 5.28 (2H, s, CH$_2$), 3.72-3.63 (8H, m, 4×CH$_2$).

5. Ether-Linked Topoisomerase I Inhibitor Prodrug

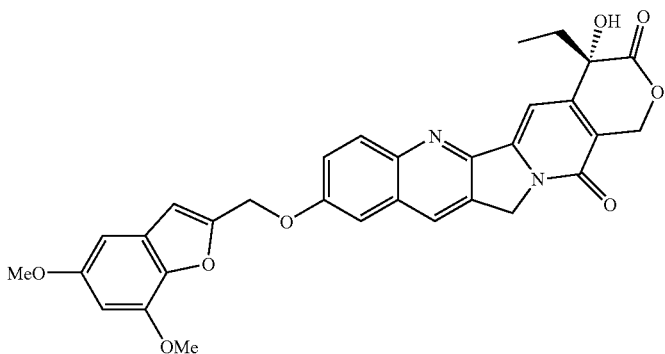

SU037-04

(5,7-Dimethoxybenzofuran-2-yl)methyl-camptothecin (71) SU037-04

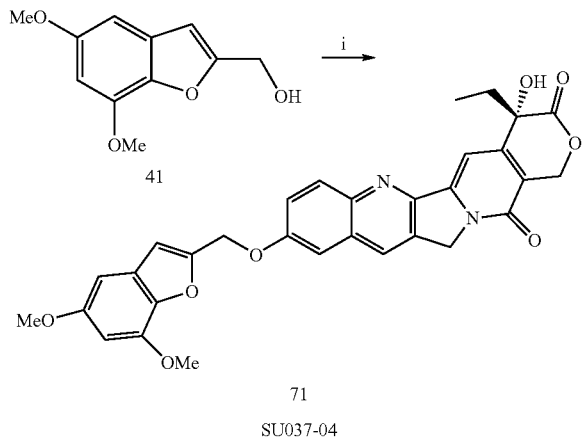

Reagents and conditions:
(i) a. PBr₃, toluene, rt, 1 h;
  b. (i) Sodium ethoxide, DMF, 2 h,
    (ii) Camptothecin, DMF, rt, 2 h.

Compound 41 (100 mg, 0.48 mmol) was dissolved in toluene (5 mL) and the solution was cooled to 0° C. PBr$_3$ (46 μL, 0.48 mmol) was added dropwise over 10 min. The reaction mixture was then brought up to room temperature and stirred for 1 h. The solvent was evaporated off in-vacuo. The crude residue was used in the next step.

Sodium ethoxide (15 mg, 0.22 mmol) was added to DMF (5 mL) at 0° C., and the suspension was stirred for 10 min. Camptothecin (81 mg, 0.22 mmol) was slowly added and resulting mixture was stirred at this temp for 0.5 h. To this mixture, crude residue from previous step, 2-(bromomethyl)-5,7-dimethoxybenzofuran (50 mg, 0.18 mmol) was added portionwise. Resulting mixture was stirred at room temperature for 2 h. DMF was evaporated off in-vacuo and the residue was purified by flash chromatography, eluting with DCM:EtOAc (2:1) to give the target compound as a white solid (10 mg, 10%). m/z=555.19 (M+H).

6. Ether-Linked Tyrosine Kinase Inhibitor Prodrugs

VG048-04

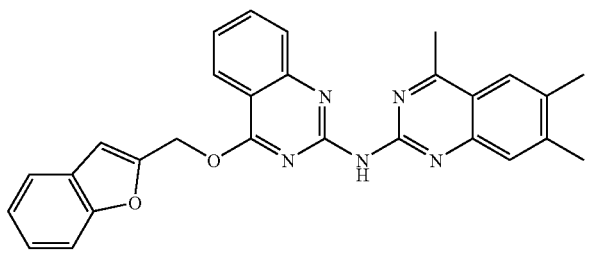

SU01-A-04

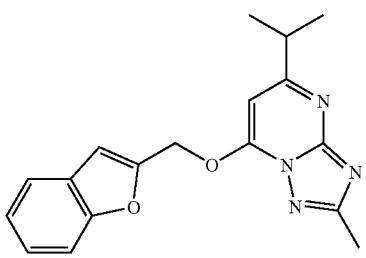

SU01-B-04

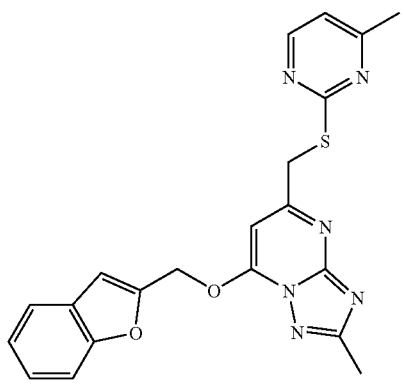

SU01-C-04

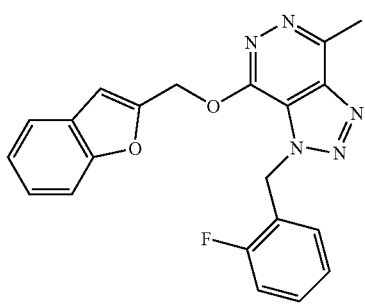

N-(4-(benzofuran-2-ylmethoxy)quinazolin-2-yl)-4,6,7-trimethylquinazolin-2-amine (72) VG048-04

7-(benzofuran-2-ylmethoxy)-5-isopropyl-2-methyl-[1,2,4]triazolo[1,5-a]pyrimidine (73) SU01-A-04

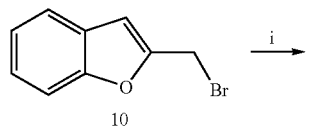

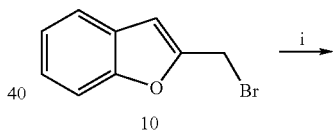

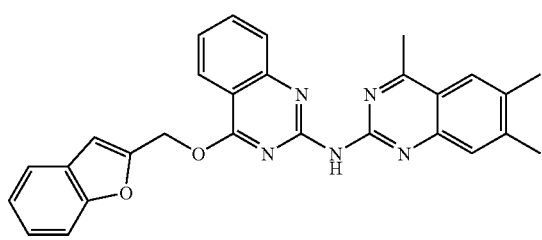

72
VG048-04

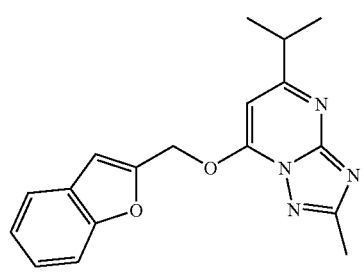

73
SU01-A-04

Reagents and conditions: (i) Sodium ethoxide, 2-(4,6-dimethylquinazolin-2-ylamino)quinazolin-4-ol, DMF, rt, 0.5 h.

Reagents and conditions:

(i) Sodium ethoxide, 5-isopropyl-2-methyl-[1,2,4]triazolo[1,5-a]-7-ol, DMF, rt, 1 h.

Sodium ethoxide (3 mg, 0.05 mmol) was added to DMF (2 mL) at 0° C., and the suspension was stirred for 5 min. 2-(4,6-dimethylquinazolin-2-ylamino)quinazolin-4-ol (15 mg, 0.05 mmol) was slowly added and resulting mixture was stirred at this temperature for 0.5 h. To this mixture 2-(bromomethyl)benzofuran (16 mg, 0.08 mmol) was added. Resulting mixture was stirred at room temperature for 1 h. DMF was evaporated off in-vacuo to give a crude white solid. This was purified by washing with cold ether and EtOAc to give 72 (3 mg, 11%) as a white solid. m/z=462.2 (M+H).

Sodium ethoxide (7.2 mg, 0.10 mmol) was added to DMF (2 mL) at 0° C., and the suspension was stirred for 5 min. 5-isopropyl-2-methyl-[1,2,4]triazolo[1,5-a]pyrimidin-7-ol (20 mg, 0.10 mmol) was slowly added and resulting mixture was stirred at this temperature for 0.5 h. To this mixture 2-(bromomethyl)benzofuran (16 mg, 0.08 mmol) was added. Resulting mixture was stirred at room temperature for 1 h. DMF was evaporated off in-vacuo to give a crude white solid.

This was purified by semi-preparative HPLC to give 73 (6.3 mg, 19%) as a white solid. m/z=323.13 (M+H), 645.27 (2M+H).

7-(benzofuran-2-ylmethoxy)-2-methyl-5-((4-methylpyrimidin-2-ylthio)methyl)-[1,2,4]triazolo[1,5-a]pyrimidine (74) SU01-B-04

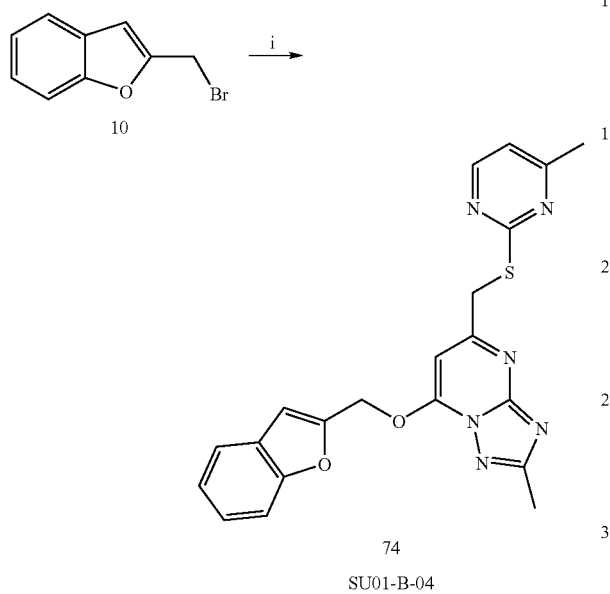

74
SU01-B-04

Reagents and conditions:

(i) Sodium ethoxide, 2-methyl-5-((4-methylpyrimidin-2-ylthio)methyl)-[1,2,4]triazolo[1,5-a]pyrimidin-7-ol, DMF, rt, 1 h.

Sodium ethoxide (4.7 mg, 0.07 mmol) was added to DMF (2 mL) at 0° C., and the suspension was stirred for 5 min. 2-methyl-5-((4-methylpyrimidin-2-ylthio)methyl)-[1,2,4]triazolo[1,5-a]pyrimidin-7-ol (20 mg, 0.07 mmol) was slowly added and resulting mixture was stirred at this temp for 0.5 h. To this mixture 10 (16 mg, 0.08 mmol) was added. Resulting mixture was stirred at room temperature for 1 h. DMF was evaporated off in-vacuo to give a crude white solid. This was purified by semi-preparative HPLC to give 74 (5.2 mg, 18%) as a white solid. m/z=419.09 (M+H), 837.23 (2M+H).

7-(benzofuran-2-ylmethoxy)-1-(2-fluorobenzyl)-4-methyl-1H-[1,2,3]triazolo[4,5-d]pyridazine (75) SU01-C-04

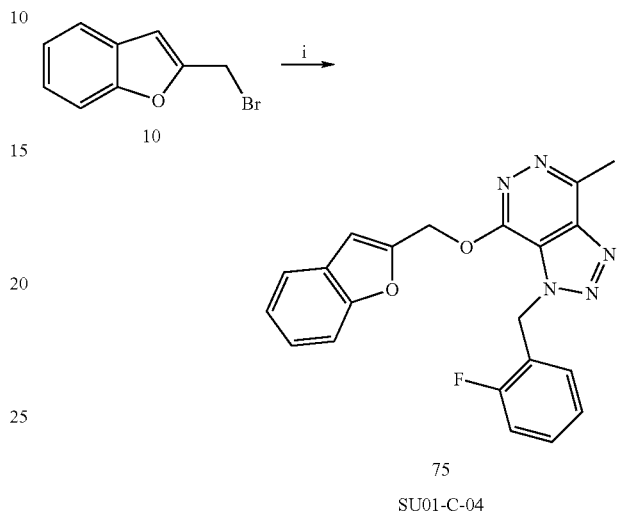

75
SU01-C-04

Reagents and conditions:

(i) Sodium ethoxide, 2-methyl-5-((4-methylpyrimidin-2-ylthio)methyl)-[1,2,4]triazolo[1,5-a]pyrimidin-7-ol, DMF, rt, 1 h.

Sodium ethoxide (5.2 mg, 0.08 mmol) was added to DMF (2 mL) at 0° C., and the suspension was stirred for 5 min. 1-(2-fluorobenzyl)-4-methyl-1H-[1,2,3]triazolo[4,5-d]pyridazin-7-ol (20 mg, 0.08 mmol) was slowly added and resulting mixture was stirred at this temp for 0.5 h. To this mixture 2-(bromomethyl)benzofuran (16 mg, 0.08 mmol) was added. Resulting mixture was stirred at room temperature for 1 h. DMF was evaporated off in-vacuo to give a crude white solid. This was purified by semi-preparative HPLC to give 75 (3 mg, 10%) as a white solid. m/z=390.07 (M+H), 801.12 (2M+Na).

7. Carbamate-Linked Model Coumarin Prodrugs

TLE-M1-SU001C (†)

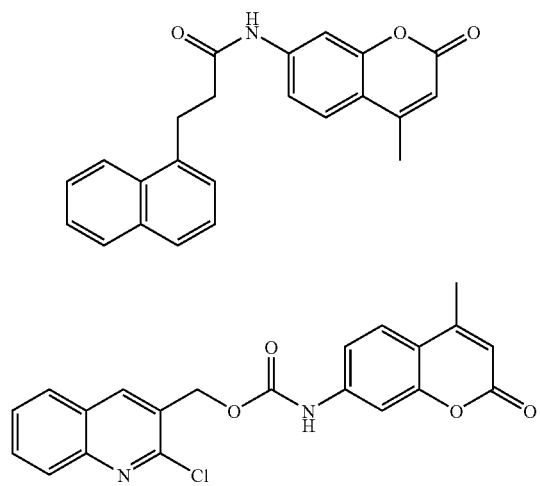

SU030-7-03

-continued
SU002102
(†)
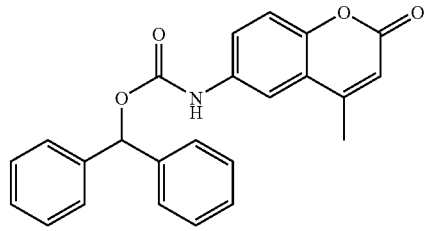
SU030-8-03
(†)
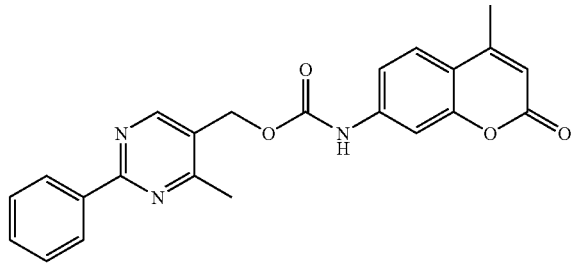
VG032-03
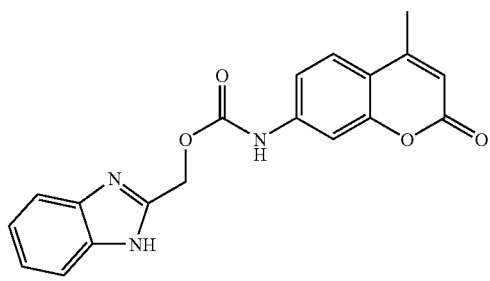
SU033-03
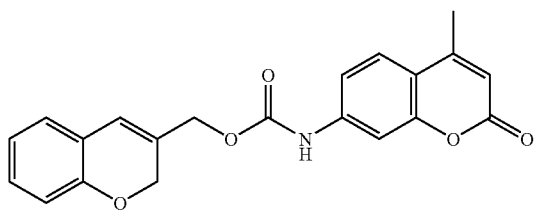
VG037-03
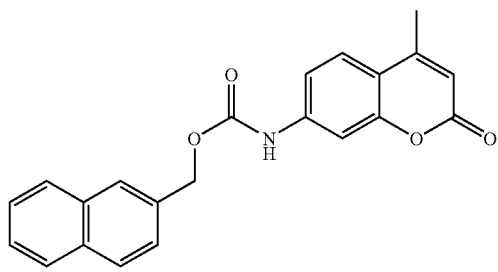
SU018-03
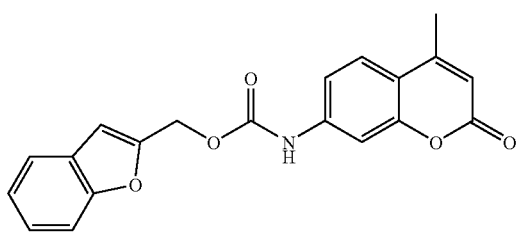

-continued
SU024-2-03
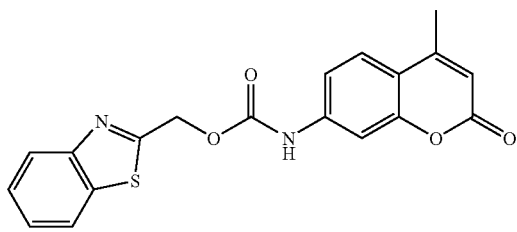
VG032-05
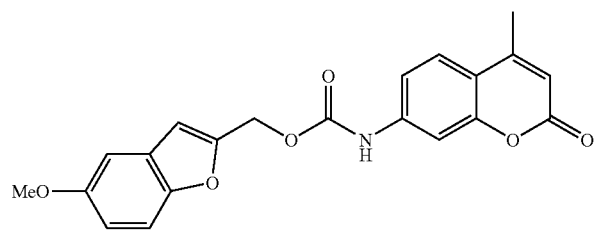
SU024-3-03
(†)
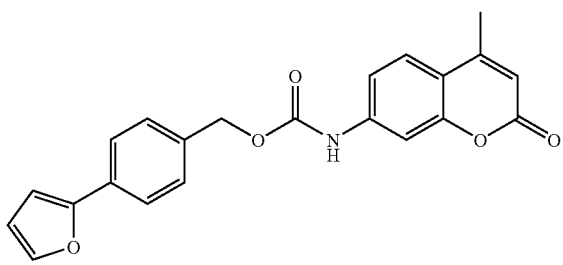
VG036-05
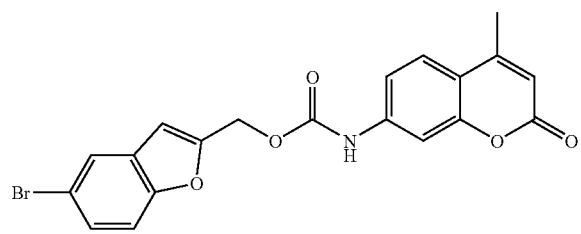
SU030-4-03
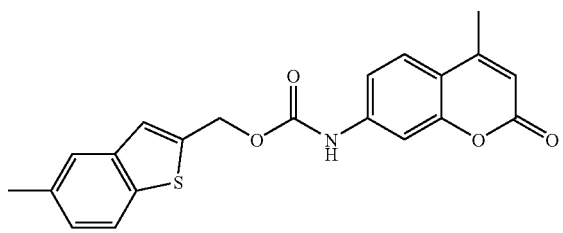
VG041-05
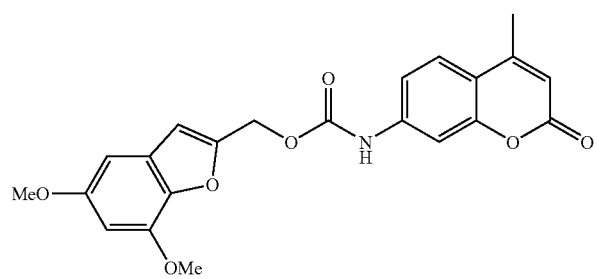

7-Isocyanato-4-methylcoumarin (76)

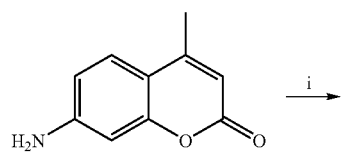

Reagents and conditions:

(i) 20% phosgene in toluene, dioxane, 100° C., 17 h.

A 200-mL three-neck flask fitted with a dry ice condenser and magnetic stirrer was charged with a solution of 20% phosgene in toluene solution (2.0 mL) and dioxane (80 mL). To this mixture was added 7-amino-4-methyl-2H-chromen-2-one (2.00 g, 11.4 mmol). The mixture was stirred at 100° C. for 12 h. The initial yellow colour disappeared and a white solid precipitated. An additional 20% phosgene in toluene solution (7.0 mL) was added and the mixture heated for an additional 5 h, at which time the solution cleared. Excess phosgene and traces of HCl was removed by bubbling nitrogen gas through the solution. The cloudy solution was filtered to remove unreacted 7-amino-4-methyl-2H-chromen-2-one and concentrated to give 76 (0.5 g, 25%) as a white solid. $H^1$ NMR (500 MHz, CDCl$_3$): δ=7.50 (1H, d, J=7.40 Hz, ArH), 7.46 (2H, s, ArH), 6.20 (1H, s, ArH), 2.35 (3H, s, CH$_3$): ir (CH$_2$CL$_2$) 2314 (N=C=O), 1726 and 1615 cm$^{-1}$.

Naphthalen-1-ylmethyl 4-methyl-2-oxo-2H-chromen-7-ylcarbamate (77) VG020-02

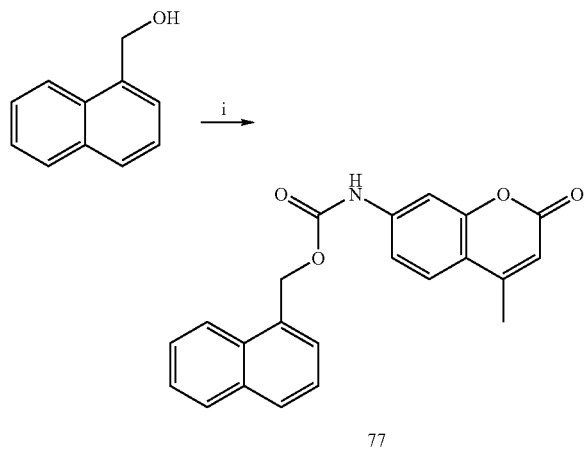

Reagents and conditions:

(i) 76, THF, 80° C., 1 h.

Naphthalen-1-ylmethanol (56 mg, 0.28 mmol) and 76 (200 mg, 1.27 mmol) were dissolved in THF (2 mL). The resulting mixture was stirred at room temperature for 15 min and then at 80° C. for 1 h. THF was evaporated off in vacuo. The residue was adsorbed on silica and purified by flash chromatography, eluting with CH$_2$Cl$_2$/hexane/EtOAc (1:1:1) to give 77 (3 mg, 5%) as a white solid. m/z=360.14 (M+H), 719.27 (2M+H).

(2-chloroquinolin-3-yl)methyl 4-methyl-2-oxo-2H-chromen-7-ylcarbamate (78) SU030-7-03

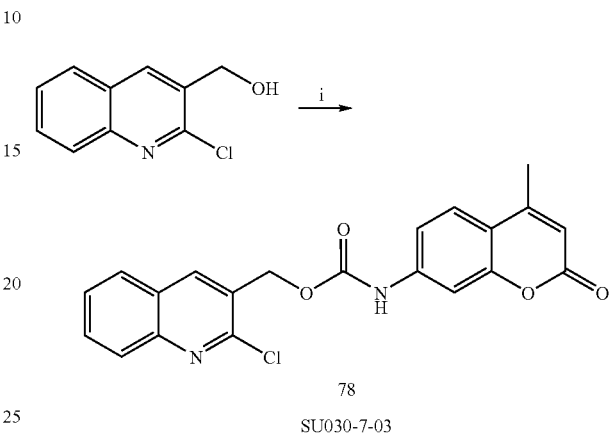

Reagents and conditions:

(i) 76, THF, 80° C., 1 h.

(2-chloroquinolin-3-yl)methanol (100 mg, 0.52 mmol) and 76 (155 mg, 0.77 mmol) were dissolved in THF (2 mL). The resulting mixture was stirred at room temperature for 15 min and then at 80° C. for 1 h. THF was evaporated off in-vacuo. The residue was adsorbed on silica and purified by flash chromatography, eluting with CH$_2$Cl$_2$/EtOAc (1:1) to give 78 (38 mg, 19%) as a white solid. m/z=395.08 (M+H).

Benzhydryl 4-methyl-2-oxo-2H-chromen-7-ylcarbamate (79) SU0021-02

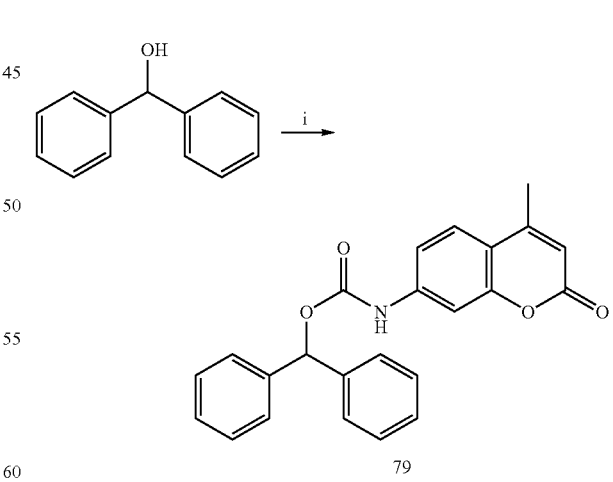

Reagents and conditions:

(i) 76, THF, 80° C., 1 h.

(2-Chloroquinolin-3-yl)methanol (119 mg, 0.65 mmol) and 76 (70 mg, 0.35 mmol) were dissolved in THF (2 mL).

The resulting mixture was stirred at room temperature for 15 min and then at 80° C. for 1 h. THF was evaporated off in vacuo. The residue was adsorbed on silica and purified by flash chromatography, eluting with CH$_2$Cl$_2$/EtOAc (1:1) to give 79 (50 mg, 37%) as a white solid. m/z=386.16 (M+H).

Benzhydryl 4-methyl-2-oxo-2H-chromen-7-ylcarbamate (80) SU0021-02

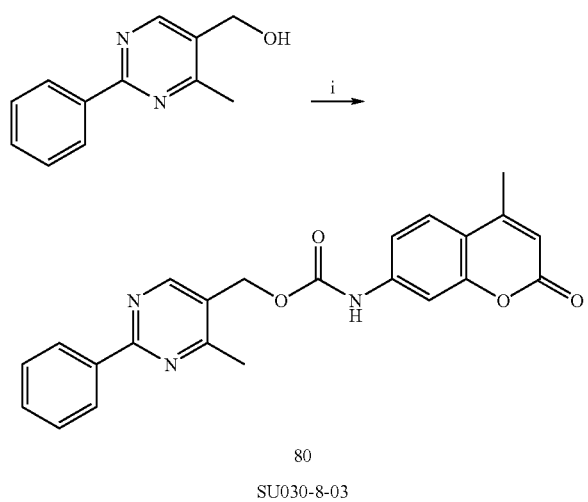

80
SU030-8-03

Reagents and conditions:

(i) 76, THF, 80° C., 1 h.

(4-Methyl-2-phenylpyrimidin-5-yl)methanol (100 mg, 0.50 mmol) and 76 (151 mg, 0.75 mmol) were dissolved in THF (2 mL). The resulting mixture was stirred at room temperature for 15 min and then at 80° C. for 1 h. THF was evaporated off in vacuo. The residue was adsorbed on silica and purified by flash chromatography, eluting with CH$_2$Cl$_2$/EtOAc (1:1) to give 80 (70 mg, 35%) as a white solid. m/z=402.15 (M+H).

(1H-benzo[d]imidazol-2-yl)methyl 4-methyl-2-oxo-2H-chromen-7-ylcarbamate (81) VG032-03

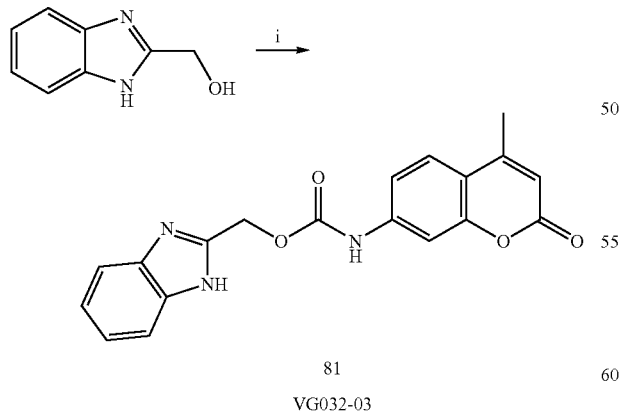

81
VG032-03

Reagents and conditions:

(i) 76, THF, 80° C., 1 h.

(1H-benzo[d]imidazol-2-yl)methanol (200 mg, 1.35 mmol) and 76 (272 mg, 1.35 mmol) were dissolved in THF (2 mL). The resulting mixture was stirred at room temperature for 15 min and then at 80° C. for 1 h. THF was evaporated off in vacuo. The residue was adsorbed on silica and purified by flash chromatography, eluting with CH$_2$Cl$_2$/EtOAc (1:1) to give 81 (80 mg, 17%) as a white solid. m/z=350.12 (M+H).

(2H-chromen-3-yl)methyl 4-methyl-2-oxo-2H-chromen-7-ylcarbamate (82) SU033-03

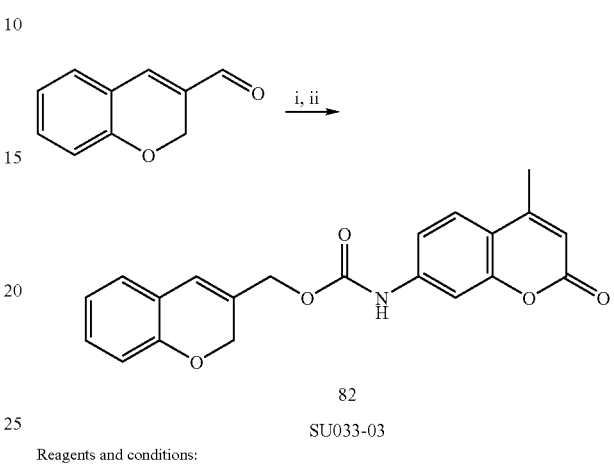

82
SU033-03

Reagents and conditions:

(i) NaBH$_4$, EtOH, rt, 1.5 h;
(ii) THF, 80° C., 1 h.

2H-chromene-3-carbaldehyde (500 mg, 3.13 mmol) was dissolved in EtOH (10 mL). NaBH$_4$ (119 mg, 3.13 mmol) was added portionwise at 0° C., with vigorous stirring. The suspension was stirred at 0° C. for 15 min and then at room temperature for 1.5 h. Solvent was evaporated off in-vacuo to obtain the alcohol intermediate as an oil. This was dissolved in THF (5 mL) and 76 (155 mg, 0.77 mmol) was added. The resulting mixture was stirred at room temperature for 15 min and then at 80° C. for 1 h. THF was evaporated off in vacuo. The residue was adsorbed on silica and purified by flash chromatography, eluting with CH$_2$Cl$_2$/EtOAc (1:1) to give 82 (80 mg, 8%) as a white solid. m/z=364.12 (M+H), 727.23 (2M+H).

Naphthalen-2-ylmethyl 4-methyl-2-oxo-2H-chromen-7-ylcarbamate (83) VG037-03

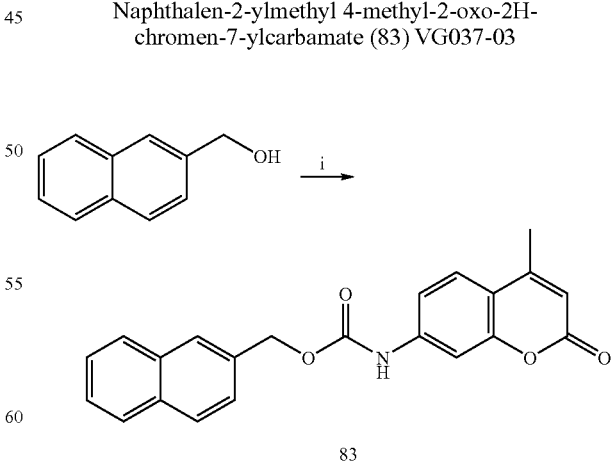

83
VG037-03

Reagents and conditions:

(i) 76, THF, 80° C., 1 h.

Naphthalen-2-ylmethanol (200 mg, 1.27 mmol) and 76 (279 mg, 1.39 mmol) were dissolved in THF (2 mL). The resulting mixture was stirred at room temperature for 15 min and then at 80° C. for 1 h. THF was evaporated off in vacuo. The residue was adsorbed on silica and purified by flash chromatography, eluting with $CH_2Cl_2$/EtOAc (1:1) to give 83 (26 mg, 6%) as a white solid. m/z=360.13 (M+H), 719.25 (2M+H).

Benzofuran-2-ylmethyl 4-methyl-2-oxo-2H-chromen-7-ylcarbamate (84) SU018-03

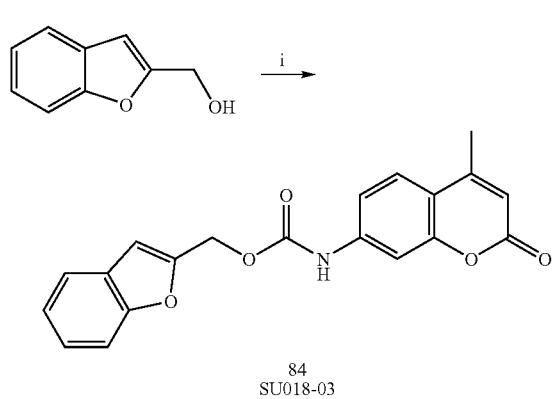

84
SU018-03
Reagents and conditions: (i) 76, THF, 80° C., 1 h.

Benzofuran-2-ylmethanol (300 mg, 2.03 mmol) and 76 (407 mg, 2.03 mmol) were dissolved in THF (2 mL). The resulting mixture was stirred at room temperature for 15 min and then at 80° C. for 1 h. THF was evaporated off in vacuo. The residue was adsorbed on silica and purified by flash chromatography, eluting with $CH_2Cl_2$/EtOAc (1:1) to give 84 (130 mg, 18%) as a white solid. m/z=350.09 (M+H), 699.17 (2M+H).

Benzo[d]thiazol-2-ylmethyl 4-methyl-2-oxo-2H-chromen-7-ylcarbamate (85) SU024-3-03

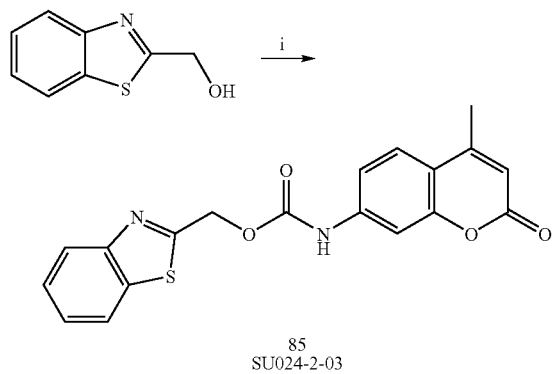

85
SU024-2-03
Reagents and conditions: (i) 76, THF, 80° C., 1 h.

Benzo[d]thiazol-2-ylmethanol (200 mg, 1.21 mmol) and 76 (365 mg, 1.8 mmol) were dissolved in THF (2 mL). The resulting mixture was stirred at room temperature for 15 min and then at 80° C. for 1 h. THF was evaporated off in vacuo. The residue was adsorbed on silica and purified by flash chromatography, eluting with $CH_2Cl_2$/EtOAc (1:1) to give 85 (90 mg, 20%) as a white solid. m/z=367.02 (M+H), 733.13 (2M+H).

4-(furan-2-yl)benzyl 4-methyl-2-oxo-2H-chromen-7-ylcarbamate (86) SU024-3-03

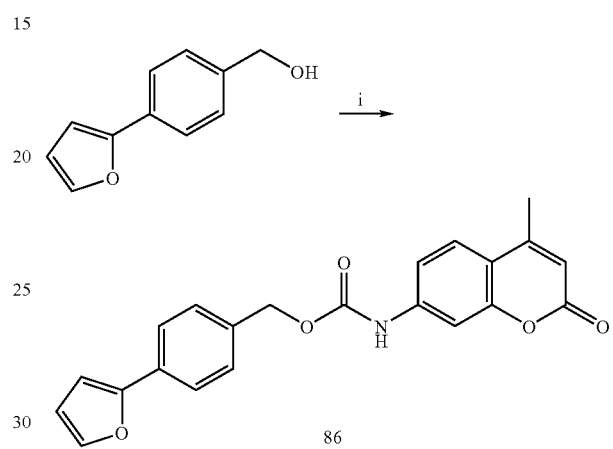

86
SU024-3-03
Reagents and conditions: (i) 76, THF, 80° C., 1 h.

(4-(Furan-2-yl)phenyl)methanol (100 mg, 0.57 mmol) and 76 (139 mg, 0.69 mmol) were dissolved in THF (10 mL). The resulting mixture was stirred at room temperature for 15 min and then at 80° C. for 1 h. THF was evaporated off in vacuo. The residue was adsorbed on silica and purified by flash chromatography, eluting with $CH_2Cl_2$/EtOAc (1:1) to give the target compound (20 mg, 9%) as a white solid. m/z=376.11 (M+H), 751.22 (2M+H).

(5-methylbenzo[b]thiophen-2-yl)methyl 4-methyl-2-oxo-2H-chromen-7-ylcarbamate (87) SU030-4-03

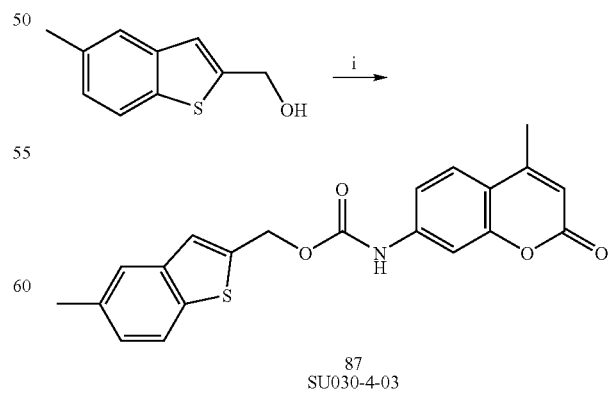

87
SU030-4-03
Reagents and conditions: (i) 76, THF, 50° C., 3 h.

(5-Methylbenzo[b]thiophen-2-yl)methanol (100 mg, 0.56 mmol) and 76 (136 mg, 0.67 mmol) were dissolved in THF (2 mL). The resulting mixture was stirred at room temperature for 15 min and then at 50° C. for 3 h. THF was evaporated off in vacuo. The residue was adsorbed on silica and purified by flash chromatography, eluting with CH$_2$Cl$_2$/EtOAc (1:1) to give 87 (38 mg, 18%) as a white solid. m/z=380.09 (M+H), 759.17 (2M+H).

(5-methoxybenzofuran-2-yl)methyl 4-methyl-2-oxo-2H-chromen-7-ylcarbamate (88) VG032-05

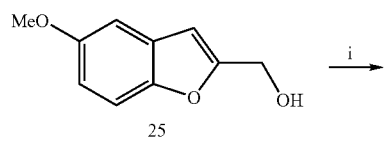

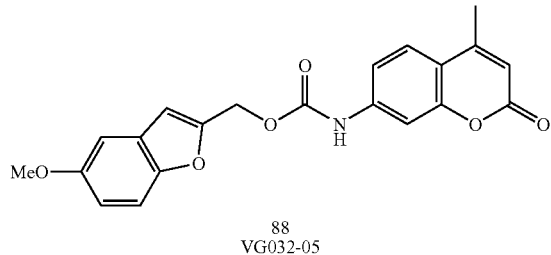

88
VG032-05

Reagents and conditions: (i) 76, THF, rt, 16 h.

(5-Methoxybenzofuran-2-yl)methanol 25 (200 mg, 1.12 mmol) and 76 (190 mg, 0.95 mmol) were dissolved in THF (10 mL). The resulting mixture was stirred at room temperature for 15 min and then at room temperature for 16 h. THF was evaporated off in vacuo. The residue was adsorbed on silica and purified by flash chromatography, eluting with hexane/EtOAc (1:1) to give 88 (20 mg, 5%) as a white solid. m/z=380.13 (M+H), 759.26 (2M+H).

(5-bromobenzofuran-2-yl)methyl 4-methyl-2-oxo-2H-chromen-7-ylcarbamate (89) VG036-05

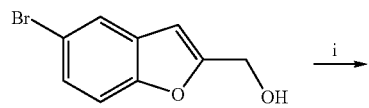

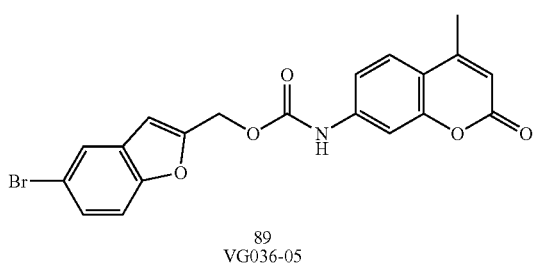

89
VG036-05

Reagents and conditions: (i) 76, THF, 80° C., 1 h.

(5-Bromobenzofuran-2-yl)methanol (100 mg, 0.44 mmol) and 76 (106 mg, 0.52 mmol) were dissolved in THF (2 mL). The resulting mixture was stirred at room temperature for 15 min and then at 80° C. for 1 h. THF was evaporated off in vacuo. The residue was adsorbed on silica and purified by flash chromatography, eluting with CH$_2$Cl$_2$/EtOAc (1:1) to give 89 (5.0 mg, 3%) as a white solid. m/z=429.10 (M+H).

(5,7-dimethoxybenzofuran-2-yl)methyl 4-methyl-2-oxo-2H-chromen-7-ylcarbamate (90) VG041-05

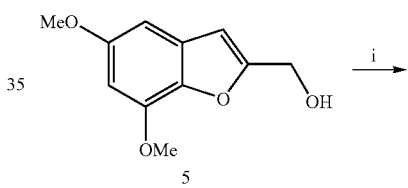

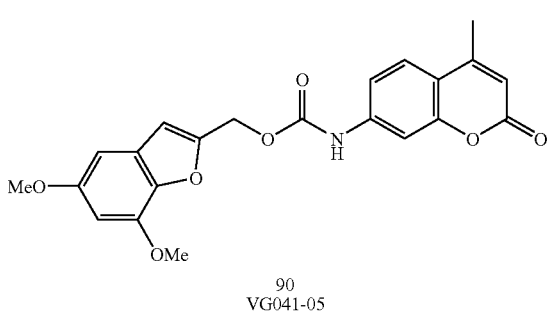

90
VG041-05

Reagents and conditions: (i) 76, THF, rt, 16 h.

(5,7-dimethoxybenzofuran-2-yl)methanol 5 (50 mg, 0.24 mmol) and 7-isocyanato-4-methylcoumarin (58 mg, 0.29 mmol) were dissolved in THF (10 mL). The resulting mixture was stirred at room temperature for 16 h. THF was evaporated off in vacuo. The residue was adsorbed on silica and purified by flash chromatography, eluting with CH$_2$Cl$_2$/EtOAc (1:1) to give 90 (5.0 mg, 3%) as a white solid. m/z=410.04 (M+H).

8. Extended Linkers: Oxybenzyl Ether, Carbamate Benzyl Ether, Oxybenzyl Carbamate
TLE-M1-SU001B
(†)
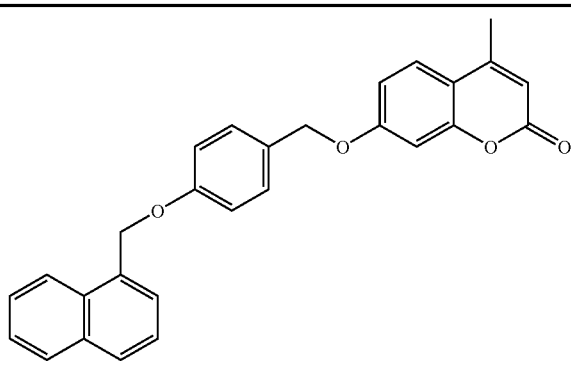
TLE-M1-SU004
(†)
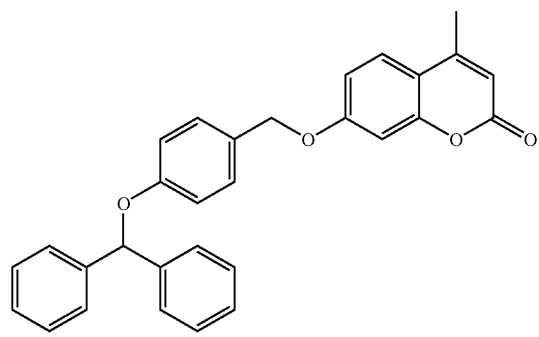
SU010B-02
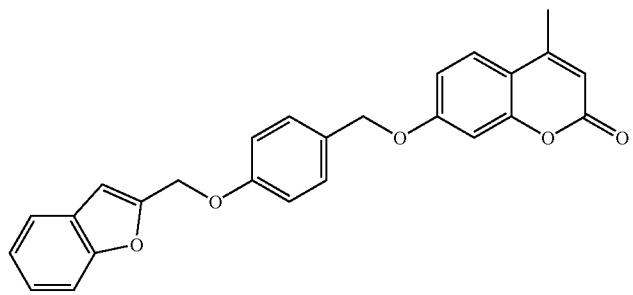
VG021-03
(†)
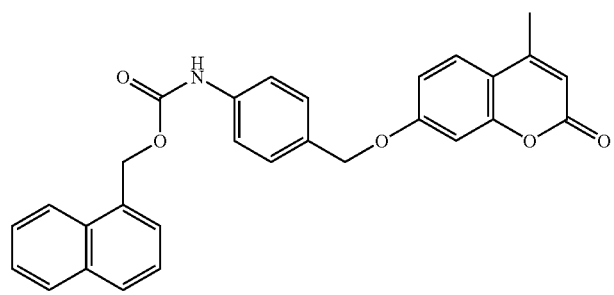
SU024-1-03
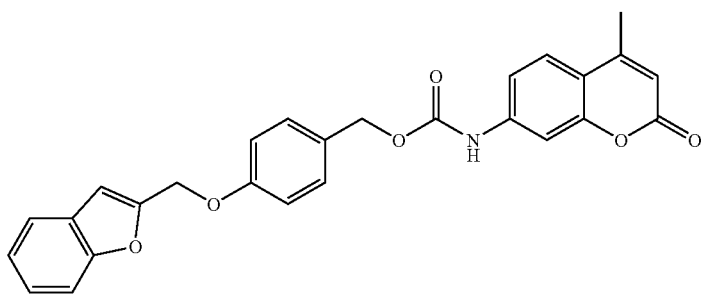

VG040-05

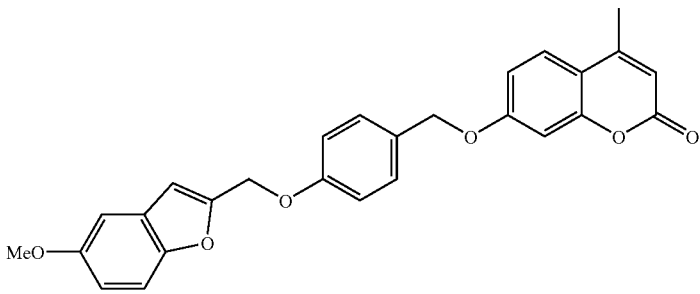

SU032-02
(†)

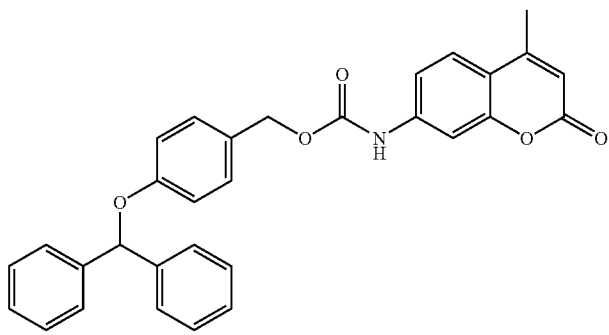

4-methyl-7-(4-naphthalen-1-ylmethoxy)benzyloxy)-2H-chromen-2-one (91) TLE-M1-SU001B

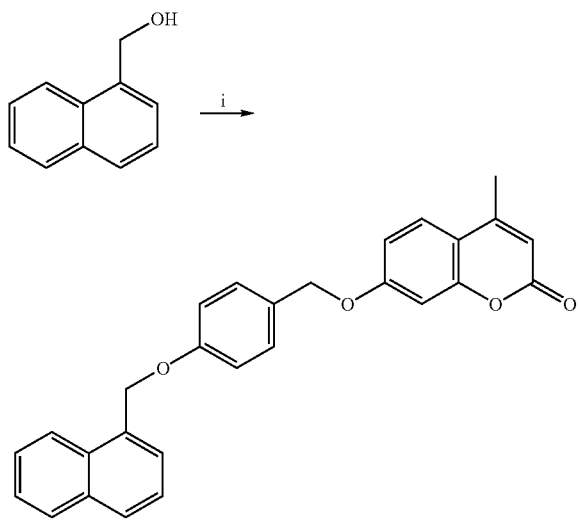

91
TLE-M1-SU001B

Reagents and conditions: (i) a. Sodium ethoxide, ethyl 4-hydroxybenzoate, DMF, rt, 16 h; b. LiAlH$_4$, THF, rt, 3 h; c. PBr$_3$, pyridine, toluene, rt, 1h; d. Sodium ethoxide, 7-hydroxy-4-methylcoumarin, DMF, rt, 16 h.

A suspension of sodium ethoxide (924 mg, 13.6 mmol) in DMF was stirred at 0° C. for 10 min. Ethyl 4-hydroxy benzoate (2.26 g, 13.6 mmol) was slowly added and resulting mixture was stirred at this temp for 0.5 h, then allowed to reach room temp. To this mixture 1-(bromomethyl)naphthalene (2.0 g, 9.0 mmol) was added dropwise [(predissolved in DMF (5 mL)]. Resulting mixture was stirred at room temperature for 16 h. DMF was evaporated off in-vacuo and the residue taken up in EtOAc, and washed with brine, water and 1M NaOH (2×30 mL). The organic layer was dried (MgSO$_4$) and the solvent evaporated off in-vacuo to yield ethyl 4-(naphthalene-1-ylmethoxy)benzoate (1.7 g, 5.55 mmol). This was then dissolved in THF and LiAlH$_4$ (211 mg, 5.55 mmol) was added portionwise, with vigorous stirring. The suspension was stirred at room temperature for 3 h. THF was evaporated off in-vacuo. The crude residue was taken up in EtOAc and washed with water, brine and dried (MgSO$_4$). EtOAc was evaporated off in-vacuo to obtain (4-(naphthalene-1-ylmethoxy)phenyl)methanol (1.3 g, 4.9 mmol) as a crude product. This was used in the next reaction step without further purification. (4-(naphthalen-1-ylmethoxy)phenyl) methanol (1.0 g, 3.8 mmol) was dissolved in toluene (30 mL) and pyridine (305 uL, 3.8 mmol) was added. The solution was cooled to 0° C. PBr$_3$ (359 uL, 3.8 mmol) was added dropwise over 15 min. The mixture was brought up to room temperature and stirred for 1 h. It was washed with K$_2$CO$_3$ solution and extracted with EtOAc (3×30 mL). The EtOAc layer was washed with brine and dried (MgSO$_4$). The solvent was evaporated off in-vacuo to obtain 1-((4-(bromomethyl)phenoxy)methyl)naphthalene (660 mg, 53%). This intermediate was used in the following reaction.

Sodium ethoxide (156 mg, 2.29 mmol) was added to DMF at 0° C., and the suspension was stirred for 10 min. 7-Hydroxy-4-methylcoumarin (403 mg, 2.29 mmol) was slowly added and resulting mixture was stirred for 0.5 h, and then allowed to reach room temperature. To this mixture 1-((4-(bromomethyl)phenoxy)methyl)naphthalene (500 mg, 1.53 mmol) was added portionwise. Resulting mixture was stirred at room temperature for 16 h. DMF was evaporated off in-vacuo and the residue was taken up in EtOAc, and washed with brine (2×50 mL), water (2×50 mL) and 1M NaOH (2×30 mL). The organic layer was dried (MgSO$_4$) and purified by flash chromatography, eluting with hexane: EtOAc (2:1) to give 91 (200 mg, 31%) as a white solid, Mpt=154-156° C.; H$^1$ NMR (500 MHz, acetone-d$_6$): δ=8.10 (1H, d, ArH), 8.00-7.99

(2H, m, Ar), 7.97-7.71 (2H, m, ArH), 7.70-7.53 (3H, m, ArH), 7.24 (1H, s, ArH), 7.09 (1H, d, CH), 6.23 (1H, s, CH), 5.68 (2H, s, CH$_2$), 2.40 (3H, s, CH$_3$). $^{13}$C NMR (500 MHz, acetone-d$_6$, DEPT 135): δ=154.6 (qC), 153.4 (qC), 133.3 (qC), 131.1, 129.8, 128.9, 128.7, 128.5, 126.9, 126.7, 126.5, 126.4, 126.0, 125.9 (11×Ar CH), 125.3, (Ar CH), 123.8 (Ar CH), 114.8 (Ar CH), 113.1 (Ar CH), 112.7 (Ar CH), 111.2 (Ar CH), 111.1 (Ar CH), 101.7 (CH), 69.6 & 67.9 (2×CH$_2$), 18.1 (CH$_3$).

7-(4-(benzhydryloxy)benzyloxy)-4-methyl-2H-chromen-2-one (92) TLE-M1-SU004B

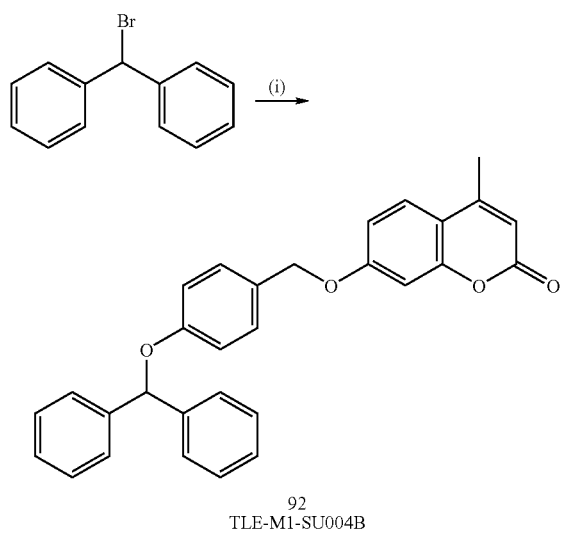

92
TLE-M1-SU004B

Reagents and conditions: (i) a. Sodium ethoxide, ethyl 4-hydroxybenzoate, DMF, rt, 16 h; b. LiAlH$_4$, THF, rt, 3 h; c. PBr$_3$, pyridine, toluene, rt, 1h; d. Sodium ethoxide, 7-hydroxy-4-methylcoumarin, DMF, rt, 16 h.

Sodium ethoxide (661 mg, 9.7 mmol) was added to DMF (5 mL) at 0° C. Resulting suspension was stirred for 15 min. Ethyl 4-hydroxy benzoate (1.61 g, 9.7 mmol) was slowly added and resulting mixture was stirred at this temperature for 0.5 h, then allowed to reach room temperature. To this mixture diphenylmethyl bromide (2.0 g, 8.1 mmol) was added portionwise. Resulting reaction mixture was stirred at room temperature for 16 h. DMF was evaporated off in-vacuo and the residue was taken up in EtOAc, and washed with brine, water and 1M NaOH (2×30 mL). The organic layer was dried (MgSO$_4$) and the solvent evaporated off in-vacuo to yield ethyl 4-(benzhydryloxy)benzoate (1.0 g, 3.0 mmol). This was then dissolved in THF (5 mL) and LiAlH$_4$ (114 mg, 3.0 mmol) was added portionwise, with vigorous stirring. The suspension was stirred at room temperature for 3 h. THF was evaporated off in-vacuo. The crude residue was taken up in EtOAc and washed with water, brine and dried (MgSO$_4$). EtOAc was evaporated off in-vacuo to obtain (4-(benzhydryloxy)phenyl)methanol (760 mg, 2.62 mmol) as a crude product. This was used in the next reaction step without further purification.

(4-(Benzhydryloxy)phenyl)methanol (500 mg, 1.72 mmol) was dissolved in toluene (20 ml) and pyridine (139 uL, 1.72 mmol) was added. The solution was cooled to 0° C. PBr$_3$ (163 uL, 1.72 mmol) was added dropwise over 15 min. The resulting mixture was stirred at room temperature for 1 h. It was then washed with saturated K$_2$CO$_3$ solution and extracted with EtOAc (3×30 mL). The EtOAc layer was washed with brine and dried (MgSO$_4$). The solvent was evaporated off in-vacuo to obtain ((4-(bromomethyl)phenoxy)methylene)dibenzene as an oil, (450 mg, 74%). This intermediate was used in the following reaction.

Sodium ethoxide (87 mg, 1.28 mmol) was added to DMF (3 mL) at 0° C., and the suspension was stirred for 10 min. 7-Hydroxy-4-methylcoumarin (225 mg, 1.28 mmol) was slowly added and resulting mixture was stirred at this temperature for 0.5 h, then allowed to reach room temperature. To this mixture ((4-(bromomethyl)-phenoxy)methylene)dibenzene (300 mg, 1.53 mmol) was added portionwise. Resulting mixture was stirred at room temperature for 16 h. DMF was evaporated off in-vacuo and the residue was taken up in EtOAc, and washed with brine (2×50 mL), water (2×50 mL) and 1M NaOH (2×30 mL). The organic layer was dried (MgSO$_4$) and purified by flash chromatography, eluting with hexane:EtOAc (2:1) to give 92 (80 mg, 21%) as a white solid. Mpt=179-181° C. H$^1$ NMR (500 MHz, acetone-d$_6$): δ=7.66 (1H, d, ArH), 7.56 (4H, d, ArH), 7.39-7.34 (6H, m, ArH), 7.08 (2H, d, ArH), 6.97 (2H, d, ArH), 6.93 (2H, d, ArH), 6.51 (1H, s, CH), 6.12 (1H, s, CH), 5.12 (2H, s, CH$_2$), 2.42 (3H, s, CH$_3$).

7-(4-(benzofuran-2-ylmethoxy)benzyloxy)-4-methyl-2H-chromen-2-one (94) SU010B-02

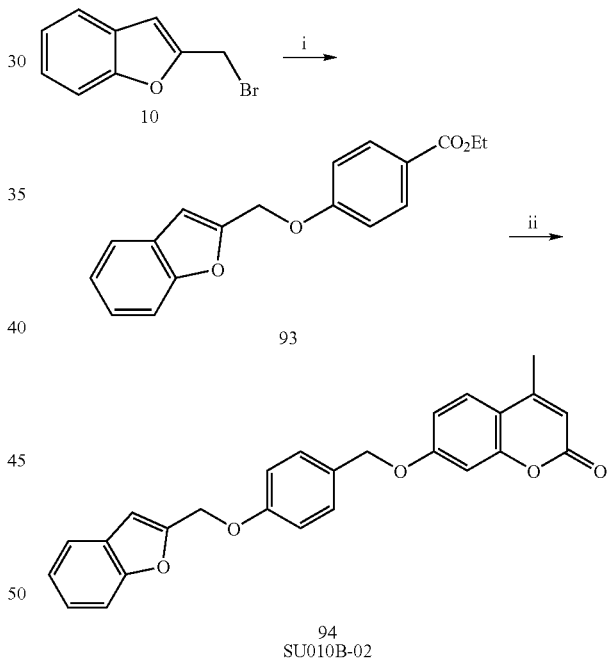

94
SU010B-02

Reagents and conditions: (i) Sodium ethoxide, ethyl 4-hydroxybenzoate, DMF, rt, 2 h; (ii) a. LiAlH$_4$, THF, rt, 1 h; b. PBr$_3$, pyridine, toluene, rt, 1h; c. Sodium ethoxide, 7-hydroxy-4-methylcoumarin, DMF, rt, 16 h.

Ethyl 4-(benzofuran-2-ylmethoxy)benzoate (93)

Sodium ethoxide (580 mg, 8.5 mmol) was added to DMF (10 mL) at 0° C. Resulting suspension was stirred for 15 min. Ethyl 4-hydroxy benzoate (1.4 g, 8.5 mmol) was slowly added and resulting mixture was stirred at this temperature for 0.5 h, then allowed to reach room temp. To this mixture 10 (1.5 g, 7.1 mmol) was added dropwise, predissolved in DMF (5 mL). Resulting reaction mixture was stirred at room temperature for 2 h. DMF was evaporated off in-vacuo and the residue was taken up in EtOAc, and washed with brine, water and 1M NaOH (2×30 mL). The organic layer was dried (MgSO$_4$) and the solvent evaporated off in-vacuo to give 93 as a white solid (920 mg, 44%). m/z=423.18 (M+H). H$^1$ NMR (500 MHz, Acetone-d$_6$): δ=8.0 (2H, d, ArH), 7.60 (1H, d, ArH), 7.30-7.15 (2H, m, ArH), 7.27-7.19 (1H, m, CH), 7.00 (2H, d, ArH), 6.80 (1H, s, CH), 5.20 (2H, s, CH$_2$), 4.10 (2H, q, CH$_2$), 1.25 (3H, t, CH$_3$).

7-(4-(benzofuran-2-ylmethoxy)benzyloxy)-4-methyl-2H-chromen-2-one (94) U010B-02

Compound 93 (400 mg, 1.29 mmol) was dissolved in THF (15 mL) and LiAlH$_4$ (49 mg, 1.29 mmol) was added portionwise, with vigorous stirring. The suspension was stirred at room temperature for 1 h. THF was evaporated off in-vacuo. The crude residue was taken up in EtOAc and washed with water, brine and dried (MgSO$_4$). EtOAc was evaporated off in-vacuo to obtain (4-(benzofuran-2-ylmethoxy)phenyl)methanol (220 mg, 67%) as a crude product. This was dissolved in toluene (10 mL). The solution was cooled to 0° C. PBr$_3$ (98 μL, 1.04 mmol) was added dropwise over 15 min. The resulting mixture was stirred at room temperature for 1 h. It was then washed with saturated K$_2$CO$_3$ solution and extracted with EtOAc (3×30 mL). The EtOAc layer was washed with brine and dried (MgSO$_4$). The solvent was evaporated off in-vacuo to obtain 2-((4-(bromomethyl)phenoxy)methyl)benzofuran as a colourless oil, (132 mg). This intermediate was used in the following reaction.

Sodium ethoxide (43 mg, 0.63 mmol) was added to DMF at 0° C., and the suspension was stirred for 10 min. 7-Hydroxy-4-methylcoumarin (110 mg, 0.63 mmol) was slowly added and resulting mixture was stirred at this temperature for 0.5 h, then allowed to reach room temperature. To this mixture 93 (132 mg, 0.42 mmol) was added portionwise. Resulting reaction mixture was stirred at room temp for 16 h. DMF was evaporated off in-vacuo and the residue was taken up in EtOAc, and washed with brine (2×50 mL), water (2×50 mL) and 1M NaOH (2×30 mL). The organic layer was dried (MgSO$_4$) and purified by flash chromatography, eluting with hexane:EtOAc (2:1) to give 94 (80 mg, 47%) as a white solid. Mpt=153-155° C. m/z=413 (M+H). H$^1$ NMR (500 MHz, Acetone-d$_6$): δ=7.56-7.46 (2H, m, CH), 7.40 (1H, t, J=8.2, CH), 7.34 (2H, d, J=8.50, CH), 7.27-7.19 (1H, m, CH), 7.14-7.09 (1H, m, CH), 7.00-6.98 (2H, d, CH, J=11.8), 6.86-6.80 (3H, m, CH), 5.99 (1H, s, CH), 5.14 (2H, s, CH$_2$), 5.03 (2H, s, CH$_2$), 2.28 (3H, s, CH$_3$).

Naphthalen-1-ylmethyl 4-((4-methyl-2-oxo-2H-chromen-7 yloxy)methyl)phenylcarbamate (95) VG021-03

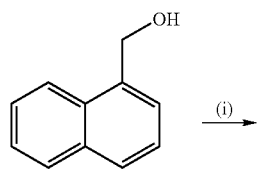

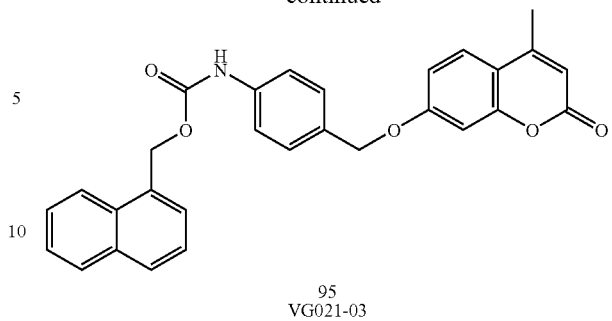

95
VG021-03

Reagents and conditions: (i) a. ethyl cyanobenzoate, TEA, THF, rt, 16 h; b. LiAlH$_4$, THF, rt, 1 h; c. PBr$_3$, pyridine, toluene, rt, 1 h: d. Sodium ethoxide, 7-hydroxy-4-methylcoumarin, DMF, rt, 16 h To a stirred solution of naphthalene methanol (4.0 g, 25.3 mmol) in THF (30 mL) was added TEA (100 uL). To this was added dropwise, ethylcyanobenzoate (4.0 g, 21.0 mmol), pre-dissolved in THF (10 mL). The resulting solution was stirred at room temperature for 16 h. Solvent was evaporated off to give a crude intermediate, ethyl 4-((naphthalen-1-ylmethoxy)carbonylamino)benzoate (1.3 g). This was then dissolved in THF (15 mL) and LiAlH$_4$ (141 mg, 3.75 mmol) was added portionwise, with vigorous stirring. The suspension was stirred at room temperature for 1 h. THF was evaporated off in-vacuo. The crude residue was taken up in EtOAc and washed with water, brine and dried (MgSO$_4$). EtOAc was evaporated off in-vacuo to obtain (naphthalen-1-ylmethyl 4-(hydroxymethyl)phenylcarbamate (500 mg, 1.62 mmol), as a crude product. This was dissolved in toluene (10 mL). The solution was cooled to 0° C. PBr$_3$ (154 uL, 1.62 mmol) was added dropwise over 15 min. The resulting mixture was stirred at room temperature for 1 h. The solvent was evaporated off in-vacuo to obtain naphthalen-1-ylmethyl 4-(bromomethyl)phenylcarbamate as an oil, (300 mg). This intermediate was used in the following reaction without further purification.

Sodium ethoxide (44 mg, 0.65 mmol) was added to DMF at 0° C., and the suspension was stirred for 10 min. 7-Hydroxy-4-methylcoumarin (114 mg, 0.70 mmol) was slowly added and the mixture was stirred at this temperature for 0.5 h, then allowed to reach room temperature. To this mixture 2-((4-(bromomethyl)phenoxy)methyl)benzofuran (200 mg, 0.42 mmol) was added portionwise. Resulting mixture was stirred at room temperature for 16 h. DMF was evaporated off in-vacuo and the residue was taken up in EtOAc, and washed with brine (2×50 mL), water (2×50 mL) and 1M NaOH (2×30 mL). The organic layer was dried (MgSO$_4$) and purified by flash chromatography, eluting with hexane: EtOAc (2:1) to give 95 (160 mg, 63%) as a white solid; Mpt=153-155° C. m/z=488.2 (M+H). H$^1$ NMR (500 MHz, Acetone-d$_6$): δ=7.56-7.46 (2H, m, CH), 7.40 (1H, t, J=8.2, CH), 7.34 (2H, d, J=8.50, CH), 7.27-7.19 (1H, m, CH), 7.14-7.09 (1H, m, CH), 7.00-6.98 (2H, d, CH, J=11.8), 6.86-6.80 (3H, m, CH), 5.99 (1H, s, CH), 5.14 (2H, s, CH$_2$), 5.03 (2H, s, CH$_2$), 2.28 (3H, s, CH$_3$).

4-(benzofuran-2-ylmethoxy)benzyl 4-methyl-2-oxo-2H-chromen-7-ylcarbamate (96) SU024-1-03

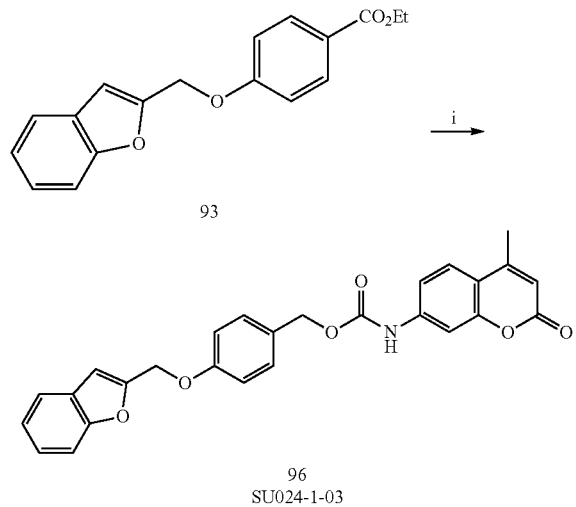

Reagents and conditions: (i) a. LiAlH₄, THF, rt, 1h; b. Sodium exthoxide, DMF, rt, c. 76, rt, 2 h.

Compound 93 (300 mg, 1.01 mmol) was dissolved in THF (15 mL) and LiAlH₄ (38 mg, 1.01 mmol) was added portionwise, with vigorous stirring. The suspension was stirred at room temperature for 1 h. THF was evaporated off in-vacuo. The crude residue was taken up in EtOAc and washed with water, brine and dried (MgSO₄). EtOAc was evaporated off in-vacuo to obtain (4-(benzofuran-2-ylmethoxy)phenyl) methanol (150 mg, 0.59 mmol), as a crude product. This was used in the next step without further purification.

Sodium ethoxide (40 mg, 0.59 mmol) was added to DMF at 0° C., and the suspension was stirred for 10 min. (4-(benzofuran-2-ylmethoxy)phenyl)methanol (150 mg, 0.59 mmol), was added and resulting mixture was stirred at this temperature for 0.5 h, then allowed to reach room temperature. To this mixture 76 (130 mg, 0.65 mmol) was added portionwise. Resulting mixture was stirred at room temperature for 2 h. DMF was evaporated off in-vacuo. The crude residue was purified by flash chromatography, eluting with hexane:EtOAc (2:1) to give the target compound (20 mg, 8%) as a white solid. m/z=456.10 (M+H). H¹ NMR (500 MHz, DMSO-d₆): δ=10.22 (1H, bs, NH), 7.69-7.64 (2H, m, ArH), 7.58 (1H, d, J=8.15 Hz, ArH), 7.55 (1H, s, ArH), 7.42 (2H, d, J=8.00 Hz, ArH), 7.33 (1H, t, J=7.70 Hz, ArH), 7.26 (1H, t, J=7.5 Hz, ArH), 7.11 (2H, d, J=8.28 Hz, ArH), 7.06 (1H, s, ArH), 6.23 (1H, s, ArH), 5.29 (2H, s, CH₂), 5.12 (2H, s, CH₂), 2.37 (3H, s, CH₃).

7-(4-((5-methoxybenzofuran-2-yl)methoxy)benzyloxy)-4-methyl-2H-chromen-2-one (97) VG040-05

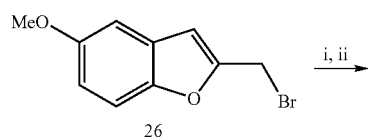

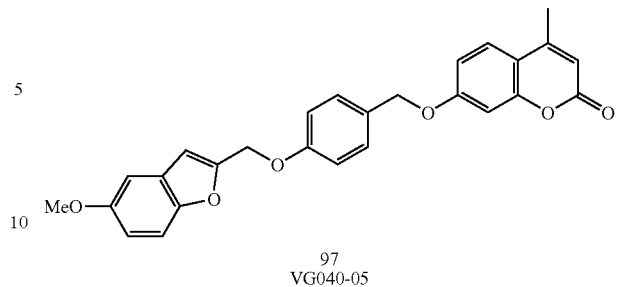

Reagents and conditions: (i) Sodium ethoxide, ethyl 4-hydroxybenzoate, DMF, rt, 2 h; (ii) a. LiAlH₄, THF, rt, 1 h; b. PBr₃, pyridine, toluene, rt, 1h; c. Sodium ethoxide, 7-hydroxy-4-methylcoumarin, DMF, rt, 16 h.

Sodium ethoxide (62 mg, 0.90 mmol) was added to DMF (3 mL) at 0° C. Resulting suspension was stirred for 15 min. Ethyl 4-hydroxy benzoate (148 mg, 0.90 mmol) was slowly added and resulting mixture was stirred at this temperature for 0.5 h, then allowed to reach room temperature. To this mixture 26 (180 mg, 0.75 mmol) was added. Resulting reaction mixture was stirred at room temperature for 1 h. DMF was evaporated off in-vacuo to give a crude intermediate (150 mg). This was then dissolved in THF (5 mL) and LiAlH₄ (34 mg, 0.90 mmol) was added portionwise, with vigorous stirring. The suspension was stirred at room temperature for 1 h. THF was evaporated off in-vacuo. The crude residue was taken up in EtOAc and washed with water, brine and dried (MgSO₄). EtOAc was evaporated off in-vacuo to obtain (4-((5-methoxybenzofuran-2-yl)methoxy)phenyl)methanol (120 mg) as a crude product. This was dissolved in toluene (4 mL). The solution was cooled to 0° C. PBr₃ (84 µL, 1.04 mmol) was added dropwise over 5 min. The resulting mixture was stirred at room temperature for 1 h. The solvent was evaporated off in-vacuo to obtain 2-((4-(bromomethyl)phenoxy)methyl)-5-methoxybenzofuran as a colourless oil, (90 mg). This intermediate was used in the following reaction.

Sodium ethoxide (22 mg, 0.31 mmol) was added to DMF (2 mL) at 0° C., and the suspension was stirred for 10 min. 7-Hydroxy-4-methylcoumarin (54 mg, 0.31 mmol) was slowly added and resulting mixture was stirred at this temperature for 0.5 h. To this mixture 2-((4-(bromomethyl)phenoxy)methyl)-5-methoxybenzofuran (90 mg, 0.23 mmol) was added portionwise. Resulting reaction mixture was stirred at room temp for 16 h. DMF was evaporated off in-vacuo and the residue was purified by flash chromatography, eluting with hexane:EtOAc (1:1) to give 94 (22 mg, 7%) as a white solid. m/z=443 (M+H).

4-(benzhydryloxy)benzyl 4-methyl-2-oxo-2H-chromen-7-ylcarbamate (98) SU032-02

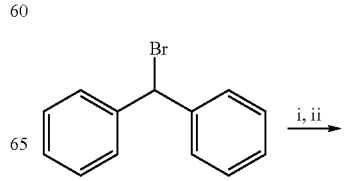

-continued

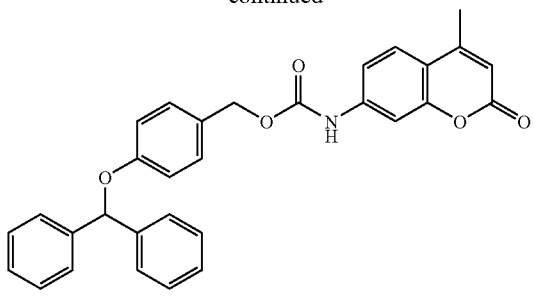

98
SU032-02

Reagents and conditions: (i) a. Sodium ethoxide, ethyl 4-hydroxybenzoate, DMF, rt, 16 h; b. LiAlH$_4$, THF, rt, 3 h; (ii) Sodium ethoxide, DMF, 76, rt, 2 h.

Sodium ethoxide (300 mg, 4.05 mmol) was added to DMF (10 mL) at 0° C. Resulting suspension was stirred for 10 min. Ethyl 4-hydroxy benzoate (739 mg, 4.05 mmol) was slowly added and resulting mixture was stirred at this temperature for 20 min. To this mixture diphenylmethyl bromide (1.0 g, 4.05 mmol) was added portionwise. Resulting reaction mixture was stirred at room temperature for 16 h. DMF was evaporated off in-vacuo and the residue was taken up in EtOAc, and washed with water and brine. The organic layer was dried (MgSO$_4$) and the solvent evaporated off in-vacuo to yield ethyl 4-(benzhydryloxy)benzoate (830 mg). This was then dissolved in THF (5 mL) and LiAlH$_4$ (114 mg, 3.0 mmol) was added portionwise, with vigorous stirring. The suspension was stirred at room temperature for 3 h. THF was evaporated off in-vacuo. The crude residue was taken up in EtOAc and washed with water, brine and dried (MgSO$_4$). EtOAc was evaporated off in-vacuo to obtain (4-(benzhydryloxy)phenyl) methanol (760 mg, 2.62 mmol) as a crude product. This was used in the next reaction step without further purification.

A solution of (4-(Benzhydryloxy)phenyl)methanol (100 mg, 0.34 mmol) and 76 in toluene (10 ml). was refluxed for 2 h. The reaction was allowed to cool to room temperature and the resulting precipitate formed was filtered and washed with cold ether and EtOAc to give 98 (100 mg, 60%) as a white solid. m/z=491.55 (M+H).

BIOLOGICAL ACTIVITY

Example 1

CYP1B1 Metabolism of Prodrugs

Substituent Effect on the Fragmentation of Benzofuran Ether and Carbamate Linked Coumarins by CYP1 Isoenzymes and Human Liver Microsomes (HLM).

Commercially available Supersomal™ CYP1A1, CYP1A2, CYP1B1, and pooled human liver microsomes (supplied BD Gentest, Oxford, UK) comprised an enzymatic screen to identify structure activity relationships (SARs) underlying the structural features which control the efficiency and selectivity of prodrug fragmentation by CYP1B1 expressed in cancer relative to cytochrome P450 enzymes expressed in normal tissues including the liver. HLMs are derived from human patient liver and according to the supplier contain a battery of cytochrome P450s including CYP1A2, CYP2A6, CYP2B6, CYP2B6, CYP2C8, CYP2C9, CYP2D6, CYP2E1, CYP3A4, and CYP4A but not CYP1A1 or CYP1B1.

Typical Supersomal™ CYP1A1, CYP1A2, CYP1B1 enzyme metabolism studies used 10 µmol enzyme, 100 µmol dm$^{-3}$ NADPH, in 10 mmol dm$^{-3}$ potassium phosphate buffer at pH 7.4 and 37° C. Supersomal™ enzyme metabolism was started by adding a stock solution of prodrug dissolved in DMSO to give a final concentration of 10 µmol dm$^{-3}$ prodrug and 0.5% DMSO. HLM screening used 60 microlitre microsomes, 100 µmol dm$^{-3}$ NADPH, in 10 mmol dm$^{-3}$ potassium phosphate buffer at pH 7.4 and 37° C., in 1.5 ml total reaction volume.

Compounds of the invention comprise a series of heteroaromatic triggers coupled to ether and carbamate linkers to the hydroxyl group of 7-hydroxy-4-methycoumarin and 7-amino-4-methylcoumarin, respectively. Further examples of the invention comprise compounds were heteroaromatic triggers are coupled via the so-called extended oxybenzyl ether linker (—Ar—CH(Z$^7$)X$^3$—=-phenyl-CH$_2$O—) to the hydroxyl group of 7-hydroxy-4-methycoumarin. Further examples of the invention comprise compounds where heteroaromatic triggers are coupled via the so-called extended oxybenzyl carbamate linker to the amino group of 7-amino-4-methycoumarin. Further examples of the invention comprise compounds where heteroaromatic triggers are coupled via a carbamate benzyl ether linker to the hydroxyl group of 7-hydroxy-4-methycoumarin.

Both 7-hydroxy-4-methycoumarin and 7-amino-4-methylcoumarin are partially deprotonated at physiological pH 7.4 and both coumarin anions are highly fluorescent with fluorescence emission wavelength maxima of 450 and 445 nm, respectively. When the coumarins are coupled to hetero-aromatic triggers via linkers described in this invention the fluorescence of the coumarin anion is quenched. Therefore, enzymatic hydroxylation of the hetero-aromatic trigger and resultant linker fragmentation can be monitored in real time by release of the coumarin anion by kinetic fluorimetry. This prodrug design strategy has been successfully used to monitor the fragmentation of so-called bioreductive hypoxia-activated prodrugs by P450 reductase not to be confused with CYP1B1 which is a mono-oxygenase enzyme (See, e.g.: Everett S A et al., Modifying rates of reductive elimination of leaving groups from indolequinone prodrugs: a key factor in controlling hypoxia-selective drug release", Biochem Pharmacol., 63: 1629-39, 2002).

Release of the coumarin anion indicative of linker fragmentation was monitored using a 1 cm path length fluorescence cell in a Cary Eclipse kinetic flourimeter with excitation and emission slits set at 5 nm. Coumarin anion release from compounds of the invention was detected at the excitation wavelength $\lambda_{ex}$=350 nm and the emission wavelength $\lambda_{em}$=450 nm. Change in fluorescence intensity was quantified against a linear calibration plot of fluorescence intensity versus coumarin concentration (0 to 3.5 µmol dm$^{-3}$) in 10 mmol dm$^{-3}$ potassium phosphate buffer at pH 7.4 using the same instrument settings as for enzyme metabolism.

Specific fragmentation activities (in pmol coumarin min$^{-1}$ µmol cytochrome P450$^{-1}$) for the CYP1 isoenzyme and HLM-activated fragmentation and release of coumarin from benzofuran ether and carbamate-linked coumarins are shown in Table 3. An electron donating substituent (Me, MeO) or electron withdrawing substituents (Cl, Br, F) in one or both of the 5- and 7-position of the benzofuran has a significant effect on both fragmentation specificity and efficiency. The 4- and 6-positions on the benzofuran are left unsubstituted (R$^4$ and R$^6$=H) as they are likely positions for enzymatic hydroxylation necessary to induce ether or carbamate linker fragmentation according to the proposed mechanism. The structure activity relationship (SAR) governing the substituent effect at the 5- and 7-position on the benzofuran and CYP1 isoenzyme-induced fragmentation efficiency and selectivity are not predictable for either ether or carbamate linker fragmentation.

SU10A (see Table 3 below) where $Z^3$=H, $Z^5$=H bearing an ether-linked coumarin is fragmented by CYP1A1, CYP1A2, and CYP1B1 as well as HLM. For HLM the inclusion of 10 μmol dm$^{-3}$ α-naphthoflavone (a CYP1-selective enzyme inhibitor) inhibits SU10A fragmentation indicating that CYP1A2 is solely responsible for HLM-mediated coumarin release. Benzofuran is therefore a generic trigger moiety that can facilitate the fragmentation of ether-linked prodrugs by CYP1 isoenzymes.

Electron withdrawing substituents on the benzofuran in VG016-04 (see also Table 3 below) where $Z^3$=F, $Z^5$=F inhibits CYP1 isoenzyme and HLM-induced fragmentation of the ether linker. However, electron donating substituents in VG035-05 (see also Table 3 below) where $Z^3$=MeO, $Z^5$=MeO results in CYP1B1-specific fragmentation of the ether bond as no linker fragmentation is observed for CYP1A or HLM. The specific fragmentation activity for VG035-05 with CYP1B1 is 13.65±1.00 pmol coumarin min$^{-1}$ pmol cytochrome P450$^{-1}$ is the highest efficiency of the various benzofuran ether-linked coumarins investigated (see Table 3 below). The 5,7-dimethoxybenzofuran moiety can therefore be used to specifically trigger the fragmentation of ether-linked prodrugs by CYP1B1 an enzyme which is over-expressed in cancer.

In marked contrast to VG035-04 (which contains an ether-linked coumarin), VG041-05 (which contains the corresponding carbamate-linked coumarin) where $Z^3$=MeO, $Z^5$=MeO is selectively fragmented by CYP1A1 (but not CYP1A2 or CYP1B1) with a specific fragmentation activity=5.51±0.06 μmol coumarin min$^{-1}$ μmol cytochrome P450$^{-1}$. According to Table 3 below all compound examples of structure B containing a carbamate linker are fragmented by CYP1A1 but not CYP1B1. The only exception is VG032-05 where $X^3$=MeO, $Z^5$=MeO giving a CYP1B1 specific fragmentation activity=1.53±0.09 μmol coumarin min$^{-1}$ μmol cytochrome P450$^{-1}$, which is ~6-fold lower than VG027-05 which contains an ether linker.

Example 2

Combining the Model Prodrug Library with a CYP1B1 Substrate Prediction Model Links Substrate Specificity to Prodrug Activation and Fragmentation Performing a High-Throughput Screen (HTS) to Build a Bioactivity Dataset for CYP1B1

The target enzyme CYP1B1 was screened against two commercial libraries including the ChemDiv Diversity 50,000 test compound collection and the ChemDiv Kinase Targeted 10,000 test compound collection with a view to identifying activity differentiating substructures and a large bioactivity dataset from which to build a substrate specificity model. The HTS was performed in miniaturized 384-well format using a liquid handler (Beckman FXp), bulk dispensers (Matrix Wellmate) and a luminescent plate reader (Molecular Devices Analyst AD plate Reader). P450-Glo™ Assays provide a luminescent method for measuring cytochrome P450 activity. A conventional reaction is performed by incubating the human supersomal CYP1B1 plus reductase (BD Gentest™, UK) recombinant enzyme with a luminogenic cytochrome P450 substrate, namely Luciferin 6' chloroethyl ether (Luciferin-CEE) which is a substrate for CYP1B1 but not for luciferase. Luciferin-CEE is converted to a luciferin product that is detected in a second reaction with Luciferin Detection Reagent (CYP1B1 Luminescent Assay Kit, P450-Glo™ from Promega, Madison, USA). The reagent simultaneously stops the cytochrome P450 reaction and initiates a stable luminescent signal with a half-life>2 h. The amount of light produced in the second reaction is proportional to the activity of CYP1B1. The biochemical end-point was substrate inhibition of the enzyme (0.5 μmol/well) working at the apparent $K_m$ for Luciferin-CEE (20 μmol dm$^{-3}$). The assay is characterized by excellent Z'-factors typically greater than 0.6 (where a Z'=1.0 denotes a perfectly robust highly reproducible assay) when run in 384-well format. The negative control was the level of activity which defined the unmodified state of the enzyme target while the positive control was the level of activity which defined a hit. The negative control contained the CYP1B1/KPO$_4$/NADPH/substrate reaction mixture and an equivalent concentration of 1% DMSO used for solubilization of the test compounds. The positive control in the assay contained the CYP1B1/KPO$_4$/NADPH substrate reaction mixture with α-naphthoflavone which completely inhibits CYP1B1 enzyme activity at a final concentration of 5 μmol dm$^{-3}$. The positive and negative controls were deposited in the outer columns of every 384-well plate with the test compounds deposited in the remaining 320 wells. The definition of a hit is a test compound that is a substrate inhibitor CYP1B1 activity by 80-100% at a concentration of 0.5 μmol dm$^{-3}$.

Pipeline Pilot (Scitegic, San Diego, USA) was used to streamline and integrate the large quantity of data to identify SARs from the CYP1B1 HTS, supported by computational scientists at the UCSF SMDC. The software was used to identify (1) preliminary SAR results of hits versus non-hits, (2) determine physicochemical properties e.g. molecular weight, calculated log P, H-atom donor/acceptor interactions of the hit population, (3) determine the frequency of ring fragments and functional groups, and (4) define an in silico model for the prediction of CYP1B1 substrate inhibition as a basis for future prodrug design. Importantly, s significant number of the hits ~10% had a molecular weight between 400-500, the latter being the maximum molecular weight of test compounds available in both compound collections. This information defined the maximum molecular weight of the prodrug permissible whilst maintaining CYP1B1 substrate specificity. Structural analysis of hit scaffolds in SARvision v2 from CHEMAPPS™ (La Jolla, Calif., USA) confirmed that test compounds did not support the correct functional group (e.g. a trigger hydroxymethyl substituent) for direct integration into the coupling chemistry reviewed in scheme 1. However, by identifying ring fragments of high frequency in hits versus non-hits it was possible to identify templates for trigger moieties which could then be functionalized appropriately for coupling reactions.

An In Silico Model for Predicting Cytochrome P450 Substrate Inhibition in Support of Prodrug Design.

A major challenge in prodrug design is to define the strategy to integrate the trigger, linker and effector chemistry whilst maintaining substrate specificity for the target enzyme. The CYP1B1 HTS was extremely valuable in identifying potential trigger moieties but subsequent 'hit to lead' chemistry incorporating a linker and effector drug could mean that the final prodrug structure would not be optimal for target enzyme activation. Optimal usage of the vast amount of structural data from the two HTS screens (totaling 60,000 test compounds) was achieved by developing an in silico prediction model of cytochrome P450 1B1 substrate inhibition using Gaussian Kernel weighted k-nearest neighbour (k-NN) algorithm based on Tanimoto similarity searches on extended connectivity fingerprints. The optimal parameters of the CYP1B1 kernel weighted k-NN model were chosen using leave-one-out cross validation on a training set selected from 45,000 and 9,000 test compounds from the ChemDiv Diverse and Kinase libraries. The remainder of the test compounds, 6,000 in total, were used as an internal test set to confirm the accuracy of the model to predict substrate inhibition. Any test compounds exhibiting >20 but <80% inhibition were designated non-classified. The model accurately predicted 89% of the classified non-substrate inhibitors and 95% of the classified substrate inhibitors. CYP1B1 substrate prediction model protocol was uploaded into the Scitegic Web Port to facilitate the docking of putative prodrug structures through an interface to standard chemistry drawing packages such as ChemDraw/IsisDraw.

Validation of the CYP1B1 Substrate Prediction Model Using an External Test Set of Compounds A 384-well stock plate constituting an external test set for the CYP1B1 substrate prediction model was constructed and included: (1) known CYP1B1 substrate inhibitors including, for example, tetramethoxystilbene, β-estradiol, α-napthoflavone, ethoxyresorufin, resveratrol, (2) compounds which are not CYP1B1 substrate inhibitors including, for example, quinidine (a potent specific inhibitor of CYP2D6), sulfaphenazole (a potent specific inhibitor of CYP2C9), and (3) the model prodrugs VG016-05 and VG035-05, and (4) and the phosphoramidate mustard prodrugs SU025-04 and SU046-04. The external test set stock concentration was 10 mmol dm$^{-3}$ in DMSO and the percentage CYP1B1 substrate inhibition at a final concentration of 0.5 mmol dm$^{-3}$ was determined using the same methods described for the main CYP1B1 HTS. Experiments were performed in triplicate to give a mean % substrate inhibition of CYP1B1 activity±standard deviation. All the external test set structures were submitted as queries to the CYP1B1 substrate prediction model via the Scitegic Web Port to generate predicted values of % substrate inhibition of CYP1B1 in order to compare with the actual biochemical measurement of % substrate inhibition.

The comparative actual and predicted % substrate inhibition for CYP1B1 values were as follows:

| compound | % CYP1B1 substrate inhibition | | |
|---|---|---|---|
|  | actual | predicted | accuracy |
| tetramethoxystilbene | 95.76 ± 0.33 | 97.34 | 98% |
| β-estradiol, | 72.34 ± 0.45 | 76.12 | 95% |
| α-napthoflavone | 99.12 ± 0.23 | 92.45 | 93% |
| ethoxyresorufin | 92.13 ± 0.56 | 87.23 | 95% |
| resveratrol | 72.34 ± 0.56 | 76.45 | 95% |
| sulfaphenazole | 2.89 ± 0.15 | 4.25 | 68% |
| quinidine | 1.63 ± 0.34 | 2.56 | 64% |
| VG016-05 | 2.45 ± 0.32 | 2.98 | 82% |
| VG035-05 | 97.34 ± 0.32 | 93.56 | 96% |
| SU025-04 | 91.22 ± 0.48 | 87.36 | 96% |
| SU046-04 | 96.45 ± 0.22 | 92.34 | 96% |

The CYP1B1 substrate prediction model was accurate in predicting % substrate inhibition of CYP1B1 across multiple classes of compound with a broad range of activity confirming validation of the model using an external test set of compounds. Importantly, in terms of an inventive step the model was accurately able to predict the activity of the two model prodrugs VG016-05 and VG035-05 in terms of CYP1B1 substrate inhibition which can be linked directly to the efficiency of prodrug fragmentation and release of the 7-hydroxy-4-methy coumarin anion. According to Table 3 electron donating or electron withdrawing substituents in the $R^5$ and $R^7$ of the benzofuran trigger activate these model prodrugs to aromatic hydroxylation and fragmentation. When $R^5$ and $R^7$=F, i.e. electron withdrawing substituents as in VG016-05 the model prodrug is not activated by CYP1B1 as accurately predicted and as a consequence there is no fragmentation of the linker. In marked contrast when $R^5$ and $R^7$=MeO, i.e. electron donating substituents as in VG035-05 the model prodrug is activated by CYP1B1 as accurately predicted resulting in fragmentation of the linker with high efficiency. Incorporation of the dimethoxybenzofuran trigger moiety into the phosphoramidate mustard prodrugs SU025-04 and SU046-04 generate compound which are accurately predicted to be good substrate inhibitors of CYP1B1. In conclusion, the combination of model prodrug libraries and CYP1B1 substrate prediction models based on a database of CYP1B1 bioactivity facilitate the design of specific CYP1B1-activated prodrugs.

Example 3

Prodrug Cytotoxicity in Wild-Type CHO Cells and CHO Cells Engineered to Express CYP1A1 and CYP1B1 Isozymes Engineered CHO cells were used to demonstrate selective cell killing mediated by CYP1 expression. In the experiments described below, compounds were exposed to wild-type CHO cells engineered to express either CYP1A1 (CHO/CYP1A1) or CYP1B1 (CHO/CYP1B1) enzymes.

CHO cells: Chinese Hamster Ovary (CHO) DUKXB11 cells were grown under standard cell culture conditions in α-MEM supplemented with 10% FCS, 1 unit/ml each of hypoxanthine and thymidine, and penicillin (100 IU/ml) and streptomycin (100 μg/ml) according to literature methods (Ding S, et al., *Arch. Biochem. Biophys.*, 348: 403-410, 1997, the contents of which are incorporated herein by reference). Cells were grown at 37° C. in a humidified atmosphere plus 5% $CO_2$.

CHO/CYP1A1 and CHO/CYP1B1 cells: CHO cells containing recombinant CYP1A1 and recombinant CYP1B1 co-expressing P450 reductase, namely (CHO/CYP1A1) and (CHO/CYP1B1) respectively, were cultured using the standard culture medium for CHO cells supplemented with 0.4 mg/ml G418 disulfate salt and 0.3 μM methotrexate (Sigma/Aldrich Co., Gillingham, Dorset, UK) according to methods described in the literature (ibid.) Cells were grown at 37° C. in a humidified atmosphere plus 5% $CO_2$.

Recombinant CYP1A1 and CYP1B1 Expression

Dihydrofolate reductase (DHFR) gene amplification of either human cDNA CYP1A1 or cDNA CYP1B1 in CHO cells was used to achieve high levels of functional enzyme when co-expressed with human P450 reductase (ibid.; Ding S, et al., *Biochem J.*, 356 (Pt 2): 613-9, 2001). Modified CYP1A1 or CYP1B1 cDNA was digested and ligated into to the mammalian expression vector pDHFR to generate the plasmids pDHFR/1A1 and pDHFR/1B1, respectively (ibid.) Cell culture and DNA transfection into CHO DUKXB11 was carried out according to methods described in the literature and transfected cells selected for the DHFR+ phenotype by growth in nucleoside deficient medium (ibid.) DHFR+ clones were pooled, and grown on increasing concentrations of MTX (0.02 to 0.1 μM) for amplification of transfected CYP1A1 or CYP1B1 cDNA. Cell clones that survived 0.1 mM MTX selection were isolated then further selected with 0.3 μM MTX. The resulting cell lines were analysed for CYP1A1 or CYP1B1 expression by immunoblotting. Cell lines expressing a high level of each enzyme were stably transfected with plasmid pcDNA/HR containing a full length human cytochrome P450 reductase (CPR) cDNA, and selected with G418 (0.8 mg/ml) and MTX (0.3 µM) according to methods described in the literature (ibid.) After isolation of resistant clones the concentration of G418 was reduced to 0.4 mg/ml and the homogeneity of the cell lines assured by repeated cloning. The CHO cell line transfected with the plasmid carrying cDNA CYP1A1 subsequently transfected with CPR cDNA was designated CHO/CYP1A1 and the CHO cell line transfected with the plasmid carrying cDNA CYP1B1 subsequently transfected with CPR cDNA was designated CHO/CYP1B1.

Immunochemical Detection of CYP1A1 and CYP1B1

Cells were harvested and lysed by sonication using standard methods in the literature (Ding S, et al., 1997, the contents of which are incorporated herein by reference). Proteins (typically 50 µg of lysate) were separated by SDS/PAGE, transferred to a nitrocellulose membrane and probed using standard methods (Paine M J, et al., *Arch. Biochem. Biophys.*, 328: 380-388, 1996, the contents of which are also incorporated herein by reference). Human CYP1A1 plus reductase Supersomes™, human CYP1A2 plus reductase Supersomes™ and CYP1B1 plus reductase Supersomes™ (BD Biosciences, Oxford, UK) were used as positive controls (typically 0.03 to 0.3 pmole) for immunochemical detection of enzyme expression in cell lines. A WB-1B1 primary antibody (dilution 1:1500, BD Biosciences, Oxford, UK) and an anti-CYP1A2 antibody which cross reacts with CYP1A1 (dilution 1:2000, Cancer Research Technology, London, UK) were used to detect CYP1B1 and CYP1A1 expression, respectively. The secondary antibody was goat anti-rabbit IgG used at a 1:500 dilution. Immunoblots were developed using the Enhanced Chemiluminescence (ECL) Western-blot detection kit (GE Healthcare Life Sciences, Amersham, Buckinghamshire, UK).

Western-Blot Characterization of CYP1A1 and CYP1B1 Expression in Engineered CHO Cells FIG. 1a of the accompanying drawings is a typical western-blot showing the detection of CYP1B1 protein expression in lysate from the CHO/CYP1B1 cell line which is detectable in neither the untransfected CHO DUKXB11 cells nor the CHO/CYP1A1 cell line. The band corresponds to a molecular weight of 56 kDa and matches the band for human CYP1B1 Supersomal™ enzyme. FIG. 1b is a typical western-blot showing the detection of CYP1A1 protein expression in lysate from the CHO/CYP1A1 cell line which is detectable in neither the untransfected CHO DUKXB11 cells nor the CHO/CYP1B1 cell line. The band corresponds to a molecular weight of 60 kDa and matches the band for human CYP1A1 Supersomal™ enzyme detected by the cross reactivity of the anti-CYP1A2 antibody.

Functional CYP1 Enzyme Activity

The ethoxyresorufin O-deethylation (EROD) assay is widely used to confirm functional CYP1 activity (Chang T K and Waxman D J, "Enzymatic Analysis of cDNA-Expressed Human CYP1A1, CYP1A2, and CYP1B1 with 7-Ethoxyresorufin as Substrate", *Methods Mol. Biol.*, 320: 85-90, 2006, the contents of which are incorporated herein by reference). The assay determines O-dealkylation of 7-ethoxyresorufin by CYP1A1, CYP1A2, and CYP1B1 to generate the enzymatic product resorufin, which is monitored continuously by fluorescence emission at 580 nm. An alternative assay for measuring enzyme activity is the commercially available Promega P450-Glo™ Assay utilizing Luciferin-CEE as a luminogenic substrate for CYP1 enzymes in Cali J J, et al., *Expert. Opin. Drug Metabolism Toxicol.*, 2(4): 629-45, 2006, the contents of which are also incorporated herein by reference. The EROD assay and Promega P450-Glo™ Assay with selective and non-selective CYP1 inhibitors were used to confirm that the CHO cell lines referred to above were expressing the expected CYP1 enzymes in a functional form.

In the absence of inhibitors, CHO/CYP1A1 and CHO/CYP1B1 (but not wild-type CHO cells) converted 7-ethoxyresorufin to resorufin or Luciferin-CEE to luciferin, thereby confirming functional CYP1 expression in these cells (see Table 1 below).

As expected, addition of the broad-spectrum CYP1 inhibitor, α-naphthoflavone, abolished activity in both CYP1 expressing cell lines (see Table 1 below). The selective inhibitor, tetramethoxystilbene, is 30-fold selective for CYP1B1 over CYP1A1 (Chun Y J, Kim S, Kim D, Lee S K and Guengerich F P, "A New Selective and Potent Inhibitor of Human Cytochrome P450 1B1 and its Application to Antimutagenesis", *Cancer Res* 61(22): 8164-70, 2001). Tetramethoxystilbene abolished activity at high concentrations in both CYP1 expressing cell lines and preferentially decreased activity in CYP1B1 expressing cells (compared with CYP1A1 expressing cells) cells at lower concentrations (see Table 1 below).

These results provide independent confirmation that the CYP1A1 and CYP1B1 expression levels are as expected.

Determining Cytotoxicity $IC_{50}$ Values in CHO, CHO/CYP1A1 and CHO/CYP1B1 Cell Lines A single cell suspension of CHO, CHO/CYP1A1 or CHO/CYP1B1 in 100 µl of the required cell culture medium was seeded onto 96-well plates at a cell density of 1500 cells per well and placed in an incubator for 24 h at 37° C. The stock solution of test compound in DMSO was then added to give a concentration range of 100, 30, 10, 3, 1, 0.3, 0.1, 0.03, 0.01, 0.003, 0.001, 0 µM. The final concentration of DMSO 0.2% was found not to affect the growth characteristics of the various CHO cell lines. The cells were incubated with the test compound for 72 or 96 h after which all the medium was aspirated and replaced with 100 µl of fresh medium to compensate for the loss of medium due to evaporation. The cells were incubated with 20 µl of the MTS assay reagent for 1.5 h and the absorbance per well at 510 nm measured using a plate reader. The mean absorbance and standard deviation for each test compound concentration was calculated versus a series of controls including (a) cells plus medium, (b) cell plus medium containing DMSO 0.2%, (c) medium alone, and (d) medium containing DMSO 0.2% and a range of test compound concentrations from 0 to 100 $\mu mol\, dm^{-3}$. The cytotoxicity $IC_{50}$ value was calculated from the plot of the percentage cell growth (where 100% cell growth corresponds to untreated control cells) versus test compound concentration.

Cytotoxicity $IC_{50}$ values are defined herein as the concentration of compound which kills 50% of cells and fold selectivity is calculated by dividing the $IC_{50}$ in non-CYP1 expressing cells with the $IC_{50}$ in CYP1A1 or CYP1B1 expressing cells. Differential cytotoxicity $IC_{50}$ ratios are calculated from compound $IC_{50}$ in normal CHO cells divided by $IC_{50}$ in CYP1A1 or CYP1B1 transfected CHO cells.

Promega™ CellTiter 96® Aqueous Non-Radioactive Cell Proliferation (MTS) Assay

The commercially available MTS assay is a homogeneous, colorimetric method for determining the number of viable cells in proliferation, cytotoxicity or chemosensitivity assays. The assay is composed of solutions of tetrazolium compound [3-(4,5-dimethylthiazol-2-yl)-5-(3-carboxymethoxyphenyl)-2-(4-sulfophenyl)-2H-tetrazolium, inner salt; MTS] and an electron coupling reagent (phenazine methosulfate) PMS.

MTS is bioreduced by cells into a formazan product that is soluble in tissue culture medium. The absorbance of the formazan product at 510 nm can be directly measured from 96-well assay plates. The quantity of formazan product as measured by the amount of absorbance at 490 or 510 nm is directly proportional to the number of living cells in culture.

Two compounds of the invention (SU025-04 and SU046-04), are designed to release the phosphoramide mustards N,N-bis(2-chloro-ethyl)phosphoramide (Cl-IPM) and N,N-bis(2-bromo-ethyl)phosphoramide (Br-IPM), respectively, when activated by CYP1B1. The high toxicities of the two phosphoramidate mustards Cl-IPM and Br-IPM are significantly reduced when incorporated in the prodrugs SU025-04 and SU046-04, respectively. Both SU025-04 and SU046-04 have cytotoxicity $IC_{50}$ values no less than 10 µmol $dm^{-3}$ in wild-type CHO cells at 72 or 96 h exposure in marked contrast to Cl-IPM and Br-IPM which have cytotoxicity $IC_{50}$ values below 0.007 µmol $dm^{-3}$ in wild-type CHO cells after a 72 h exposure (see Table 2 below). The mechanism of activation of the two prodrugs can be deduced from their comparative cytotoxicity $IC_{50}$ values in CHO-wild-type (which lacks CYP1 enzyme expression), CHO/1A1, and CHO/CYP1B1 cells. For example, SU025 and SU046 exhibit low toxicity in wild-type CHO cells but are highly toxic to CHO/1B1 cells giving differential cytotoxicity $IC_{50}$ ratios of 1689 and 5075, respectively at 72 h exposure. At a longer exposure time of 96 h the CYP1B1-selective prodrugs SU025-04 and SU046-04 are 3367 and 5400-fold more toxic to CYP1B1 expressing cells than non-CYP1B1 expressing cells (see Table 2 below). Compounds SU025-04 and SU046-04 are therefore demonstrably CYP1B1-activated prodrugs. SU025-04 and SU046-04 exhibit similarly low cytotoxicity to wild-type CHO and CHO/CYP1A1 cells with differential cytotoxicity $IC_{50}$ ratios <1 at 72 h exposure indicating that the highly toxic phosphoramidate mustards are not released by CYP1A1 activation (see Table 2 below). As expected from the literature the two clinically used prodrugs ifosfamide and cyclophosphamide which also generate alkylating isophosphoamidate mustards when activated by CYP2B6 and CYP3A4 but not CYP1 enzymes (e.g.: McFadyen M C, Melvin W T and Murray G I, "Cytochrome P450 Enzymes: Novel Options for Cancer Therapeutics", *Mol Cancer Ther.*, 3(3): 363-71, 2004) are both non-toxic at the highest concentration of 100 µmol $dm^{-3}$ and longest 96 h exposure times used in this cytotoxicity assay (see again Table 2 below).

Example 4

Prodrug Cytotoxicity in Primary Human Tumour Cell Lines

Prodrug Cytotoxicity in a Primary Human Head and Neck Squamous Cell Carcinoma Tumour Cell Line (UT-SCC-14) which Constitutively Expresses CYP1B1

Greer, et al., in *Proc. Am. Assoc. Cancer Res.*, 45: 3701, 2004, reported that CYP1B1 was over-expressed during the malignant progression of head and neck squamous cell carcinoma (HNSCC) but not in normal epithelium. A primary UT-SCC-14 tumour cell line was isolated from a cancer patient with HNSCC (see e.g. Yaromina et. al., *Radiother Oncol.*, 83: 304-10, 2007 and Hessel et al., *Int J Radiat Biol.*, 80; 719-27, 2004. The patient was a male, aged 25, with an HNSCC characterized by the following clinicopathological parameters: location, scc linguae; $T_3$ $N_1$, $M_0$; site, tongue; lesion, primary; grade G2. The UT-SCC-14 cell line constitutively expresses CYP1B1 at the mRNA and protein level and was used to demonstrate compound cytotoxicity in cancer cell derived from a human cancer characterised by over-expression of CYP1B1 (Greer, et al., in *Proc. Am. Assoc. Cancer Res.*, 45: 3701, 2004).

UT-SCC-14 tumour cells: The HNSCC cell line was grown under standard cell culture conditions in EMEM (500 ml) supplemented with foetal calf serum (50 ml), non-essential amino acids (100×, 5 ml), sodium pyruvate (100 mmol $dm^{-3}$, 5 ml), L-glutamine (200 mmol $dm^{-3}$, 5 ml) with penicillin 100 IU/ml/streptomycin (100 µg/ml, 5 ml) according to literature methods (Hessel et al., *Int J Radiat Biol.*, 80; 719-27, 2004, the contents of which are incorporated herein by reference).

Determining Prodrug Cytotoxicity $IC_{50}$ Values in Primary head and Neck Tumour Cell Lines A UT-SCC-14 tumour cell suspension at 2000 cells per well on a 96-well plate and if necessary add fresh media to give a total volume per well of 100 µl. The cells were allowed to attach for 4 h in an incubator. After 4 h it was confirmed that the cells had adhered to the bottom of the 96-well plate under a microscope, then the medium was removed and replaced with fresh medium containing a stock solution of the test compound in ethanol to give the following final concentrations 0, 0.001, 0.003, 0.01, 0.03, 0.1, 0.3, 1, 3, 10, 30, 100 µmol $dm^{-3}$ at a final volume of 100 µl per well. The final concentration of ethanol 0.2% was found not to effect the growth characteristics of the UT-SCC-14 cell line. The UT-SCC-14 cells were incubated with test compound for 72 h after which time all aspirated and replaced with 100 µl of fresh medium to compensate for the loss of medium due to evaporation. The cells were incubated with 20 µl of the MTS assay reagent for 1.5 h and the absorbance per well at 510 nm measured using a plate reader. The mean absorbance and standard deviation for each test compound concentration was calculated versus a series of controls including (a) cells plus medium, (b) cell plus medium containing ethanol 0.2%, (c) medium alone, and (d) medium containing ethanol 0.2% and a range of test compound concentrations from 0 to 100 µmol $dm^{-3}$. The cytotoxicity $IC_{50}$ value was calculated from the plot of the percentage cell growth (where 100% cell growth corresponds to untreated control cells) versus test compound concentration.

Cytotoxicity $IC_{50}$ values are defined herein as the concentration of compound which kills 50% of the UT-SCC-14 tumour cells. The commercially available MTS assay is a homogeneous, colorimetric method for determining the number of viable cells in proliferation, cytotoxicity or chemosensitivity assays and was used as described previously in this Example 3 above.

Two compounds of the invention (SU025-04 and SU046-04), are designed to release the phosphoramide mustards N,N-bis(2-chloro-ethyl)phosphoramide mustard (Cl-IPM) and N,N-bis(2-bromo-ethyl)phosphoramide mustard (Br-IPM), respectively, when activated by CYP1B1. The cytotoxicity $IC_{50}$ values for SU025-04 and SU046-04 in the UT-SCC-14 tumour cells after 72 h exposure were 0.05±0.01 µmol $dm^{-3}$ and 0.02±0.01 µmol $dm^{-3}$, respectively. The data show the potent cytotoxicity of SU025-04 and SU046-04 in the UT-SCC14 cell line from a cancer patient with HNSCC which over-expresses CYP1B1.

SU025-04 and SU046-04 were evaluated in 3 additional primary head and neck cell lines including the UT-SCC-8, the UT-SCC-9 and the UTSCC-10 cultured under the same conditions as the UT-SCC-14. For SU025-04 the cytotoxicity $IC_{50}$ in µmol $dm^{-3}$ were UT-SCC-8 (0.31±0.06), UT-SCC-9 (0.43±0.07), UT-SCC-10 (0.22±0.03) after a 72 h exposure. For SU025-04 the cytotoxicity $IC_{50}$ in µmol $dm^{-3}$ were UT-SCC-8 (0.06±0.02), UT-SCC-9 (0.15±0.02), UT-SCC-10

(0.09±0.03) after a 72 h exposure. The data indicate that SU046-04 is a more potent cytotoxin than SU025-04 across a range of primary head and neck cell lines which constitutively express CYP1B1.

One compound of the invention, SU037-04, was designed to release camptothecin when activated by CYP1B1. For SU037-04 the cytotoxicity $IC_{50}$ in μmol $dm^{-3}$ for each primary tumour cell line was UT-SCC-8 (0.56±0.04), UT-SCC-9 (0.22±0.08), UT-SCC-10 (0.21±0.04), UT-SCC-14 (0.12±0.07) after a 72 h exposure.

One compound of the invention, SU048-04, was designed to release gemcitabine when activated by CYP1B1. The cytotoxicity $IC_{50}$ for SU048-04 in the UT-SCC-14 tumour cell line was 0.94±0.02 μmol $dm^{-3}$ after a 72 h exposure. Co-incubation with α-napthoflavone (a potent CYP1B1 inhibitor) at 10 μmol $dm^{-3}$ significantly reduced the toxicity of SU048-04 to 12.2±0.2 μmol $dm^{-3}$ thereby providing indirect evidence for the activation of the prodrug by CYP1B1 constitutively expressed in the cells.

Example 5

Anti-Tumour Activity of SU046-04 in a Primary Human Tumour Xenograft Model which Constitutively Expresses CYP1B1

Primary UTSCC-14 cell lines 3×10$^6$ were implanted subcutaneously in the flank of nude mice. Mice were randomized to 10 animals per group when the tumour volume was 100 to 150 mm$^3$. SU046-04 was given intraperitoneally at 12, 25 and 50 mg/Kg in PBS versus versus vehicle alone for 2 cycles: daily for 5 days/2 days off. Tumour volume was measured every 4 days using calipers. A significant inhibition of tumour growth was observed in all three treatment arms compared to the vehicle alone. Tumour growth delay at 28 days was 31% at 12 mg/Kg, 56% at 25 mg/Kg, and 90% at 50 mg/Kg with 4/10 complete responses. No observed adverse effects or significant body weight loss after highest exposure 250 mg/Kg.

TABLE 1

Specific CYP1 enzyme activity in Chinese Hamster Ovary (CHO) cells stably transfected with CYP1A1 or CYP1B1 determined using both fluorogenic and luminogenic substrates

| | [a]Specific activity/pmol resorufin or luciferin min$^{-1}$ mg protein$^{-1}$ | | | | | |
|---|---|---|---|---|---|---|
| | CHO | | CHO/CYP1A1 | | CHO/CYP1B1 | |
| | ethoxyresorufin | Luciferin-CEE | ethoxyresorufin | Luciferin-CEE | ethoxyresorufin | Luciferin-CEE |
| chemical inhibitor [b]α-naphthoflavone | nd | nd | 29 ± 4 | 21 ± 3 | 19 ± 3 | 22 ± 4 |
| 10 μmol dm$^{-3}$ [c]TMS | nd | nd | nd | nd | nd | nd |
| 5 μmol dm$^{-3}$ | nd | nd | nd | nd | nd | nd |
| 10 nmol dm$^{-3}$ | nd | nd | 26 ± 4 | 20 ± 5 | 5 ± 2 | 3 ± 2 |

[a]Measured by two methods including the fluoresecent 7-ethoxyresorufin O-deethylation (EROD) assay or the Promega P450-Glo ™ Assay utilizing Luciferin-CEE as a luminogenic substrate for CYP1 enzymes.
Luciferin-CEE for CYP1A1 $K_m$app ~30 μmol dm$^{-3}$
Luciferin-CEE for CYP1B1 $K_m$app ~20 μmol dm$^{-3}$
Ethoxyresorufin for CYP1A1 and CYP1B1 $K_m$ ~0.27 μmol dm$^{-3}$
nd = no detectable activity.
[b]α-naphthoflavone inhibits all CYP1 enzymes at 10 μmol dm$^{-3}$.
[c]Tetramethoxystilbene (TMS) is a selective inhibitor of CYP1B1 with IC$_{50}$ of 6 nmol dm$^{-3}$ 30-fold greater than CYP1A1 and inhibits both enzymes at >1 μmol dm$^{-3}$.

TABLE 2

In vitro cytotoxicity (IC$_{50}$) of prodrugs in a Chinese Hamster Ovary (CHO) cell line stably transfected with CYP1A1 or CYP1B1 compared to isophosphoramide mustard (IPM), cyclophosphamide, and ifosfamide.

| | [a,b,c]Cytotoxicity (IC$_{50}$)/μmol dm$^{-3}$ | | | | | | | |
|---|---|---|---|---|---|---|---|---|
| Compound | CHO 72 h | CHO/CYP1B1 72 h | IC$_{50}$ ratio 72 h | CHO/CYP1A1 72 h | IC$_{50}$ ratio 72 h | CHO 96 h | CHO/CYP1B1 96 h | IC$_{50}$ ratio 96 h |
| SU025-04 | 15.2 ± 0.2 | 0.009 ± 0.005 | 1689 | 25.5 ± 1.0 | <1 | 10.1 ± 0.3 | 0.003 ± 0.002 | 3367 |
| CI-IPM | 0.007 ± 0.004 | 0.008 ± 0.005 | <1 | 0.006 ± 0.002 | 1.2 | | | |
| SU046-04 | 20.3 ± 1.2 | 0.004 ± 0.002 | 5075 | 20.3 ± 2.1 | <1 | 16.2 ± 0.2 | 0.003 ± 0.001 | 5400 |
| Br-IPM | 0.005 ± 0.002 | 0.004 ± 0.002 | 1.25 | 0.005 ± 0.003 | 1 | | | |
| ifosfamide | ND | ND | ND | ND | ND | ND | ND | ND |
| cyclophosphamide | ND | ND | ND | ND | ND | ND | ND | ND |

[a]Cytotoxicity measured using the Promega CellTiter 96 ® AQ$_{ueous}$ Non-Radioactive Cell Proliferation Assay.
[b]Exposure time was 72 or 96 h, dose range 0 to 100 μmol dm$^{-3}$.
[c]IC$_{50}$ ratios calculated from compound IC$_{50}$ in normal CHO cells divided by IC$_{50}$ in CYP1A1 or CYP1B1 transfected CHO cells.
ND = not detectable, indicating <50% toxicity observed at highest compound concentration tested.

TABLE 3

Substituent effect on the fragmentation of benzofuran ether and carbamate linked coumarins by CYP1 enzymes and human liver microsomes (HLM).

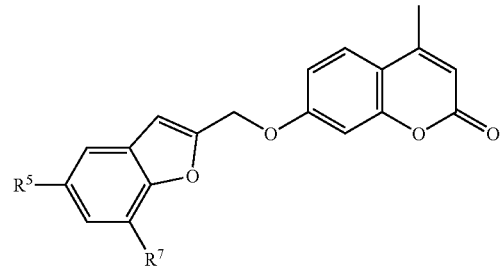

A

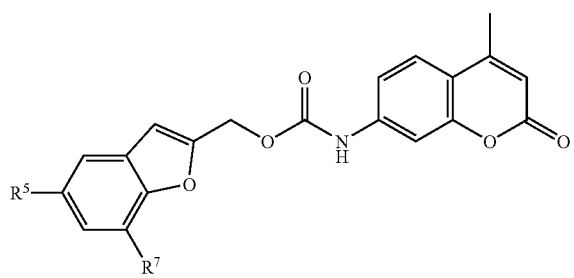

B

| | | | [a,b]Specific fragmentation activity/pmol coumarin min$^{-1}$ pmol cytochrome P450$^{-1}$ | | | |
|---|---|---|---|---|---|---|
| Compound | Structure | Substituent | CYP1A1 | CYP1A2 | CYP1B1 | HLM |
| SU010A | A | $R^5$ = H; $R^7$ = H | 20.91 ± 0.34 | 8.66 ± 0.28 | 5.19 ± 0.15 | 22.8 ± 0.69 |
| VG015-05 | A | $R^5$ = F; $R^7$ = H | 19.35 ± 3.08 | nd | 3.16 ± 0.28 | nd |
| VG016-05 | A | $R^5$ = F; $R^7$ = F | no release | no release | no release | no release |
| VG017-05 | A | $R^5$ = F; $R^7$ = Me | 5.39 ± 1.34 | nd | 2.95 ± 0.59 | nd |
| VG027-05 | A | $R^5$ = MeO; $R^7$ = H | 88.10 ± 5.69 | 20.93 ± 0.59 | 11.83 ± 0.15 | 8.98 ± 0.49 |
| VG029-05 | A | $R^5$ = H; $R^7$ = MeO | 19.53 ± 1.07 | nd | 6.45 ± 1.15 | nd |
| VG035-04 | A | $R^5$ = Br; $R^7$ = H | 28.08 ± 1.98 | nd | 8.85 ± 0.28 | nd |
| VG028-05 | A | $R^5$ = Cl; $R^7$ = H | 17.52 ± 0.83 | nd | 6.67 ± 0.01 | nd |
| VG035-05 | A | $R^5$ = MeO; $R^7$ = MeO | no release | no release | 13.65 ± 1.00 | no release |
| SU018-03 | B | $R^5$ = H; $R^7$ = H | 2.41 ± 0.18 | no release | no release | no release |
| VG032-05 | B | $R^4$ = MeO; $R^7$ = H | 12.19 ± 3.02 | no release | 1.53 ± 0.09 | 3.21 ± 0.25 |
| VG036-05 | B | $R^5$ = Br; $R^7$ = H | no release | no release | no release | no release |
| VG041-05 | B | $R^5$ = MeO; $R^7$ = MeO | 5.51 ± 0.06 | no release | no release | no release |

[a]Ether or carbamate linker fragmentation was monitored by coumarin anion release by kinetic fluorimetry using excitation/emission wavelengths:
$\lambda_{ex}$ = 350 nm/$\lambda_{em}$ = 450 nm. CYP1 enzyme concentration was 10 pmol and the volume of HLM was 60 μl in a final reaction volume of 1.5 ml.
Specific fragmentation activities are quoted as the mean ± standard deviation of three measurements. nd = not determined.

The invention claimed is:

1. A compound of formula (I):

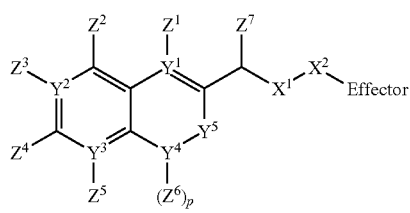

(I)

or pharmaceutically acceptable salt, ester, amide or solvate thereof, wherein:

$X^1$ is such that —$X^1$—$X^2$ is —O—$X^2$, —S—$X^2$, —$SO_2$—O—$X^2$, —$SO_2NZ^{10}$—$X^2$, conjugated alkenemethyloxy or conjugated alkenemethylthio, conjugated alkenemethyl$SO_2$—O, conjugated alkenemethyl-$SO_2NZ^{10}$ or of the formula:

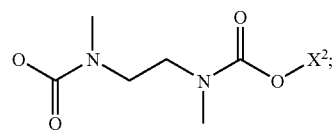

—$X^2$ is absent or is such that $X^1$—$X^2$-Effector is one of

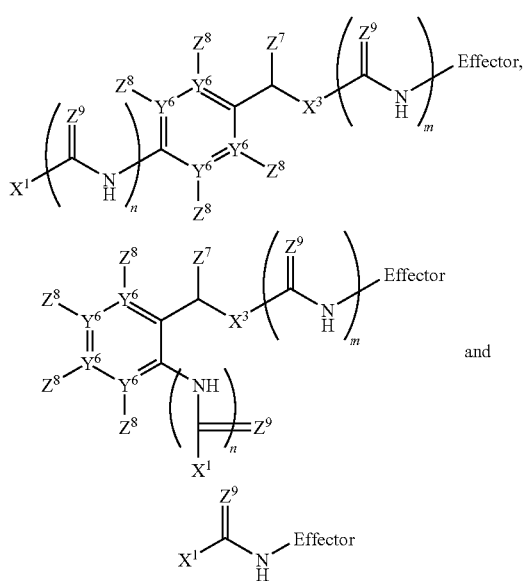

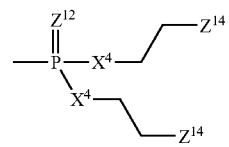

each n and m is independently 0 or 1;

p is 0, 1 or 2;

$X^3$ is oxygen or sulfur and additionally, when m=0, may be $SO_2$—O, $SO_2NZ^{10}$, conjugated alkenemethyloxy, conjugated alkenemethylthio, conjugated alkenemethyl-$SO_2$—O or conjugated alkenemethyl-$SO_2NZ^{10}$ each of $Y^1$, $Y^2$ and $Y^3$ is carbon;

$Y^4$ is oxygen, sulfur, sulfoxide or sulfone;

—$Y^5$— is a single bond;

each of $Z^1$-$Z^4$, where present, are independently selected from hydrogen, alkyl, alkenyl, alkynyl, aryl, aralkyl, alkyloxy, alkenyloxy, alkynyloxy, aryloxy, aralkyloxy, alkylthioxy, alkenylthioxy, alkynylthioxy, arylthioxy, aralkylthioxy, amino, hydroxy, thio, halo, carboxy, formyl, nitro and cyano;

$Z^5$, where present, is independently selected from hydrogen alkyl, alkenyl, alkynyl, aryl, aralkyl, alkyloxy, alkenyloxy, alkynyloxy, aryloxy, aralkyloxy, alkylthioxy, alkenylthioxy, alkynylthioxy, arylthioxy, aralkylthioxy, amino, hydroxy, thio, carboxy, formyl, nitro and cyano;

or one of $Z^2$ & $Z^3$, $Z^3$ & $Z^4$ and $Z^4$ and $Z^5$ together with the atoms to which they are connected form an aromatic ring fused to the remainder of the compound;

provided that at least one of $Z^1$, $Z^2$ and $Z^4$ is hydrogen;

$Z^6$ is selected from hydrogen, alkyl, alkenyl, alkynyl, aryl and aralkyl;

none, one or two of $Y^6$ may be nitrogen atoms with the remainder being carbon atoms;

each $Z^7$ is independently hydrogen, alkyl or aryl;

each $Z^8$ is independently selected from hydrogen, an electron withdrawing group, unsubstituted $C_1$-$C_6$ alkyl, substituted $C_1$-$C_6$ alkyl, unsubstituted $C_1$-$C_6$ alkoxy, and substituted $C_1$-$C_6$ alkoxy where the substituted alkyl or alkoxy are substituted with one or more groups selected from ether, amino, mono- or di-substituted amino, cyclic $C_1$-$C_5$ alkylamino, imidazolyl, $C_1$-$C_6$ alkylpiperazinyl, morpholino, thiol, thioether, tetrazole, carboxylic acid, ester, amido, mono- or di-substituted amido, N-connected amide, N-connected sulfonamide, sulfoxy, sulfonate, sulfonyl, sulfoxy, sulfinate, sufinyl, phosphonooxy, phosphate and sulfonamide;

each $Z^9$ is independently oxygen or sulfur;

$Z^{10}$ is hydrogen or alkyl, for example a $C_{1-4}$alkyl; and

Effector is a molecule of formula (II);

$$\text{—}\overset{\overset{\displaystyle Z^{12}}{\|}}{\underset{\underset{\displaystyle X^4\text{—}}{|}}{P}}\text{—}X^4\text{—}Z^{14} \qquad (II)$$

$$\phantom{XXXXXX}\searrow Z^{14}$$

wherein:

$Z^{12}$ is oxygen or sulfur;

each $X^4$ is independently oxygen, sulfur or $NZ^{13}$, wherein each —$Z^{13}$ is independently —$(CH_2)_2$—$Z^{14}$, -alkyl or -hydrogen; and each $Z^{14}$ is independently chloro, bromo, iodo or mesylate.

2. The compound, or pharmaceutically acceptable salt, ester, amide or solvate of claim 1, wherein the or each $Z^7$ is hydrogen.

3. The compound, or pharmaceutically acceptable salt, ester, amide or solvate of claim 1, wherein $X^1$ is oxygen.

4. The compound, or pharmaceutically acceptable salt, ester, amide or solvate of claim 1, wherein $Z^3$ and $Z^5$ are each alkoxy or amino.

5. The compound, or pharmaceutically acceptable salt, ester, amide or solvate of claim 1, wherein $Z^3$ and $Z^5$ are each $C_{1-6}$alkoxy.

6. The compound, or pharmaceutically acceptable salt, ester, amide or solvate of claim 5, wherein $Z^3$ and $Z^5$ are each methoxy.

7. The compound, or pharmaceutically acceptable salt, ester, amide or solvate of claim 1, wherein $Z^1$ is alkoxy or amino.

8. The compound, or pharmaceutically acceptable salt, ester, amide or solvate of claim 1, wherein $Z^1$ is hydrogen.

9. The compound, or pharmaceutically acceptable salt, ester, amide or solvate of any one of claims 1 to 8, wherein $Z^2$— is hydrogen, $Z^4$ is hydrogen, or both $Z^2$ and $Z^4$ are hydrogen.

10. The compound, or pharmaceutically acceptable salt, ester, amide or solvate of claim 1, wherein $Y^4$ is oxygen or sulfur.

11. The compound, or pharmaceutically acceptable salt, ester, amide or solvate of claim 10, wherein p=0.

12. The compound, or pharmaceutically acceptable salt, ester, amide or solvate of claim 11, wherein $Y^4$ is oxygen.

13. The compound, or pharmaceutically acceptable salt, ester, amide or solvate of claim 1, wherein $Z^3$ is selected from hydrogen alkyl, alkenyl, alkynyl, aryl, aralkyl, alkyloxy, alkenyloxy, alkynyloxy, aryloxy, aralkyloxy, alkylthioxy, alkenylthioxy, alkynylthioxy, arylthioxy, aralkylthioxy, amino, hydroxy, thio, carboxy, formyl, nitro and cyano.

14. The compound, or pharmaceutically acceptable salt, ester, amide or solvate of claim 1, wherein $X^1$ is such that —$X^1$—$X^2$ is —O—$X^2$, —S—$X^2$, —$SO_2$—$OX^2$ or —$SO_2NZ^{10}$—$X^2$.

15. The compound, or pharmaceutically acceptable salt, ester, amide or solvate of claim 14, wherein $X^1$ is such that —$X^1$—$X^2$ is —O—$X^2$.

16. The compound, or pharmaceutically acceptable salt, ester, amide or solvate of claim 1, wherein $X^2$ is present.

17. The compound, or pharmaceutically acceptable salt, ester, amide or solvate of claim 1, wherein $X^2$ is absent or $X^1$—$X^2$-Effector is of the formula:

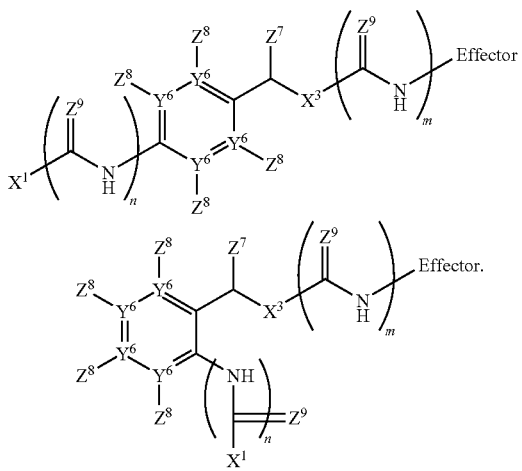

18. The compound, or pharmaceutically acceptable salt, ester, amide or solvate of claim 16 or claim 17, wherein one of n and m is 0 or both n and m are 0.

19. The compound, or pharmaceutically acceptable salt, ester, amide or solvate of claim 16, wherein each $Z^9$ is oxygen.

20. The compound, or pharmaceutically acceptable salt, ester, amide or solvate of claim 16, wherein none or one of $Y^6$ are nitrogen.

21. The compound, or pharmaceutically acceptable salt, ester, amide or solvate of claim 1, wherein $X^2$ is absent.

22. The compound, or pharmaceutically acceptable salt, ester, amide or solvate of claim 1 wherein $Z^{12}$ is oxygen.

23. The compound, or pharmaceutically acceptable salt, ester, amide or solvate of claim 1, wherein each $X^4$ is $NZ^{13}$.

24. The compound, or pharmaceutically acceptable salt, ester, amide or solvate of claim 23, wherein each $Z^{13}$ is hydrogen.

25. The compound, or pharmaceutically acceptable salt, ester, amide or solvate of claim 1, wherein each $Z^{14}$ is bromo or chloro.

26. The compound, or pharmaceutically acceptable salt, ester, amide or solvate of claim 25, wherein each $Z^{14}$ is bromo.

27. A composition comprising a compound, or pharmaceutically acceptable salt, ester, amide or solvate, as defined in claim 1 together with a pharmaceutically acceptable carrier.

28. A compound having the structure:

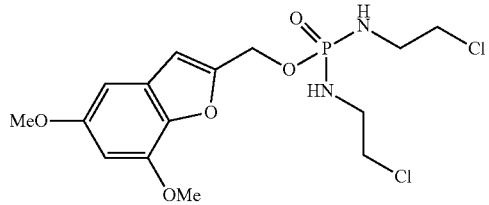

or pharmaceutically acceptable salt thereof.

29. A compound having the structure:

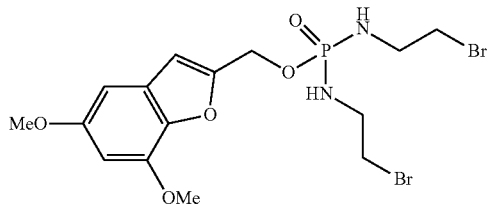

or pharmaceutically acceptable salt thereof.

* * * * *